United States Patent
Eary et al.

(10) Patent No.: US 10,745,419 B2
(45) Date of Patent: Aug. 18, 2020

(54) PROCESS FOR THE PREPARATION OF 6-(2-HYDROXY-2-METHYLPROPOXY)-4-(6-(6-((6-METHOXYPYRIDIN-3-YL)METHYL)-3,6-DIAZABICYCLO[3.1.1]HEPTAN-3-YL)PYRIDIN-3-YL)PYRAZOLO[1,5-A]PYRIDINE-3-CARBONITRILE

(71) Applicants: Loxo Oncology, Inc., Stamford, CT (US); Array BioPharma Inc., Boulder, CO (US)

(72) Inventors: Charles Todd Eary, Stamford, CT (US); Stacey Spencer, Boulder, CO (US); Zack Crane, Longmont, CO (US); Katelyn Chando, Longmont, CO (US); Sylvie Asselin, Longmont, CO (US); Weidong Liu, Longmont, CO (US); Mike Welch, Longmont, CO (US); Adam Cook, Boulder, CO (US); Gabrielle R. Kolakowski, Boulder, CO (US); Andrew T. Metcalf, Boulder, CO (US); David A. Moreno, Boulder, CO (US); Tony P. Tang, Boulder, CO (US)

(73) Assignees: Loxo Oncology Inc., Stamford, CT (US); Array Biopharma Inc., Boulder, CO (US)

(*) Notice: Subject to any disclaimer, the term of this patent is extended or adjusted under 35 U.S.C. 154(b) by 0 days.

(21) Appl. No.: 16/156,955

(22) Filed: Oct. 10, 2018

(65) Prior Publication Data

US 2019/0106438 A1 Apr. 11, 2019

Related U.S. Application Data

(60) Provisional application No. 62/570,565, filed on Oct. 10, 2017.

(51) Int. Cl.
*C07D 519/00* (2006.01)
*C07D 471/04* (2006.01)

(52) U.S. Cl.
CPC .......... *C07D 519/00* (2013.01); *C07D 471/04* (2013.01)

(58) Field of Classification Search
CPC .................................................. C07D 519/00
See application file for complete search history.

(56) References Cited

U.S. PATENT DOCUMENTS 10,112,942 B2 * 10/2018 Andrews .............. A61K 31/506
2012/0277247 A1 11/2012 Menet et al.

FOREIGN PATENT DOCUMENTS

WO 2017/011776 A1 1/2017
WO 2018/071447 A1 4/2018

OTHER PUBLICATIONS

Vyvyan "Suzuki-Miyaura cross-coupling of 3-pyridyl triflates with 1-alkenyl-2-pinacol boronates" Synthesis (Stuttg). Nov. 2010; 2010(21): 3637-3644.*
Abdel-Magid et al, "Reductive Amination of Aldehydes and Ketones with Sodium Triacetoxyborohydride. Studies on Direct and Indirect Reductive Amination Procedures", J. Org. Chem, 1996, 61, 3849-3862.
Legault and Charette, "Highly Efficient Synthesis of O-(2,4-Dinitrophenyl)hydroxylamine. Application to the Synthesis of SubstitutedN-Benzoy liminopyridinium Ylides", J. Org. Chem., 2003, vol. 68, No. 18, 7119-7122.
Vorogushin et al, Use of Tunable Ligands Allows for Internolecular Pd-Catalyzed C—O Bond Formation, JACS Communications, 2005.
Anderson et al, "The Selective Reaction of Aryl Halides with KOH: Synthesis of Phenols, Aromatic Ethers, and Benzofurans", JACS Communications, 2006.
Fier and Maloney, Direct Conversion of Haloarenes to Phenols under Mild, Transition-Metal-Free Conditions, Organic Letters, 2016.
PCT International Search Report of the International Searching Authority pertaining to international Application No. PCT/2018/055255; dated Dec. 17, 2018; 3 pages.
PCT Written Opinion of the International Searching Authority pertaining to international Application No. PCT/2018/055255; dated Dec. 17, 2018; 5 pages.

* cited by examiner

*Primary Examiner* — David K O'Dell
(74) *Attorney, Agent, or Firm* — Michael R. Asam

(57) ABSTRACT

In some embodiments, provided herein is a process for preparing a compound of Formula I

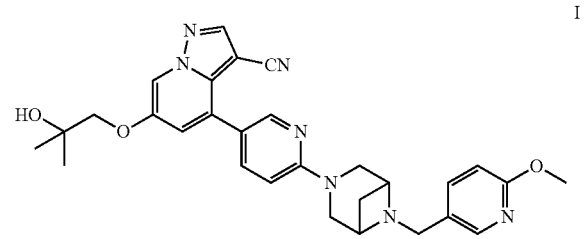

or a pharmaceutically acceptable salt thereof, as disclosed herein.

19 Claims, No Drawings

PROCESS FOR THE PREPARATION OF 6-(2-HYDROXY-2-METHYLPROPOXY)-4-(6-(6-((6-METHOXYPYRIDIN-3-YL)METHYL)-3,6-DIAZABICYCLO[3.1.1]HEPTAN-3-YL)PYRIDIN-3-YL)PYRAZOLO[1,5-A]PYRIDINE-3-CARBONITRILE

CROSS-REFERENCE TO RELATED APPLICATIONS

This application claims priority to U.S. Provisional Application Ser. No. 62/570,565, filed on Oct. 10, 2017, the contents of which is hereby incorporated by reference in its entirety.

PARTIES TO A JOINT RESEARCH AGREEMENT

The present invention was made under a Joint Research Agreement between Array BioPharma Inc. and Loxo Oncology, Inc. The Joint Research Agreement was in effect on or before the date the present invention was made, and the present invention was made as a result of the activities undertaken within the scope of the Joint Research Agreement.

TECHNICAL FIELD

Provided herein are processes and intermediates useful for the preparation of a compound of Formula I:

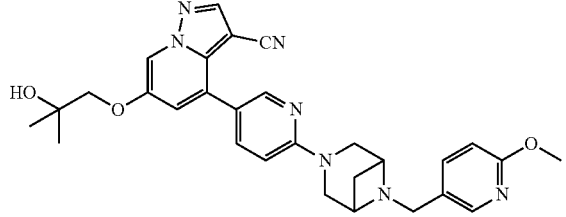

I or a pharmaceutically acceptable salt thereof.

BACKGROUND

The compound of Formula I

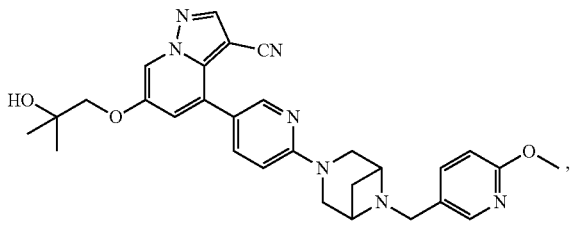

I 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile, including pharmaceutically acceptable salts thereof, exhibits rearranged during transfection (RET) kinase inhibition.

A need exists for alternative synthetic procedures for the preparation of the compound of Formula I and pharmaceutically acceptable salts thereof. Such alternative synthetic procedures are provided herein.

SUMMARY

Provided herein is a process for preparing a compound of Formula I:

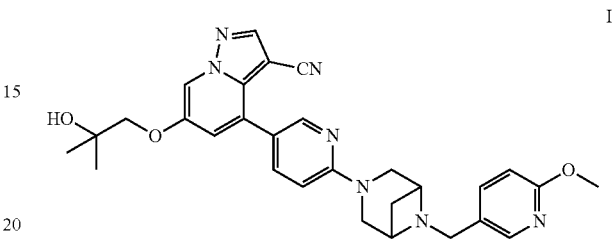

I or a pharmaceutically acceptable salt thereof. In some embodiments, the process comprises:
treating a compound of formula 16

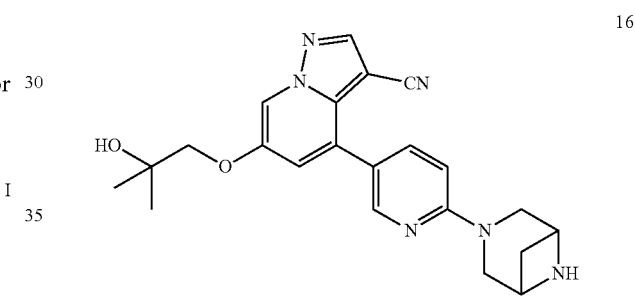

16 or a salt thereof with 6-methoxynicotinaldehyde and a reducing agent to form the compound of Formula I or a pharmaceutically acceptable salt thereof.

In some embodiments, the process for preparing a compound of Formula I further comprises preparing the compound of formula 16, the process comprising treating a compound of formula 15

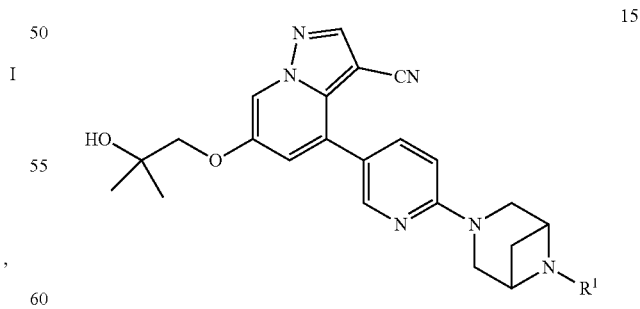

15 or a salt thereof, wherein $R^1$ is an amine protecting group, with a deprotecting agent to form the compound of formula 16 or a salt thereof.

In some embodiments, the process for preparing a compound of Formula I further comprises preparing the compound of formula 15 or a salt thereof, wherein $R^1$ is an amine protecting group, the process comprising:
treating a compound of formula 13

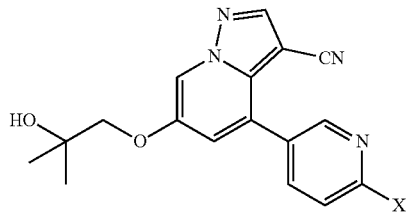

13 or a salt thereof, wherein X represents a halogen or a sulfonate, with a compound of formula 14

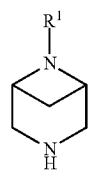

14 or a salt thereof, wherein $R^1$ is an amine protecting group, to form the compound of formula 15 or a salt thereof.

In some embodiments, the process for preparing a compound of Formula I further comprises preparing the compound of formula 13 or a salt thereof, the process comprising treating a compound of formula 20

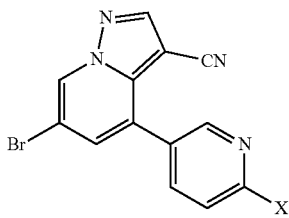

20 or a salt thereof, wherein X represents a halogen or a sulfonate, with a compound of formula 21

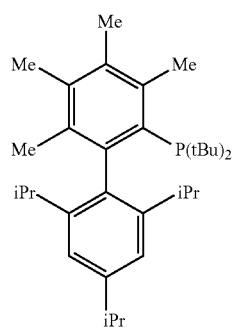

21 in the presence of 2,2-dimethyloxirane, a first catalyst comprising a metal, and a first weak base to form the compound of formula 13 or a salt thereof.

In some embodiments, the process for preparing a compound of Formula I further comprises preparing the compound of formula 13 or a salt thereof, the process comprising: a) treating a compound of formula 20 or a salt thereof with a first diboronic acid or ester in the presence of a second catalyst comprising a metal to form a compound of formula 22

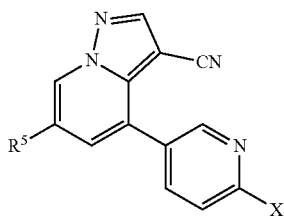

22 or a salt thereof, wherein X represents a halogen or a sulfonate and $R^5$ represents a boronic acid or ester with the boron atom as the point of attachment to the pyrazolopyridine ring of compound 22 or a salt thereof;

b) treating the compound of formula 22 or a salt thereof with a first strong base and hydrogen peroxide to form a compound of formula 23

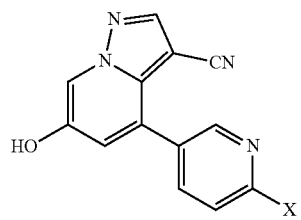

23 or a salt thereof, wherein X represents a halogen or a sulfonate; and c) treating the compound of formula 23 or a salt thereof with 2,2-dimethyloxirane in the presence of a second strong base to form the compound of formula 13 or a salt thereof.

In some embodiments, the process for preparing a compound of Formula I further comprises preparing the compound of formula 13 or a salt thereof, the process comprising:

treating a compound of formula 35

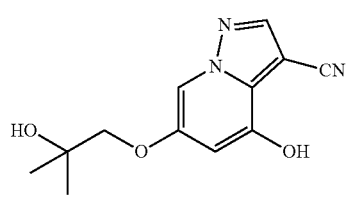

35 or a salt thereof with a first triflating reagent to form a compound of formula 36

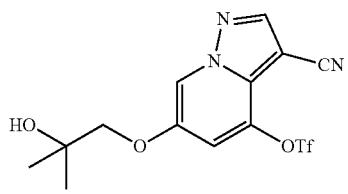

36 or a salt thereof; and treating the compound of formula 36 or a salt thereof with a compound of formula 12

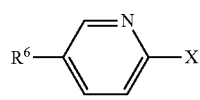

12 or a salt thereof, wherein X represents a halogen or a sulfonate and $R^6$ represents a boronic acid or ester with the boron atom as the point of attachment to the pyridine ring of compound 12, in the presence of a third catalyst comprising a metal to form the compound of formula 13 or a salt thereof.

In some embodiments, the process for preparing a compound of Formula I further comprises preparing the compound of formula 35 or a salt thereof, the process comprising:

treating a compound of formula 33

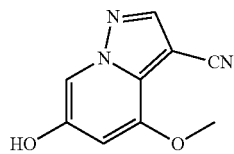

33 or a salt thereof with 2,2-dimethyloxirane in the presence of a third strong base to form the compound of formula 34

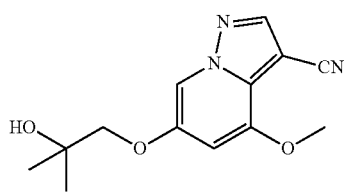

34 or a salt thereof; and treating the compound of formula 34 or a salt thereof with a first dealkylating agent to form the compound of formula 35 or a salt thereof.

In some embodiments, the process for preparing a compound of Formula I further comprises preparing the compound of formula 33 or a salt thereof, the process comprising:

treating a compound of formula A

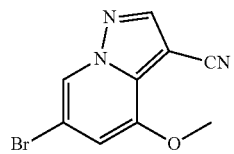

A or a salt thereof with a second diboronic acid or ester in the presence of a fourth catalyst comprising a metal to form a compound of formula 32

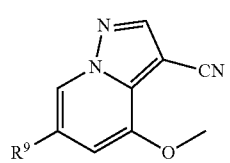

32 or a salt thereof, wherein $R^9$ represents a boronic acid or ester with the boron atom as the point of attachment to the pyrazolopyridine ring of compound 32 or a salt thereof; and treating the compound of formula 32 or a salt thereof with a first oxidant to form the compound of formula 33 or a salt thereof.

In some embodiments, the process for preparing a compound of Formula I further comprises preparing the compound of formula 20 or a salt thereof, the process comprising treating a compound of formula 19

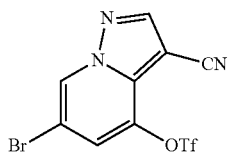

19 or a salt thereof with a compound of formula 12

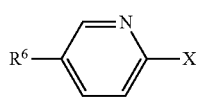

12 or a salt thereof, wherein X represents a halogen or a sulfonate and $R^6$ represents a boronic acid or ester with the boron atom as the point of attachment to the pyridine ring of compound 12, in the presence of a eighth catalyst comprising a metal to form the compound of formula 20 or a salt thereof.

Also provided herein is a process for preparing a compound of Formula I

I

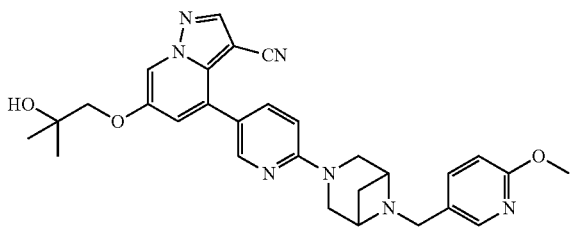

or a pharmaceutically acceptable salt thereof, wherein the process comprises treating a compound of formula 29

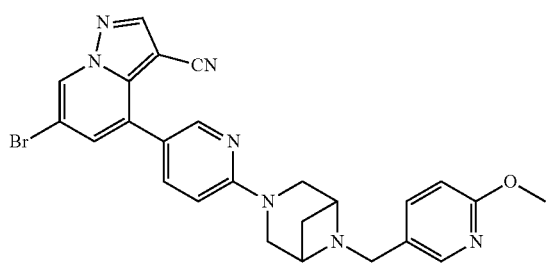

29 or a salt thereof with a compound of formula 21

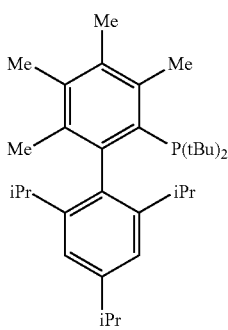

21 in the presence of 2,2-dimethyl dioxirane, a sixth catalyst comprising a metal, and a second weak base to form the compound of Formula I or a pharmaceutically acceptable salt thereof.

Also provided herein is a process for preparing a compound of Formula I

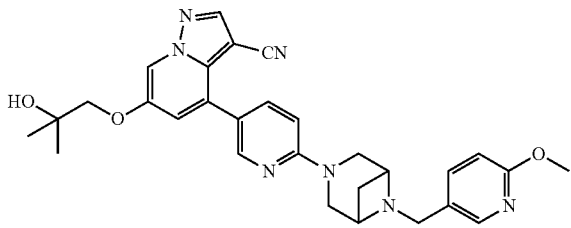

I or a pharmaceutically acceptable salt thereof, wherein the process comprises:

a) treating a compound of formula 29

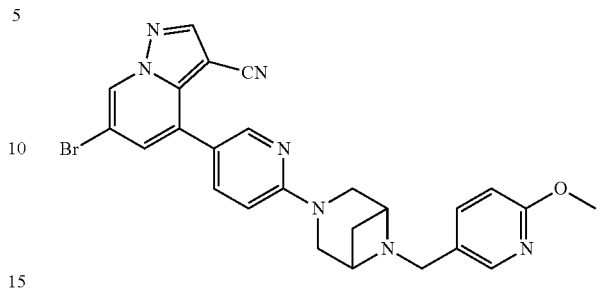

29 or a salt thereof with a third diboronic acid or ester in the presence of a seventh catalyst comprising a metal to form a compound of formula 30

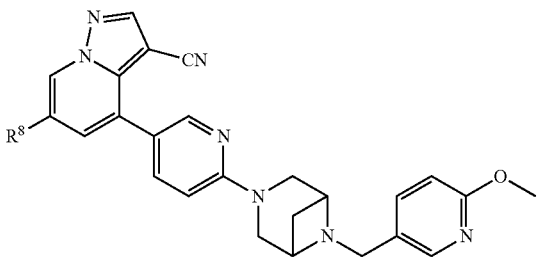

30 or a salt thereof, wherein $R^8$ represents a boronic acid or ester with the boron atom as the point of attachment to the pyrazolopyridine ring of compound 30 or a salt thereof;

b) treating the compound of formula 30 or a salt thereof with a fourth strong base and hydrogen peroxide to form a compound of formula 31

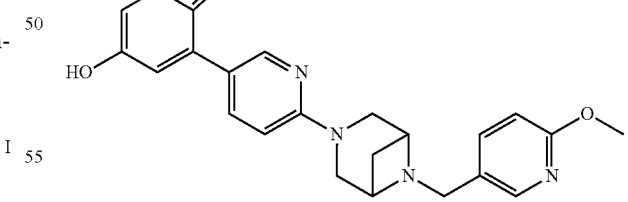

31 or a salt thereof; and c) treating the compound of formula 31 or a salt thereof with 2,2-dimethyloxirane in the presence of a fifth strong base to form the compound of Formula I or a pharmaceutically acceptable salt thereof.

In some embodiments, the process for preparing a compound of Formula I further comprises preparing the compound of formula 29, the process comprising:

treating a compound of formula 19

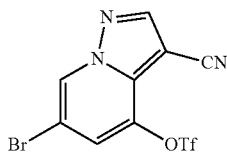

or a salt thereof with a compound of formula 28

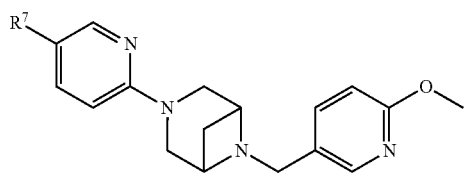

or a salt thereof, wherein R⁷ represents a boronic acid or ester with the boron atom as the point of attachment to the pyridine ring of compound 28, in the presence of a fifth catalyst comprising a metal to form the compound of formula 29 or a salt thereof.

In some embodiments, the process for preparing a compound of Formula I further comprises preparing the compound of formula 19 or a salt thereof, the process comprising:

treating a compound of formula A

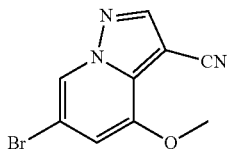

or a salt thereof with a second dealkylating agent to form a compound of formula 18

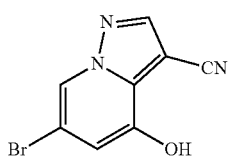

or a salt thereof; and treating the compound of formula 18 or a salt thereof with a second triflating reagent to form the compound of formula 19 or a salt thereof.

In some embodiments, the process for preparing a compound of Formula I further comprises preparing the compound of formula A or a salt thereof by a process comprising:

a) treating a compound of formula 1a

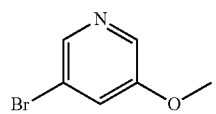

or a salt thereof with O-(mesitylsulfonyl)hydroxylamine to form a compound of formula 2a

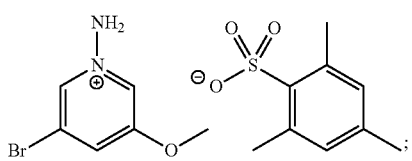

and b) treating the compound of formula 2a with acrylonitrile or an acrylonitrile derivative in the presence of a first non-nucleophilic base to form the compound of formula A; or, alternatively, preparing the compound of formula A or a salt thereof by a process comprising:

a) treating a compound of formula 8A

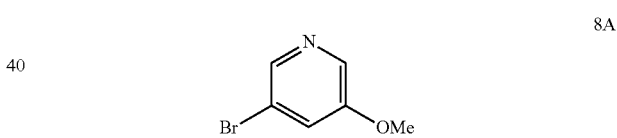

or a salt thereof with O-(2,4-dinitrophenyl)hydroxylamine to form a compound of formula 9A

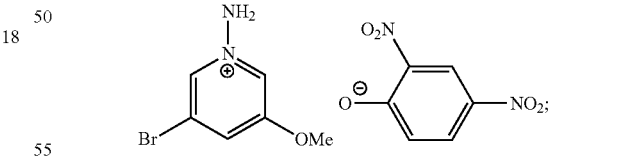

and b) treating the compound of formula 9A with acrylonitrile or an acrylonitrile derivative in the presence of a first non-nucleophilic base to form the compound of formula A.

In some embodiments, the process for preparing a compound of Formula I further comprises preparing the compound of formula 15

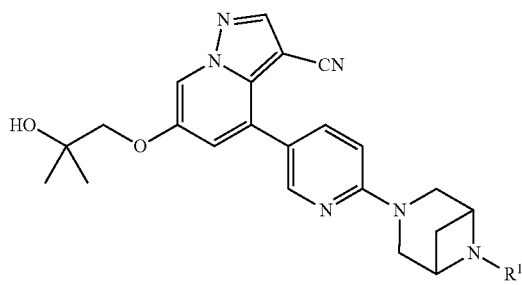

15 or a salt thereof, wherein R¹ is an amine protecting group, comprising:

treating a compound of formula 26

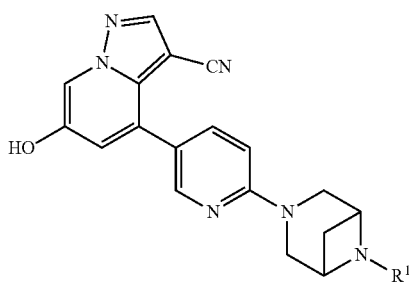

26 or a salt thereof, wherein R¹ is an amine protecting group, with 2,2-dimethyloxirane in the presence of a sixth strong base to form the compound of formula 15 or a salt thereof.

In some embodiments, the process for preparing a compound of Formula I further comprises preparing the compound of formula 26 or a salt thereof, the process comprising:

a) treating a compound of formula B

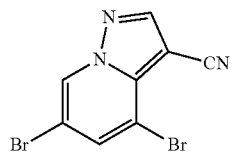

B or a salt thereof with a compound of formula 24

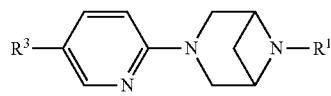

24 or a salt thereof, wherein R¹ is an amine protecting group and R³ represents a boronic acid or ester with the boron atom as the point of attachment to the pyridine ring of compound 24, in the presence of a ninth catalyst comprising a metal to form a compound of formula 25

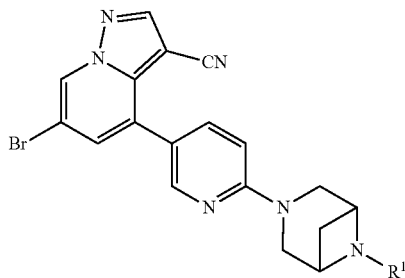

25 or a salt thereof; and b) treating the compound of formula 25 with a fourth diboronic acid or ester in the presence of a tenth catalyst comprising a metal to form a mixture, and treating the mixture with a seventh strong base and hydrogen peroxide to form the compound of formula 26 or a salt thereof.

In some embodiments, the process for preparing a compound of Formula I further comprises preparing the compound of formula B or a salt thereof by a process comprising:

a) treating a compound of formula 8

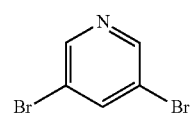

8 or a salt thereof with O-(mesitylsulfonyl)hydroxylamine to form the compound of formula 9

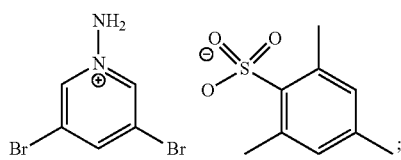

9 and b) treating the compound of formula 9 with acrylonitrile or an acrylonitrile derivative in the presence of a second non-nucleophilic base to form a mixture, and treating the mixture with a second oxidant to form the compound of formula B.

In some embodiments of the process for preparing a compound of Formula I provided herein, the reducing agent is selected from the group consisting of an alkali metal borohydride, a hydrazine compound, citric acid, a citric acid salt, succinic acid, a succinic acid salt, ascorbic acid, and an ascorbic acid salt. In some embodiments, the reducing agent is selected from the group consisting of a sodium borohydride, a lithium borohydride, a nickel borohydride, and a potassium borohydride. In some embodiments, the reducing agent is sodium triacetoxy borohydride (STAB).

In some embodiments of the process for preparing a compound of Formula I provided herein, the deprotecting agent is selected from the group consisting of trifluoroacetic acid, hydrochloric acid, hydrobromic acid, hydriodic acid, phosphoric acid, sulfuric acid, methanesulfonic acid, p-toluene sulfonic acid, acetyl chloride, aluminum trichloride, and boron trifluoride. In some embodiments, the deprotecting agent is sulfuric acid.

In some embodiments of the process for preparing a compound of Formula I provided herein, X is a halogen selected from the group consisting of F, Br, Cl, and I. In some embodiments, X is F. In some embodiments, X is a sulfonate selected from the group consisting of triflate, mesylate, and tosylate.

In some embodiments of the process for preparing a compound of Formula I provided herein, $R^1$ is an amine protecting group selected from the group consisting of formyl, acetyl, trifluoroacetyl, benzyl, benzoyl, carbamate, benzyloxycarbonyl, p-methoxybenzyl carbonyl, tert-butyloxycarbonyl (Boc), trimethylsilyl, 2-trimethylsilyl-ethanesulfonyl, trityl and substituted trityl groups, allyloxycarbonyl, 9-fluorenylmethyloxycarbonyl, nitroveratryloxycarbonyl, p-methoxybenzyl, and tosyl. In some embodiments, $R^1$ is tert-butyloxycarbonyl (Boc).

In some embodiments of the process for preparing a compound of Formula I provided herein, the metal of the first catalyst is selected from the group consisting of nickel, palladium, and platinum. In some embodiments, the first catalyst is a palladium catalyst selected from the group consisting of $Pd(dba)_2$, $PdCl_2$, $Pd(OAc)_2$, $Pd(dppf)Cl_2$, $Pd_2(dba)_3$, $PdCl_2(CH_3CN)_2$, $PdCl_2(PPh_3)_2$, $Pd(t-Bu)_3$, $Pd(dppf)Cl_2 \cdot CH_2Cl_2$, $Pd(PPh_3)_4$, $Pd(OAc)/PPh_3$, $PdCl_2[(Pet_3)]_2$, $Pd(DIPHOS)_2$, $PdCl_2(Bipy)$, $[PdCl(Ph_2PCH_2PPh_2)]_2$, $PdCl_2[P(o-Tol)_3]_2$, $Pd_2(dba)_3/P(o-Tol)_3$, $Pd_2(dba)/P(furyl)_3$, $PdCl_2[P(furyl)_3]_2$, $PdCl_2(PMePh_2)_2$, $PdCl_2[P(4-F-Ph)_3]_2$, $PdCl_2[P(C_6F_6)_3]_2$, $PdCl_2[P(2-COOH-Ph)(Ph)_2]_2$, and $PdCl_2[P(4-COOH-Ph)(Ph)_2]_2$. In some embodiments, the first catalyst is $Pd_2(dba)_3$.

In some embodiments of the process for preparing a compound of Formula I provided herein, the first weak base is selected from the group consisting of a carbonate, a bicarbonate, methyl amine, ammonia, trimethyl ammonia, pyridine, and aniline. In some embodiments, the first weak base is cesium carbonate ($Cs_2CO_3$).

In some embodiments of the process for preparing a compound of Formula I provided herein, the metal of the second catalyst is selected from the group consisting of nickel, palladium, and platinum. In some embodiments, the second catalyst is a palladium catalyst selected from the group consisting of $Pd(dba)_2$, $PdCl_2$, $Pd(OAc)_2$, $Pd(dppf)Cl_2$, $Pd_2(dba)_3$, $PdCl_2(CH_3CN)_2$, $PdCl_2(PPh_3)_2$, $Pd(t-Bu)_3$, $Pd(dppf)Cl_2 \cdot CH_2Cl_2$, $Pd(PPh_3)_4$, $Pd(OAc)/PPh_3$, $PdCl_2[(Pet_3)]_2$, $Pd(DIPHOS)_2$, $PdCl_2(Bipy)$, $[PdCl(Ph_2PCH_2PPh_2)]_2$, $PdCl_2[P(o-Tol)_3]_2$, $Pd_2(dba)_3/P(o-Tol)_3$, $Pd_2(dba)/P(furyl)_3$, $PdCl_2[P(furyl)_3]_2$, $PdCl_2(PMePh_2)_2$, $PdCl_2[P(4-F-Ph)_3]_2$, $PdCl_2[P(C_6F_6)_3]_2$, $PdCl_2[P(2-COOH-Ph)(Ph)_2]_2$, and $PdCl_2[P(4-COOH-Ph)(Ph)_2]_2$. In some embodiments, the second catalyst is $Pd(dppf)Cl_2 \cdot CH_2Cl_2$.

In some embodiments of the process for preparing a compound of Formula I provided herein, the first diboronic acid or ester is selected from the group consisting of an alkenyl boronic acid, an alkyl boronic acid, an aryl boronic acid, a heteroaryl boronic acid, and a pinacol boronic ester. In some embodiments, the first diboronic acid or ester is bis(pinacolato)diboron.

In some embodiments of the process for preparing a compound of Formula I provided herein, the first strong base and second strong base are independently selected from the group consisting of lithium hydroxide, sodium hydroxide, potassium hydroxide, rubidium hydroxide, cesium hydroxide, calcium hydroxide, strontium hydroxide, and barium hydroxide. In some embodiments, the first strong base is sodium hydroxide. In some embodiments, the second strong base is sodium hydroxide.

In some embodiments of the process for preparing a compound of Formula I provided herein, $R^5$ is boronic acid pinacol ester represented by the formula:

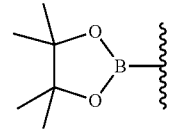

wherein the wavy line indicates the point of attachment to the pyrazolo[1,5-a]pyridine ring of compound 22.

In some embodiments of the process for preparing a compound of Formula I provided herein, the first triflating reagent is selected from the group consisting of N-phenyl-bis(trifluoromethanesulfonimide), N-(5-chloro-2-pyridyl)triflimide, N-(2-pyridyl)triflimide, trifluoromethanesulfonic anhydride, a trialkylsilyl triflate, and a trialkylstannyl triflate. In some embodiments, the first triflating reagent is N-phenyl-bis(trifluoromethanesulfonimide).

In some embodiments of the process for preparing a compound of Formula I provided herein, the metal of the third catalyst is selected from the group consisting of nickel, palladium, and platinum. In some embodiments, the third catalyst is a palladium catalyst selected from the group consisting of $Pd(dba)_2$, $PdCl_2$, $Pd(OAc)_2$, $Pd(dppf)Cl_2$, $Pd_2(dba)_3$, $PdCl_2(CH_3CN)_2$, $PdCl_2(PPh_3)_2$, $Pd(t-Bu)_3$, $Pd(dppf)Cl_2 \cdot CH_2Cl_2$, $Pd(PPh_3)_4$, $Pd(OAc)/PPh_3$, $PdCl_2[(Pet_3)]_2$, $Pd(DIPHOS)_2$, $PdCl_2(Bipy)$, $[PdCl(Ph_2PCH_2PPh_2)]_2$, $PdCl_2[P(o-Tol)_3]_2$, $Pd_2(dba)_3/P(o-Tol)_3$, $Pd_2(dba)/P(furyl)_3$, $PdCl_2[P(furyl)_3]_2$, $PdCl_2(PMePh_2)_2$, $PdCl_2[P(4-F-Ph)_3]_2$, $PdCl_2[P(C_6F_6)_3]_2$, $PdCl_2[P(2-COOH-Ph)(Ph)_2]_2$, and $PdCl_2[P(4-COOH-Ph)(Ph)_2]_2$. In some embodiments, the third catalyst is $Pd(dppf)Cl_2 \cdot CH_2Cl_2$.

In some embodiments of the process for preparing a compound of Formula I provided herein, the third strong base is selected from the group consisting of lithium hydroxide, sodium hydroxide, potassium hydroxide, rubidium hydroxide, cesium hydroxide, calcium hydroxide, strontium hydroxide, and barium hydroxide. In some embodiments, the third strong base is sodium hydroxide.

In some embodiments of the process for preparing a compound of Formula I provided herein, the first dealkylating agent is selected from the group consisting of Lewis acids and nucleophilic reagents. In some embodiments, the first dealkylating agent is selected from the group consisting of boron trihalides, organoboranes, triiodides, trialkylsilyl halides, hexafluorosilicate, aluminum trihalides, lithium halides, hydrogen halides, iron trihalides, tin tetrahalides, titanium tetrahalides, thiolates and amides. In some embodiments, the first dealkylating agent is a thiolate generated from dodecanethiol and sodium hydroxide.

In some embodiments of the process for preparing a compound of Formula I provided herein, the second diboronic acid or ester is selected from the group consisting of an alkenyl boronic acid, an alkyl boronic acid, an aryl boronic acid, a heteroaryl boronic acid, and a pinacol boronic ester. In some embodiments, the second diboronic acid or ester is bis(pinacolato)diboron.

In some embodiments of the process for preparing a compound of Formula I provided herein, the metal of the fourth catalyst is selected from the group consisting of nickel, palladium, and platinum. In some embodiments, the fourth catalyst is a palladium catalyst selected from the group consisting of Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the fourth catalyst is Pd(dppf)Cl$_2$.CH$_2$Cl$_2$.

In some embodiments of the process for preparing a compound of Formula I provided herein, $R^9$ is boronic acid pinacol ester represented by the formula:

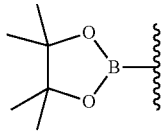 [SMILES: *B1OC(C)(C)C(C)(C)O1]

wherein the wavy line indicates the point of attachment to the pyridine ring of compound 32. In some embodiments of the process for preparing a compound of Formula I provided herein, the first oxidant is selected from the group consisting of O$_2$, N-methylmorpholine N-oxide (NMO), chloranil (CA), 7,7,8,8-tetracyanoquinodimethane (TCNQ), benzylidene-malononitrile (BMCN), tetracyanoethylene (TCNE), 2,3-dicyano-1,4-benzoquinone (DCBQ), and 2,3-dichloro-5,6-dicyano-1,4-benzoquinone (DDQ). In some embodiments, the first oxidant is NMO.

In some embodiments of the process for preparing a compound of Formula I provided herein, $R^6$ is boronic acid pinacol ester represented by the formula:

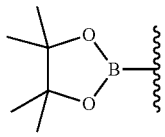 [SMILES: *B1OC(C)(C)C(C)(C)O1]

wherein the wavy line indicates the point of attachment to the pyridine ring of compound 12.

In some embodiments of the process for preparing a compound of Formula I provided herein, the metal of the eighth catalyst is selected from the group consisting of nickel, palladium, and platinum. In some embodiments, the eighth catalyst is a palladium catalyst selected from the group consisting of Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the eighth catalyst is Pd(dppf)Cl$_2$.CH$_2$Cl$_2$.

In some embodiments of the process for preparing a compound of Formula I provided herein, the metal of the sixth catalyst is selected from the group consisting of nickel, palladium, and platinum. In some embodiments, the sixth catalyst is a palladium catalyst selected from the group consisting of Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the sixth catalyst is Pd$_2$(dba)$_3$.

In some embodiments of the process for preparing a compound of Formula I provided herein, the second weak base is selected from the group consisting of a carbonate, a bicarbonate, methyl amine, ammonia, trimethyl ammonia, pyridine, and aniline. In some embodiments, the second weak base is cesium carbonate.

In some embodiments of the process for preparing a compound of Formula I provided herein, the third diboronic acid is selected from the group consisting of an alkenyl boronic acid, an alkyl boronic acid, an aryl boronic acid, a heteroaryl boronic acid, and a pinacol boronic ester.

In some embodiments, the third diboronic acid or ester is bis(pinacolato)diboron.

In some embodiments of the process for preparing a compound of Formula I provided herein, the metal of the seventh catalyst is selected from the group consisting of nickel, palladium, and platinum. In some embodiments, the seventh catalyst is a palladium catalyst selected from the group consisting of Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the seventh catalyst is Pd(dppf)Cl$_2$.CH$_2$Cl$_2$.

In some embodiments of the process for preparing a compound of Formula I provided herein, $R^8$ is boronic acid pinacol ester represented by the formula:

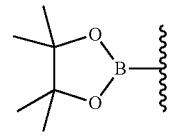

wherein the wavy line indicates the point of attachment to the pyridine ring of compound 30.

In some embodiments of the process for preparing a compound of Formula I provided herein, the fourth and fifth strong bases are each independently selected from the group consisting of lithium hydroxide, sodium hydroxide, potassium hydroxide, rubidium hydroxide, cesium hydroxide, calcium hydroxide, strontium hydroxide, and barium hydroxide. In some embodiments, the fourth strong base is sodium hydroxide. In some embodiments, the fifth strong base is sodium hydroxide.

In some embodiments of the process for preparing a compound of Formula I provided herein, $R^7$ is boronic acid pinacol ester represented by the formula:

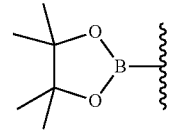

wherein the wavy line indicates the point of attachment to the pyridine ring of compound 28.

In some embodiments of the process for preparing a compound of Formula I provided herein, the metal of the fifth catalyst is selected from the group consisting of nickel, palladium, and platinum. In some embodiments, the fifth catalyst is a palladium catalyst selected from the group consisting of Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the fifth catalyst is Pd(dppf)Cl$_2$.CH$_2$Cl$_2$.

In some embodiments of the process for preparing a compound of Formula I provided herein, the second triflating reagent is selected from the group consisting of N-phenyl-bis(trifluoromethanesulfonimide), N-(5-chloro-2-pyridyl)triflimide, N-(2-pyridyl)triflimide, trifluoromethanesulfonic anhydride, a trialkylsilyl triflate, and a trialkylstannyl triflate. In some embodiments, the second triflating reagent is N-phenyl-bis(trifluoromethanesulfonimide).

In some embodiments of the process for preparing a compound of Formula I provided herein, the second dealkylating agent is selected from the group consisting of Lewis acids and nucleophilic reagents. In some embodiments, the second dealkylating agent is selected from the group consisting of boron trihalides, organoboranes, triiodides, trialkylsilyl halides, hexafluorosilicate, aluminum trihalides, lithium halides, hydrogen halides, iron trihalides, tin tetrahalides, titanium tetrahalides, thiolates and amides. In some embodiments, the second dealkylating agent is a thiolate generated from dodecanethiol and sodium hydroxide.

In some embodiments of the process for preparing a compound of Formula I provided herein, the first non-nucleophilic base is selected from the group consisting of triethylamine (TEA), diisopropylethylamine (DIPEA), N-methylmorpholine (NMM), tri-tert-butylpyrimidine (TTBP), 1,4-diazabicyclo-[2.2.2]octane (DABCO), 1,8-diazabicyclo[5.4.0]undec-7-ene (DBU), N,N-diethylaniline, pyridine, 2,6-lutidine, 2,4,6-collidine, 4-dimethylaminopyridine, quinuclidine, 2,6-di-tert-butylpyridine, tert-butylphosphazene, lithium diisopropylamide, sodium bis(trimethylsilyl)amide, potassium bis(trimethylsilyl)amide, lithium tetramethylpiperidide, sodium hydride, potassium hydride, sodium tert-butoxide, and potassium tert-butoxide. In some embodiments, the first non-nucleophilic base is DBU.

In some embodiments of the process for preparing a compound of Formula I provided herein, the acrylonitrile or acrylonitrile derivative is 2-chloroacrylonitrile.

In some embodiments of the process for preparing a compound of Formula I provided herein, the sixth strong base is selected from the group consisting of lithium hydroxide, sodium hydroxide, potassium hydroxide, rubidium hydroxide, cesium hydroxide, calcium hydroxide, strontium hydroxide, and barium hydroxide. In some embodiments, the sixth strong base is potassium hydroxide.

In some embodiments of the process for preparing a compound of Formula I provided herein, $R^3$ is boronic acid pinacol ester represented by the formula:

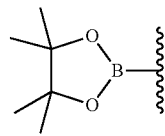

wherein the wavy line indicates the point of attachment to the pyridine ring of compound 24.

In some embodiments of the process for preparing a compound of Formula I provided herein, the metal of the ninth catalyst and the metal of the tenth catalyst are independently selected from the group consisting of nickel, palladium, and platinum. In some embodiments, the ninth catalyst is a palladium catalyst selected from the group consisting of Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the ninth catalyst is Pd(dppf)Cl$_2$.CH$_2$Cl$_2$. In some embodiments, the tenth catalyst is a palladium catalyst selected from the group consisting of Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the tenth catalyst is Pd(dbbf).

In some embodiments of the process for preparing a compound of Formula I provided herein, the fourth diboronic acid is selected from the group consisting of an alkenyl boronic acid, an alkyl boronic acid, an aryl boronic acid, a heteroaryl boronic acid, and a pinacol boronic ester.

In some embodiments, the fourth diboronic acid or ester is bis(pinacolato)diboron.

In some embodiments of the process for preparing a compound of Formula I provided herein, the seventh strong base is selected from the group consisting of lithium hydroxide, sodium hydroxide, potassium hydroxide, rubidium hydroxide, cesium hydroxide, calcium hydroxide, strontium hydroxide, and barium hydroxide. In some embodiments, the seventh strong base is sodium hydroxide.

In some embodiments of the process for preparing a compound of Formula I provided herein, the second non-nucleophilic base is selected from the group consisting of triethylamine (TEA), diisopropylethylamine (DIPEA), N-methylmorpholine (NMM), tri-tert-butylpyrimidine (TTBP), 1,4-diazabicyclo-[2.2.2]octane (DABCO), 1,8-diazabicyclo[5.4.0]undec-7-ene (DBU), N,N-diethylaniline, pyridine, 2,6-lutidine, 2,4,6-collidine, 4-dimethylaminopyridine, quinuclidine, 2,6-di-tert-butylpyridine, tert-butylphosphazene, lithium diisopropylamide, sodium bis(trimethylsilyl)amide, potassium bis(trimethylsilyl)amide, lithium tetramethylpiperidide, sodium hydride, potassium hydride, sodium tert-butoxide, and potassium tert-butoxide. In some embodiments, the second non-nucleophilic base is DIPEA.

In some embodiments of the process for preparing a compound of Formula I provided herein, the second oxidant is selected from the group consisting of O$_2$, N-methylmorpholine N-oxide (NMO), chloranil (CA), 7,7,8,8-tetracyanoquinodimethane (TCNQ), benzylidene-malononitrile (BMCN), tetracyanoethylene (TCNE), 2,3-dicyano-1,4-benzoquinone (DCBQ), and 2,3-dichloro-5,6-dicyano-1,4-benzoquinone (DDQ). In some embodiments, the second oxidant is DDQ.

In some embodiments of the process for preparing a compound of Formula I provided herein, the process further comprises mixing the compound of Formula I or a pharmaceutically acceptable salt thereof with a pharmaceutically acceptable carrier to form a pharmaceutical composition.

Also provided herein is a compound of formula 20a

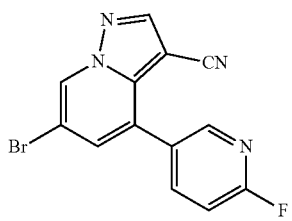

or pharmaceutically acceptable salt thereof.

Also provided herein is a compound of formula 25a

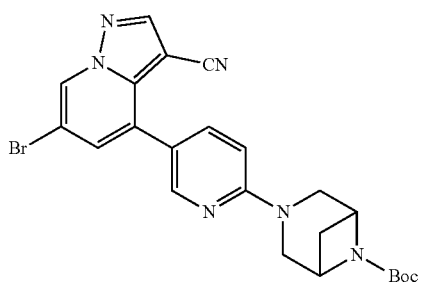

or pharmaceutically acceptable salt thereof.

Also provided herein is a compound of formula 26a

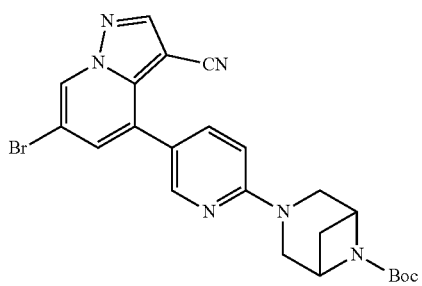

or pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and FIGURES, and from the claims.

DETAILED DESCRIPTION

Definitions

As used herein, "strong base" refers to a basic chemical compound that is able to deprotonate weak acids in an acid-base reaction. Examples of strong bases include, but are not limited to, hydroxides, alkoxides, and ammonia. Common examples of strong bases are the hydroxides of alkali metals and alkaline earth metals, e.g., NaOH. Certain strong bases are even able to deprotonate very weakly acidic C—H groups in the absence of water. Strong bases include, but are not limited to, sodium hydroxide, potassium hydroxide, barium hydroxide, cesium hydroxide, calcium hydroxide, strontium hydroxide, lithium hydroxide and rubidium hydroxide. In some embodiments, NaOH is used as the strong base. In some embodiments, potassium hydroxide is used as the strong base.

As used herein, the term "weak base" refers to inorganic and organic bases that are only partially ionized in aqueous solution. Weak bases typically have a pKa of between about 6 and about 11. A large number of such weak bases are known and are exemplified by those listed in the *Handbook of Biochemistry and Molecular Biology*, Vol. 1, 3rd ed., G. D. Fassman, CRC Press, 1976, pp. 305-347. The weak base can be soluble or insoluble in water. Suitable weak bases include, but are not limited to, alkali metal carbonates and bicarbonates, such as lithium carbonate, sodium carbonate, potassium carbonate, cesium carbonate, and sodium bicarbonate; ammonia; primary amines, such as methylamine; secondary amines; and tertiary amines, such as the trialkylamines, e.g., trimethylamine, triethylamine, tripropylamine and tributylamine, benzyldiethylamine, pyridine, quinoline, N-methylmorpholine, aniline, and the like.

"Non-nucleophilic base," as used herein, refers to a base that will not act as a nucleophile, i.e., a base that will not donate an electron pair to an electrophile to form a chemical bond in relation to a reaction. Typically, non-nucleophilic bases are bulky and sterically hindered, such that protons can attach to the basic center, but alkylation and complexation are prevented. Examples of non-nucleophilic bases include, but are not limited to, amines and nitrogen heterocycles, such as triethylamine and pyridine, amidines, lithium compounds, and phosphazenes. Other examples of non-nucleophilic bases include sodium hydride and potassium hydride.

As used herein, the term "amine protecting group" means any group known in the art of organic synthesis for the protection of amine groups. Such amine protecting groups include those listed in Greene, "Protective Groups in Organic Synthesis," John Wiley & Sons, New York (1981) and "The Peptides: Analysis, Synthesis, Biology, Vol. 3," Academic Press, New York (1981). Any amine protecting group known in the art can be used. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

The term "deprotecting agent" as used herein refers to a reagent or reagent system (reagent(s), and solvent) useful for removing a protecting group. Deprotecting agents can be acids, bases or reducing agents. For example, removal of the benzyl (Bn) group can be accomplished by reduction (hydrogenolysis), while removal of carbamates (e.g., Boc group) can be effected by use of acids (e.g., HCl, TFA, $H_2SO_4$, etc.), optionally with mild heating.

As used herein, the phrase "reducing agent" refers generically to any species capable of reducing another species while itself being oxidized. As used herein, the phrase "oxidizing agent" or "oxidant" refers generically to any species capable of oxidizing another species while itself being reduced.

As used herein, the term "triflating reagent" refers to a compound that is useful in a reaction in which a triflate group is attached to a hydroxy group to form a triflate ester. The triflating agent is the source of the trifluoroacetyl group. Triflating reagents include, but are not limited to, trialkylsilyl triflates, trialkylstannyl triflates, triflic anhydride (trifluoromethanesulfonic anhydride), N-phenyl-bis(trifluoromethanesulfonimide) ($PhNTf_2$), N-(5-chloro-2-pyridyl)triflimide, and N-(2-pyridyl)triflimide.

An "acrylonitrile derivative," as used herein, is a compound that is derived from acrylonitrile, which has the formula $CH_2CHCN$, where one or more of the hydrogen atoms have been replaced by another atom or group. An example of an acrylonitrile derivative is 2-chloroacrylonitrile, where one of the hydrogen atoms of acrylonitrile has been replaced by a chlorine atom.

As used herein, the term "dilute," when used with regard to an acid solution, refers to a solution having an acid concentration of less than about 0.1 N.

The terms "hydrogen" and "H" are used interchangeably herein.

The terms "halogen" or "halo" refer to fluorine (F), chlorine (Cl), bromine (Br), or iodine (I).

As used herein, the term "alkyl" refers to a hydrocarbon chain that can be a straight chain or branched chain, containing the indicated number of carbon atoms. For example, $C_{1-6}$ indicates that the group can have from 1 to 6 (inclusive) carbon atoms in it. Examples include methyl, ethyl, isopropyl, tert-butyl, and n-hexyl.

As used herein, the term "alkylamine" refers to an amine that contains one or more alkyl groups. An alkylamine can be a primary amine, a secondary amine or a tertiary amine. For example, a secondary alkylamine is an amine that contains two alkyl groups. An example includes diisopropylethylamine.

As used herein, the singular forms "a," "an," and "the" include plural referents unless the context clearly dictates otherwise.

As used herein, ranges and amounts can be expressed as "about" a particular value or range. About also includes the exact amount. Hence, "about 5 grams" means "about 5 grams" and also "5 grams." It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range including, but not limited to, 5.25, 6.5, 8.75 and 11.95 grams.

As used herein, "optional" or "optionally" means that the subsequently described event or circumstance does or does not occur and that the description includes instances where said event or circumstance occurs and instances where it does not. For example, a reaction mixture that "optionally includes a catalyst" means that the reaction mixture contains a catalyst or it does not contain a catalyst.

A salt can form from a compound in any manner familiar to the skilled artisan. Accordingly, the recitation "to form a compound or salt thereof" includes embodiments where a compound is formed and the salt is subsequently formed from the compound in a manner familiar to the skilled artisan.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

All combinations of the embodiments pertaining to the aspects described herein are specifically embraced by the present invention just as if each and every combination was individually explicitly recited, to the extent that such combinations embrace possible aspects. In addition, all sub-combinations of the embodiments contained within the aspects described herein, as well as all sub-combinations of the embodiments contained within all other aspects described herein, are also specifically embraced by the present invention just as if each and every sub-combination of all embodiments are explicitly recited herein.

Process for Preparing the Compound of Formula I

In some embodiments, provided herein is a process for preparing a compound of Formula I

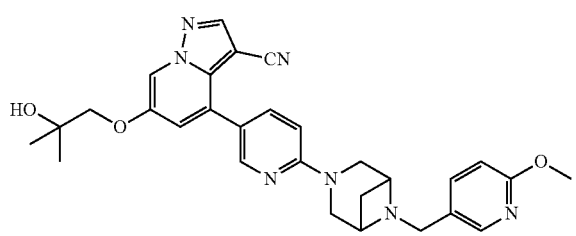

or a pharmaceutically acceptable salt thereof.

In some embodiments, the process of preparing a compound of Formula I or a pharmaceutically acceptable salt thereof comprises treating a compound of formula 16

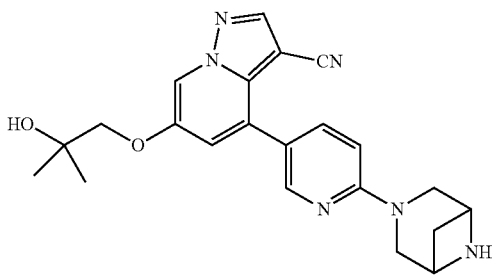

16 or a salt thereof with 6-methoxynicotinaldehyde and a reducing agent to form the compound of Formula I or a pharmaceutically acceptable salt thereof.

In some embodiments, the reducing agent is selected from an alkali metal borohydride, a hydrazine compound, citric acid, a citric acid salt, succinic acid, a succinic acid salt, ascorbic acid, and an ascorbic acid salt. In some embodiments, the reducing agent is selected from a sodium borohydride, a lithium borohydride, a nickel borohydride, and a potassium borohydride. In some embodiments, the lithium borohydride is selected from lithium borohydride and lithium triethylborohydride. In some embodiments, the sodium borohydride is selected from sodium triacetoxy borohydride (STAB), sodium borohydride, and sodium cyanoborohydride. In some embodiments, the reducing agent is STAB.

In some embodiments, the process further comprises preparing a compound of formula 16. In some embodiments, the process of preparing a compound of formula 16 includes treating a compound of formula 15

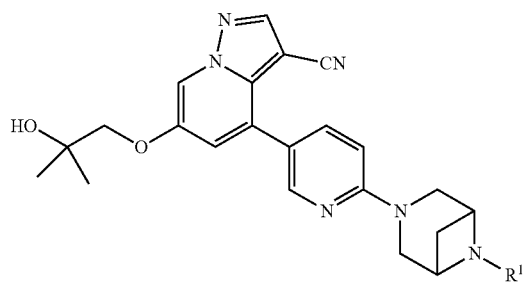

15 or a salt thereof, wherein R¹ is an amine protecting group, with a deprotecting agent to form the compound of formula 16 or a salt thereof.

In some embodiments, R¹ is an amine protecting group that is selected from formyl, acetyl, trifluoroacetyl, benzyl, benzoyl, carbamate, benzyloxycarbonyl, p-methoxybenzyl carbonyl, tert-butyloxycarbonyl (Boc), trimethylsilyl, 2-trimethylsilyl-ethanesulfonyl, trityl and substituted trityl groups, allyloxycarbonyl, 9-fluorenylmethyloxycarbonyl, nitroveratryloxycarbonyl, p-methoxybenzyl and tosyl. In some embodiments, R¹ is tert-butyloxycarbonyl (Boc).

In some embodiments, the deprotecting agent is selected from trifluoroacetic acid, hydrochloric acid, hydrobromic acid, hydriodic acid, phosphoric acid, sulfuric acid, methanesulfonic acid, p-toluene sulfonic acid, acetyl chloride, aluminum trichloride, and boron trifluoride. In some embodiments, the deprotecting agent is sulfuric acid. In some embodiments, the deprotecting agent is hydrochloric acid.

In some embodiments, provided herein is a process for preparing a compound of formula 15

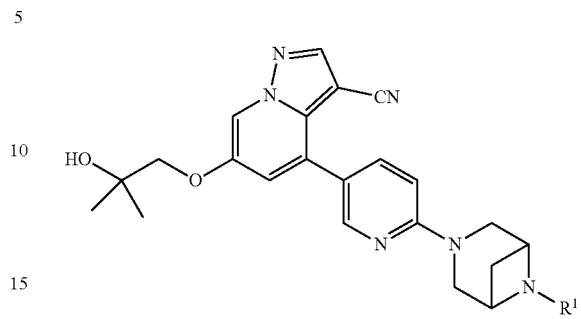

15 or a salt thereof, wherein R¹ is an amine protecting group.

In some embodiments, the process of preparing a compound of formula 15 comprises treating a compound of formula 13

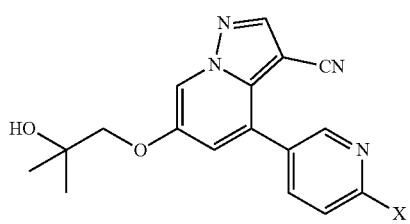

13 or a salt thereof, wherein X represents a halogen or a sulfonate, with a compound of formula 14

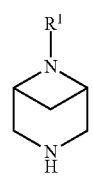

14 or a salt thereof, wherein R¹ is an amine protecting group, to form the compound of formula 15 or a salt thereof. In some embodiments, X is a halogen. For example, X is selected from the group consisting of F, Cl, Br, and I. In some embodiments, X is F. In some embodiments, X is a sulfonate. For example, X is selected from the group consisting of triflate, mesylate, and tosylate.

In some embodiments of preparing a compound of formula 15, R¹ is an amine protecting group that is selected from formyl, acetyl, trifluoroacetyl, benzyl, benzoyl, carbamate, benzyloxycarbonyl, p-methoxybenzyl carbonyl, tert-butyloxycarbonyl (Boc), trimethylsilyl, 2-trimethylsilyl-ethanesulfonyl, trityl and substituted trityl groups, allyloxycarbonyl, 9-fluorenylmethyloxycarbonyl, nitroveratryloxycarbonyl, p-methoxybenzyl and tosyl. In some embodiments, R¹ is tert-butyloxycarbonyl (Boc).

In some embodiments, the process further comprises preparing the compound of formula 13 or a salt thereof. In some embodiments, the process of preparing the compound of formula 13 or a salt thereof comprises treating a compound of formula 20

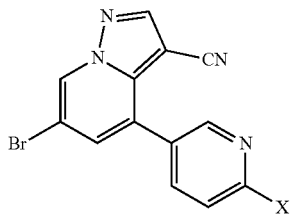

or a salt thereof, wherein X represents a halogen or a sulfonate, with a compound of formula 21

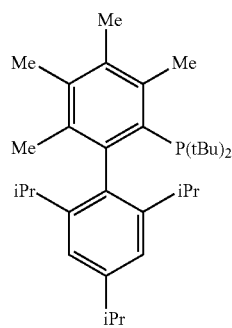

in the presence of 2,2-dimethyl dioxirane, a first catalyst comprising a metal, and a first weak base to form the compound of formula 13 or a salt thereof. In some embodiments, X is a halogen. For example, X is selected from the group consisting of F, Cl, Br, and I. In some embodiments, X is F. In some embodiments, X is a sulfonate. For example, X is selected from the group consisting of triflate, mesylate, and tosylate.

In some embodiments, the first catalyst comprising a metal can be a nickel catalyst, a palladium catalyst, or a platinum catalyst. In some embodiments, the catalyst is a nickel catalyst. Examples of nickel catalysts include, but are not limited to, Raney nickel, supported nickel catalysts, Ponder nickel catalysts, nickel alloys, dichlorobis(tributylphosphine)nickel(II), bis(tricyclohexylphosphine)nickel(II) dichloride, tetrakis(triphenylphosphite) nickel(0), Ni(COD)$_2$, Ni(PPh$_3$)$_4$, Ni(PPh$_3$)$_2$Cl$_2$, Ni(acac)$_2$, Cl$_2$Ni(PMe$_3$)$_2$, Cl$_2$Ni(PEt$_3$)$_2$, Cl$_2$Ni(Me$_2$PPh)$_2$, Cl$_2$Ni(MePPh$_2$)$_2$, and Cl$_2$Ni(Me$_2$PCH$_2$CH$_2$PMe$_2$). In some embodiments, the catalyst is a platinum catalyst. Examples of platinum catalysts include, but are not limited to, platinum carbonyl cyclovinylmethylsiloxane complexes, platinum divinyltetramethyldisiloxane complexes, platinum cyclovinylmethyl siloxane complexes, platinum octanaldehyde/octanol complexes, olefin complexes of platinum, olefin complexes of chloroplatinic acid, Karstedt's catalyst (Pt$_2$[[(CH$_2$=CH)(CH$_3$)$_2$Si]$_2$O]$_3$), Ashby's catalyst (Pt$_4$[CH$_2$=CHSi(CH$_3$)O]$_4$), a Lamoreaux catalyst (a Pt-octanal/octanol complex), platinic chloride, chloroplatinic acid, finely divided platinum metal ("platinum black"), platinum oxide, platinum metal on graphitized carbon, bis(acetylacetonato) platinum, ($\eta^5$-cyclopentadienyl)trialkylplatinum, finely divided platinum oxide, PtO$_2$ ("Adam's catalyst"), and chloroplatinic acid hexahydrate (Speier catalyst). In some embodiments, the catalyst is a palladium catalyst. In some embodiments, the first catalyst is a palladium catalyst selected from Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the first catalyst comprising a metal is Pd$_2$(dba)$_3$.

In some embodiments, the first weak base is selected from a carbonate, a bicarbonate, methyl amine, ammonia, trimethyl ammonia, pyridine, and aniline. Examples of carbonates include, but are not limited to, calcium carbonate, lithium carbonate, sodium carbonate, potassium carbonate, and cesium carbonate. Examples of bicarbonates include, but are not limited to, sodium bicarbonate, potassium bicarbonate, cesium bicarbonate, magnesium bicarbonate, calcium bicarbonate, and ammonium bicarbonate. In some embodiments, the first weak base is cesium carbonate (Cs$_2$CO$_3$).

In some embodiments, the process of preparing the compound of formula 13 or a salt thereof comprises treating a compound of formula 20 or a salt thereof with a first diboronic acid or ester in the presence of a second catalyst comprising a metal to form a compound of formula 22

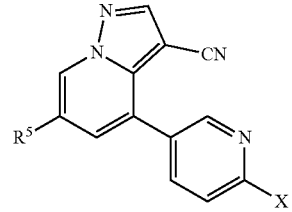

or a salt thereof, wherein X represents a halogen or a sulfonate and $R^5$ represents a boronic acid or ester with the boron atom as the point of attachment to the pyrazolopyridine ring of compound 22 or a salt thereof. In some embodiments, X is a halogen. For example, X is selected from the group consisting of F, Cl, Br, and I. In some embodiments, X is F. In some embodiments, X is a sulfonate. For example, X is selected from the group consisting of triflate, mesylate, and tosylate.

In some embodiments, the first diboronic acid or ester is selected from among an alkenyl boronic acid, an alkyl boronic acid, an aryl boronic acid, a heteroaryl boronic acid, and a pinacol boronic ester. In some embodiments, the first diboronic acid or ester is bis(pinacolato)diboron.

In some embodiments, the second catalyst comprising a metal can be a nickel catalyst, a palladium catalyst, or a platinum catalyst. In some embodiments, the catalyst is a nickel catalyst. Examples of nickel catalysts include, but are not limited to, Raney nickel, supported nickel catalysts, Ponder nickel catalysts, nickel alloys, dichlorobis(tributylphosphine)nickel(II), bis(tricyclohexylphosphine)nickel(II) dichloride, tetrakis(triphenylphosphite) nickel(0), Ni(COD)$_2$, Ni(PPh$_3$)$_4$, Ni(PPh$_3$)$_2$Cl$_2$, Ni(acac)$_2$, Cl$_2$Ni(PMe$_3$)$_2$, Cl$_2$Ni(PEt$_3$)$_2$, Cl$_2$Ni(Me$_2$PPh)$_2$, Cl$_2$Ni(MePPh$_2$)$_2$, and Cl$_2$Ni(Me$_2$PCH$_2$CH$_2$PMe$_2$). In some embodiments, the catalyst is a platinum catalyst. Examples of platinum catalysts include, but are not limited to, platinum carbonyl cyclovinylmethylsiloxane complexes, platinum divinyltetramethyldisiloxane complexes, platinum cyclovinylmethyl siloxane complexes, platinum octanaldehyde/octanol complexes, olefin complexes of platinum, olefin complexes of chloroplatinic acid, Karstedt's catalyst (Pt₂[[(CH₂=CH)(CH₃)₂Si]₂O]₃), Ashby's catalyst (Pt₄[CH₂=CHSi(CH₃)O]₄), a Lamoreaux catalyst (a Pt-octanal/octanol complex), platinic chloride, chloroplatinic acid, finely divided platinum metal ("platinum black"), platinum oxide, platinum metal on graphitized carbon, bis(acetylacetonato)platinum, (η⁵-cyclopentadienyl)trialkylplatinum, finely divided platinum oxide, PtO₂ ("Adam's catalyst"), and chloroplatinic acid hexahydrate (Speier catalyst). In some embodiments, the catalyst is a palladium catalyst. In some embodiments, the second catalyst is a palladium catalyst selected from Pd(dba)₂, PdCl₂, Pd(OAc)₂, Pd(dppf)Cl₂, Pd₂(dba)₃, PdCl₂(CH₃CN)₂, PdCl₂(PPh₃)₂, Pd(t-Bu)₃, Pd(dppf)Cl₂·CH₂Cl₂, Pd(PPh₃)₄, Pd(OAc)/PPh₃, PdCl₂[(Pet₃)]₂, Pd(DIPHOS)₂, PdCl₂(Bipy), [PdCl(Ph₂PCH₂PPh₂)]₂, PdCl₂[P(o-Tol)₃]₂, Pd₂(dba)₃/P(o-Tol)₃, Pd₂(dba)/P(furyl)₃, PdCl₂[P(furyl)₃]₂, PdCl₂(PMePh₂)₂, PdCl₂[P(4-F-Ph)₃]₂, PdCl₂[P(C₆F₆)₃]₂, PdCl₂[P(2-COOH-Ph)(Ph)₂]₂, and PdCl₂[P(4-COOH-Ph)(Ph)₂]₂. In some embodiments, the second catalyst comprising a metal is Pd(dppf)Cl₂·CH₂Cl₂.

In some embodiments, R⁵ is a boronic acid or ester. In some embodiments, the boronic acid or ester is selected from among an alkenyl boronic acid, an alkyl boronic acid, an aryl boronic acid, a heteroaryl boronic acid, and a pinacol boronic ester. In some embodiments, the diboronic acid or ester is boronic acid pinacol ester. In some embodiments, the boronic acid or ester is represented by the formula

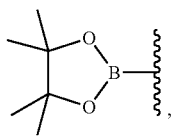

wherein the wavy line indicates the point of attachment to the pyrazolo[1,5-a]pyridine ring of compound 22 or salt thereof.

In some embodiments, R⁵ is boronic acid pinacol ester and compound 22 is compound 22a

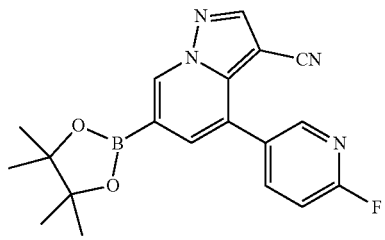

22a or salt thereof.

In some embodiments, the process of preparing a compound of formula 13 further comprises treating the compound of formula 22 or a salt thereof with a first strong base and hydrogen peroxide to form a compound of formula 23

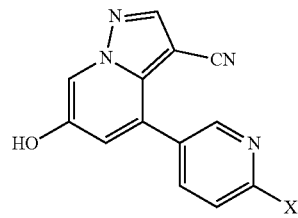

23 or a salt thereof, wherein X represents a halogen or a sulfonate. In some embodiments, X is a halogen. For example, X is selected from the group consisting of F, Cl, Br, and I. In some embodiments, X is F. In some embodiments, X is a sulfonate. For example, X is selected from the group consisting of triflate, mesylate, and tosylate.

In some embodiments, the first strong base is an alkali metal or alkaline earth metal hydroxide. For example, the first strong base is selected from lithium hydroxide, sodium hydroxide, potassium hydroxide, rubidium hydroxide, cesium hydroxide, calcium hydroxide, strontium hydroxide, and barium hydroxide. In some embodiments, the first strong base is sodium hydroxide.

In some embodiments, the process of preparing a compound of formula 13 further comprises treating the compound of formula 23 or a salt thereof with 2,2-dimethyloxirane in the presence of a second strong base to form the compound of formula 13 or a salt thereof.

In some embodiments, the second strong base is an alkali metal or alkaline earth metal hydroxide. For example, the first strong base is selected from lithium hydroxide, sodium hydroxide, potassium hydroxide, rubidium hydroxide, cesium hydroxide, calcium hydroxide, strontium hydroxide, and barium hydroxide. In some embodiments, the second strong base is sodium hydroxide.

In some embodiments, the process of preparing the compound of formula 13 or a salt thereof comprises treating a compound of formula 35

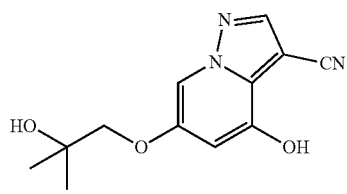

35 or a salt thereof with a first triflating reagent to form a compound of formula 36

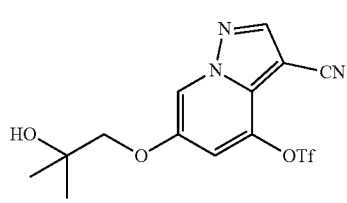

36 or a salt thereof.

In some embodiments, the first triflating reagent is selected from N-phenyl-bis(trifluoromethanesulfonimide), N-(5-chloro-2-pyridyl)triflimide, N-(2-pyridyl)triflimide, trifluoromethanesulfonic anhydride, a trialkylsilyl triflate, and a trialkylstannyl triflate. In some embodiments, the first triflating reagent is N-phenyl-bis(trifluoromethanesulfonimide).

In some embodiments, the process of preparing the compound of formula 13 or a salt thereof further comprises treating the compound of formula 36 or a salt thereof with a compound of formula 12

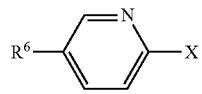

12 or a salt thereof, wherein X represents a halogen or a sulfonate and $R^6$ represents a boronic acid or ester with the boron atom as the point of attachment to the pyridine ring of compound 12, in the presence of a third catalyst comprising a metal to form the compound of formula 13 or a salt thereof. In some embodiments, X is a halogen or a sulfonate. For example, X is selected from the group consisting of F, Cl, Br, and I. In some embodiments, X is F. In some embodiments, X is a sulfonate. For example, X is selected from the group consisting of triflate, mesylate, and tosylate.

In some embodiments, $R^6$ is a boronic acid or ester. In some embodiments, the boronic acid or ester is boronic acid pinacol ester. In some embodiments, the boronic acid or ester is represented by the formula

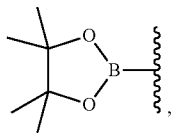 [SMILES: *B1OC(C)(C)C(C)(C)O1]

wherein the wavy line indicates the point of attachment to the pyridine ring of compound 12 or salt thereof.

In some embodiments, $R^6$ is boronic acid pinacol ester and compound 12 is compound 12a

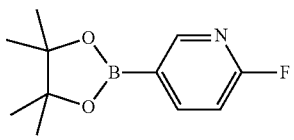

or salt thereof.

In some embodiments, the third catalyst comprising a metal can be a nickel catalyst, a palladium catalyst, or a platinum catalyst. In some embodiments, the catalyst is a nickel catalyst. Examples of nickel catalysts include, but are not limited to, Raney nickel, supported nickel catalysts, Ponder nickel catalysts, nickel alloys, dichlorobis(tributylphosphine)nickel(II), bis(tricyclohexylphosphine)nickel(II) dichloride, tetrakis(triphenylphosphite) nickel(0), Ni(COD)$_2$, Ni(PPh$_3$)$_4$, Ni(PPh$_3$)$_2$Cl$_2$, Ni(acac)$_2$, Cl$_2$Ni (PMe$_3$)$_2$, Cl$_2$Ni(PEt$_3$)$_2$, Cl$_2$Ni(Me$_2$PPh)$_2$, Cl$_2$Ni(MePPh$_2$)$_2$, and Cl$_2$Ni(Me$_2$PCH$_2$CH$_2$PMe$_2$). In some embodiments, the catalyst is a platinum catalyst. Examples of platinum catalysts include, but are not limited to, platinum carbonyl cyclovinylmethylsiloxane complexes, platinum divinyltetramethyldisiloxane complexes, platinum cyclovinylmethyl siloxane complexes, platinum octanaldehyde/octanol complexes, olefin complexes of platinum, olefin complexes of chloroplatinic acid, Karstedt's catalyst (Pt$_2$[[(CH$_2$=CH) (CH$_3$)$_2$Si]$_2$O]$_3$), Ashby's catalyst (Pt$_4$[CH$_2$=CHSi(CH$_3$)O]$_4$), a Lamoreaux catalyst (a Pt-octanal/octanol complex), platinic chloride, chloroplatinic acid, finely divided platinum metal ("platinum black"), platinum oxide, platinum metal on graphitized carbon, bis(acetylacetonato) platinum, ($\eta^5$-cyclopentadienyl)trialkylplatinum, finely divided platinum oxide, PtO$_2$ ("Adam's catalyst"), and chloroplatinic acid hexahydrate (Speier catalyst). In some embodiments, the catalyst is a palladium catalyst. In some embodiments, the palladium catalyst is selected from Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the third catalyst comprising a metal is Pd(dppf)Cl$_2$.CH$_2$Cl$_2$.

In some embodiments, the process of preparing the compound of formula 13 comprises preparing the compound of formula 35 or a salt thereof. In some embodiments, the process comprises treating a compound of formula 33

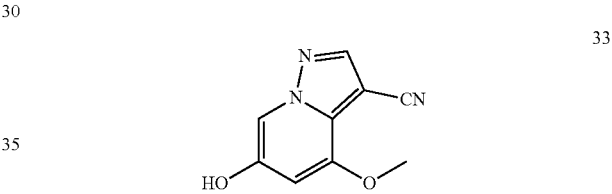

33 or a salt thereof with 2,2-dimethyloxirane in the presence of a third strong base to form the compound of formula 34

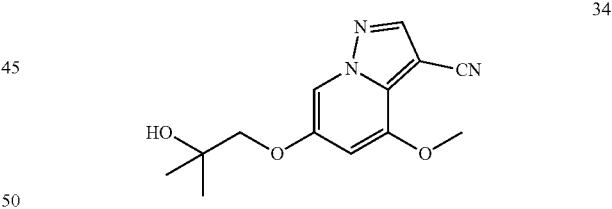

34 or a salt thereof.

In some embodiments, the third strong base is selected from lithium hydroxide, sodium hydroxide, potassium hydroxide, rubidium hydroxide, cesium hydroxide, calcium hydroxide, strontium hydroxide, and barium hydroxide. In some embodiments, the third strong base is sodium hydroxide.

In some embodiments, the process of preparing the compound of formula 35 or a salt thereof further comprises treating the compound of formula 34 or a salt thereof with a first dealkylating agent to form the compound of formula 35 or a salt thereof.

In some embodiments, the first dealkylating agent is selected from among Lewis acids and nucleophilic reagents. Examples of suitable Lewis acids include, but are not limited to, boron trihalides, organoboranes, triiodides, trialkylsilyl halides, hexafluorosilicate, aluminum trihalides, lithium halides, hydrogen halides, iron trihalides, tin tetrahalides, and titanium tetrahalides. In some embodiments, the Lewis acid is selected from among aluminum trichloride, boron tribromide, boron triiodide, lithium iodide, hydrogen bromide and trimethylsilyl iodide (TMSI). Examples of suitable nucleophilic reagents include, but are not limited to, thiolates and amides, such as lithium diisopropylamide (LDA) and sodium amide ($NaNH_2$). As used herein, the term "thiolate" refers to a thiol salt or thiol anion, which can be produced from a corresponding thiol by abstraction of a proton via a base. Any thiol can be used to form the thiolate, for example, any alkyl thiol, including, but not limited to propanethiols, butanethiols, pentanethiols, hexanethiols, heptanethiols, octanethiols, nonanethiols, decanethiols, undecanethiols, and dodecanethiols. In some embodiments, the thiol is dodecanethiol. In some embodiments, the base used to form the thiolate is a strong base, such as an alkali metal or alkaline earth metal hydroxide, for example, lithium hydroxide, sodium hydroxide, potassium hydroxide, rubidium hydroxide, cesium hydroxide, calcium hydroxide, strontium hydroxide, and barium hydroxide. In some embodiments, the strong base is sodium hydroxide. In some embodiments, the first dealkylating agent is a thiolate generated using dodecanethiol and sodium hydroxide.

In some embodiments, the process of preparing the compound of formula 13 further comprises preparing the compound of formula 33 or a salt thereof. In some embodiments, the process comprises treating a compound of formula A

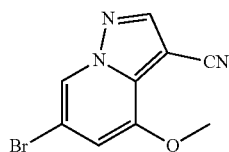

A or a salt thereof with a second diboronic acid or ester in the presence of a fourth catalyst comprising a metal to form a compound of formula 32

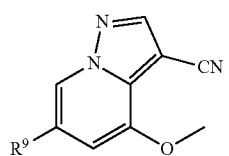

32 or a salt thereof, wherein $R^9$ represents a boronic acid or ester with the boron atom as the point of attachment to the pyrazolopyridine ring of compound 32 or a salt thereof.

In some embodiments, the second diboronic acid or ester is selected from among an alkenyl boronic acid, an alkyl boronic acid, an aryl boronic acid, a heteroaryl boronic acid, and a pinacol boronic ester. In some embodiments, the second diboronic acid or ester is bis(pinacolato)diboron.

In some embodiments, the fourth catalyst comprising a metal can be a nickel catalyst, a palladium catalyst, or a platinum catalyst. In some embodiments, the catalyst is a nickel catalyst. Examples of nickel catalysts include, but are not limited to, Raney nickel, supported nickel catalysts, Ponder nickel catalysts, nickel alloys, dichlorobis(tributylphosphine)nickel(II), bis(tricyclohexylphosphine)nickel(II) dichloride, tetrakis(triphenylphosphite) nickel(0), $Ni(COD)_2$, $Ni(PPh_3)_4$, $Ni(PPh_3)_2Cl_2$, $Ni(acac)_2$, $Cl_2Ni(PMe_3)_2$, $Cl_2Ni(PEt_3)_2$, $Cl_2Ni(Me_2PPh)_2$, $Cl_2Ni(MePPh_2)_2$, and $Cl_2Ni(Me_2PCH_2CH_2PMe_2)$. In some embodiments, the catalyst is a platinum catalyst. Examples of platinum catalysts include, but are not limited to, platinum carbonyl cyclovinylmethylsiloxane complexes, platinum divinyltetramethyldisiloxane complexes, platinum cyclovinylmethyl siloxane complexes, platinum octanaldehyde/octanol complexes, olefin complexes of platinum, olefin complexes of chloroplatinic acid, Karstedt's catalyst ($Pt_2[[(CH_2=CH)(CH_3)_2Si]_2O]_3$), Ashby's catalyst ($Pt_4[CH_2=CHSi(CH_3)O]_4$), a Lamoreaux catalyst (a Pt-octanal/octanol complex), platinic chloride, chloroplatinic acid, finely divided platinum metal ("platinum black"), platinum oxide, platinum metal on graphitized carbon, bis(acetylacetonato) platinum, ($\eta^5$-cyclopentadienyl)trialkylplatinum, finely divided platinum oxide, $PtO_2$ ("Adam's catalyst"), and chloroplatinic acid hexahydrate (Speier catalyst). In some embodiments, the catalyst is a palladium catalyst. In some embodiments, the fourth catalyst is a palladium catalyst selected from $Pd(dba)_2$, $PdCl_2$, $Pd(OAc)_2$, $Pd(dppf)Cl_2$, $Pd_2(dba)_3$, $PdCl_2(CH_3CN)_2$, $PdCl_2(PPh_3)_2$, $Pd(t-Bu)_3$, $Pd(dppf)Cl_2.CH_2Cl_2$, $Pd(PPh_3)_4$, $Pd(OAc)/PPh_3$, $PdCl_2[(Pet_3)]_2$, $Pd(DIPHOS)_2$, $PdCl_2(Bipy)$, $[PdCl(Ph_2PCH_2PPh_2)]_2$, $PdCl_2[P(o-Tol)_3]_2$, $Pd_2(dba)_3/P(o-Tol)_3$, $Pd_2(dba)/P(furyl)_3$, $PdCl_2[P(furyl)_3]_2$, $PdCl_2(PMePh_2)_2$, $PdCl_2[P(4-F-Ph)_3]_2$, $PdCl_2[P(C_6F_6)_3]_2$, $PdCl_2[P(2-COOH-Ph)(Ph)_2]_2$, and $PdCl_2[P(4-COOH-Ph)(Ph)_2]_2$. In some embodiments, the fourth catalyst comprising a metal is $Pd(dppf)Cl_2.CH_2Cl_2$.

In some embodiments, $R^9$ is a boronic acid or ester. In some embodiments, the boronic acid or ester is selected from among an alkenyl boronic acid, an alkyl boronic acid, an aryl boronic acid, a heteroaryl boronic acid, and a pinacol boronic ester. In some embodiments, the diboronic acid or ester is boronic acid pinacol ester. In some embodiments, the boronic acid or ester is represented by the formula

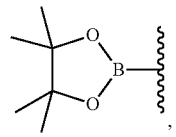 [SMILES: *B1OC(C)(C)C(C)(C)O1]

wherein the wavy line indicates the point of attachment to the pyrazolo[1,5-a]pyridine ring of compound 32 or salt thereof.

In some embodiments, $R^9$ is boronic acid pinacol ester and compound 32 is compound 32a

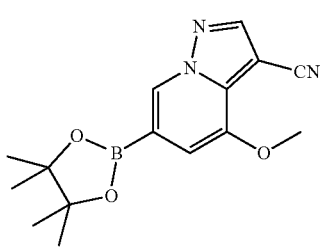

32a or salt thereof.

In some embodiments, the process of preparing a compound of formula 33 further comprises treating the compound of formula 32 or a salt thereof with a first oxidant to form the compound of formula 33 or a salt thereof.

In some embodiments, the first oxidant is selected from O$_2$, N-methylmorpholine N-oxide (NMO), chloranil (CA), 7,7,8,8-tetracyanoquinodimethane (TCNQ), benzylidenemalononitrile (BMCN), tetracyanoethylene (TCNE), 2,3-dicyano-1,4-benzoquinone (DCBQ), and 2,3-dichloro-5,6-dicyano-1,4-benzoquinone (DDQ). In some embodiments, the first oxidant is NMO.

In some embodiments, the process of preparing the compound of Formula I or a pharmaceutically acceptable salt thereof further comprises preparing the compound of formula 20 or a salt thereof. In some embodiments, the process comprises treating a compound of formula A

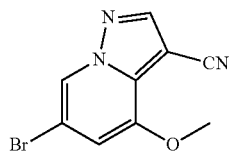

A or a salt thereof with a second dealkylating agent to form a compound of formula 18

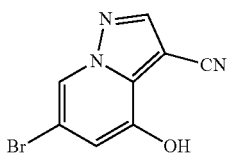

18 or a salt thereof.

In some embodiments, the second dealkylating agent is selected from among Lewis acids and nucleophilic reagents. Examples of suitable Lewis acids include, but are not limited to, boron trihalides, organoboranes, triiodides, trialkylsilyl halides, hexafluorosilicate, aluminum trihalides, lithium halides, hydrogen halides, iron trihalides, tin tetrahalides, and titanium tetrahalides. In some embodiments, the Lewis acid is selected from among aluminum trichloride, boron tribromide, boron triiodide, lithium iodide, hydrogen bromide and trimethylsilyl iodide (TMSI). Examples of suitable nucleophilic reagents include, but are not limited to, thiolates and amides, such as lithium diisopropylamide (LDA) and sodium amide (NaNH$_2$). As used herein, the term "thiolate" refers to a thiol salt or thiol anion, which can be produced from a corresponding thiol by abstraction of a proton via a base. Any thiol can be used to form the thiolate, for example, any alkyl thiol, including, but not limited to propanethiols, butanethiols, pentanethiols, hexanethiols, heptanethiols, octanethiols, nonanethiols, decanethiols, undecanethiols, and dodecanethiols. In some embodiments, the thiol is dodecanethiol. In some embodiments, the base used to form the thiolate is a strong base, such as an alkali metal or alkaline earth metal hydroxide, for example, lithium hydroxide, sodium hydroxide, potassium hydroxide, rubidium hydroxide, cesium hydroxide, calcium hydroxide, strontium hydroxide, and barium hydroxide. In some embodiments, the strong base is sodium hydroxide. In some embodiments, the second dealkylating agent is a thiolate generated using dodecanethiol and sodium hydroxide.

In some embodiments, the process of preparing the compound of Formula I or a pharmaceutically acceptable salt thereof further comprises treating the compound of formula 18 or a salt thereof with a second triflating reagent to form a compound of formula 19

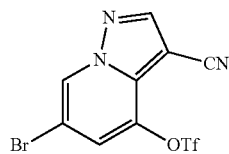

19 or a salt thereof.

In some embodiments, the second triflating reagent is selected from N-phenyl-bis(trifluoromethanesulfonimide), N-(5-chloro-2-pyridyl)triflimide, N-(2-pyridyl)triflimide, trifluoromethanesulfonic anhydride, a trialkylsilyl triflate, and a trialkylstannyl triflate. In some embodiments, the second triflating reagent is N-phenyl-bis(trifluoromethanesulfonimide).

In some embodiments, the process of preparing the compound of Formula I or a pharmaceutically acceptable salt thereof further comprises treating the compound of formula 19 or a salt thereof with a compound of formula 28

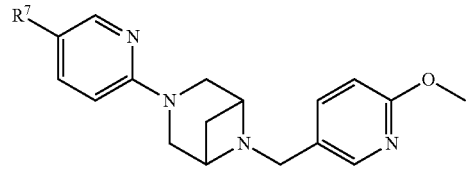

28 or a salt thereof, wherein R$^7$ represents a boronic acid or ester with the boron atom as the point of attachment to the pyridine ring of compound 28, in the presence of a fifth catalyst comprising a metal to form a compound of formula 29

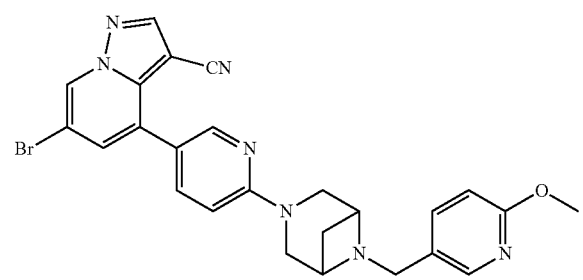

29 or a salt thereof.

In some embodiments, R$^7$ is a boronic acid or ester. In some embodiments, the boronic acid or ester is selected from among an alkenyl boronic acid, an alkyl boronic acid, an aryl boronic acid, a heteroaryl boronic acid, and a pinacol boronic ester. In some embodiments, the diboronic acid or ester is boronic acid pinacol ester. In some embodiments, the boronic acid or ester is represented by the formula

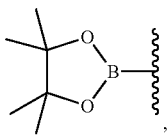

wherein the wavy line indicates the point of attachment to the pyridine ring of compound 28 or salt thereof.

In some embodiments, $R^7$ is boronic acid pinacol ester and compound 28 is compound 28a

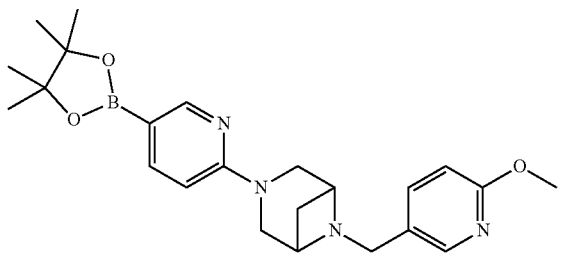

In some embodiments, the fifth catalyst comprising a metal can be a nickel catalyst, a palladium catalyst, or a platinum catalyst. In some embodiments, the catalyst is a nickel catalyst. Examples of nickel catalysts include, but are not limited to, Raney nickel, supported nickel catalysts, Ponder nickel catalysts, nickel alloys, dichlorobis(tributyl-phosphine)nickel(II), bis(tricyclohexylphosphine)nickel(II) dichloride, tetrakis(triphenylphosphite) nickel(0), Ni(COD)$_2$, Ni(PPh$_3$)$_4$, Ni(PPh$_3$)$_2$Cl$_2$, Ni(acac)$_2$, Cl$_2$Ni(PMe$_3$)$_2$, Cl$_2$Ni(PEt$_3$)$_2$, Cl$_2$Ni(Me$_2$PPh)$_2$, Cl$_2$Ni(MePPh$_2$)$_2$, and Cl$_2$Ni(Me$_2$PCH$_2$CH$_2$PMe$_2$). In some embodiments, the catalyst is a platinum catalyst. Examples of platinum catalysts include, but are not limited to, platinum carbonyl cyclovinylmethylsiloxane complexes, platinum divinylte-tramethyldisiloxane complexes, platinum cyclovinylmethyl siloxane complexes, platinum octanaldehyde/octanol complexes, olefin complexes of platinum, olefin complexes of chloroplatinic acid, Karstedt's catalyst (Pt$_2$[[(CH$_2$=CH)(CH$_3$)$_2$Si]$_2$O]$_3$), Ashby's catalyst (Pt$_4$[CH$_2$=CHSi(CH$_3$)O]$_4$), a Lamoreaux catalyst (a Pt-octanal/octanol complex), platinic chloride, chloroplatinic acid, finely divided platinum metal ("platinum black"), platinum oxide, platinum metal on graphitized carbon, bis(acetylacetonato) platinum, ($\eta^5$-cyclopentadienyl)trialkylplatinum, finely divided platinum oxide, PtO$_2$ ("Adam's catalyst"), and chloroplatinic acid hexahydrate (Speier catalyst). In some embodiments, the catalyst is a palladium catalyst. In some embodiments, the palladium catalyst is selected from Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the fifth catalyst comprising a metal is Pd(dppf)Cl$_2$.CH$_2$Cl$_2$.

In some embodiments, the process of preparing the compound of Formula I or a pharmaceutically acceptable salt thereof or a pharmaceutically acceptable salt thereof further comprises treating the compound of formula 29 or a salt thereof with a compound of formula 21

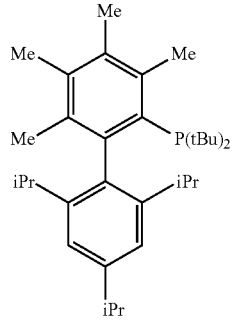

in the presence of 2,2-dimethyl dioxirane, a sixth catalyst comprising a metal, and a second weak base to form the compound of Formula I or a pharmaceutically acceptable salt thereof.

In some embodiments, the sixth catalyst comprising a metal can be a nickel catalyst, a palladium catalyst, or a platinum catalyst. In some embodiments, the catalyst is a nickel catalyst. Examples of nickel catalysts include, but are not limited to, Raney nickel, supported nickel catalysts, Ponder nickel catalysts, nickel alloys, dichlorobis(tributyl-phosphine)nickel(II), bis(tricyclohexylphosphine)nickel(II) dichloride, tetrakis(triphenylphosphite) nickel(0), Ni(COD)$_2$, Ni(PPh$_3$)$_4$, Ni(PPh$_3$)$_2$Cl$_2$, Ni(acac)$_2$, Cl$_2$Ni(PMe$_3$)$_2$, Cl$_2$Ni(PEt$_3$)$_2$, Cl$_2$Ni(Me$_2$PPh)$_2$, Cl$_2$Ni(MePPh$_2$)$_2$, and Cl$_2$Ni(Me$_2$PCH$_2$CH$_2$PMe$_2$). In some embodiments, the catalyst is a platinum catalyst. Examples of platinum catalysts include, but are not limited to, platinum carbonyl cyclovinylmethylsiloxane complexes, platinum divinylte-tramethyldisiloxane complexes, platinum cyclovinylmethyl siloxane complexes, platinum octanaldehyde/octanol complexes, olefin complexes of platinum, olefin complexes of chloroplatinic acid, Karstedt's catalyst (Pt$_2$[[(CH$_2$=CH)(CH$_3$)$_2$Si]$_2$O]$_3$), Ashby's catalyst (Pt$_4$[CH$_2$=CHSi(CH$_3$)O]$_4$), a Lamoreaux catalyst (a Pt-octanal/octanol complex), platinic chloride, chloroplatinic acid, finely divided platinum metal ("platinum black"), platinum oxide, platinum metal on graphitized carbon, bis(acetylacetonato) platinum, ($\eta^5$-cyclopentadienyl)trialkylplatinum, finely divided platinum oxide, PtO$_2$ ("Adam's catalyst"), and chloroplatinic acid hexahydrate (Speier catalyst). In some embodiments, the catalyst is a palladium catalyst. In some embodiments, the sixth catalyst is a palladium catalyst selected from Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the sixth catalyst comprising a metal is Pd$_2$(dba)$_3$.

In some embodiments, the second weak base is selected from a carbonate, a bicarbonate, methyl amine, ammonia, trimethyl ammonia, pyridine, and aniline. Examples of carbonates include, but are not limited to, calcium carbonate, lithium carbonate, sodium carbonate, potassium carbonate, and cesium carbonate. Examples of bicarbonates include, but are not limited to, sodium bicarbonate, potassium bicarbonate, cesium bicarbonate, magnesium bicarbonate, calcium bicarbonate, and ammonium bicarbonate. In some embodiments, the second weak base is cesium carbonate (Cs$_2$CO$_3$).

In some embodiments, the process of preparing the compound of Formula I or a pharmaceutically acceptable salt thereof comprises treating a compound of formula 29 or a salt thereof with a third diboronic acid or ester in the presence of a seventh catalyst comprising a metal to form a compound of formula 30

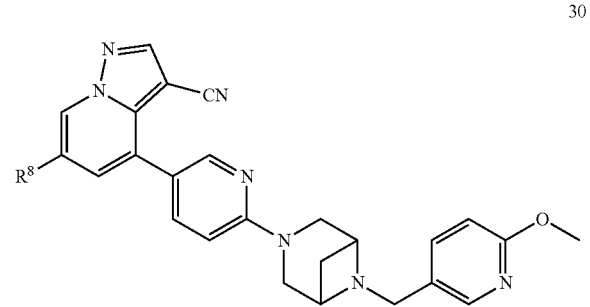

30 or a salt thereof, wherein R$^8$ represents a boronic acid or ester with the boron atom as the point of attachment to the pyrazolopyridine ring of compound 30 or a salt thereof.

In some embodiments, the third diboronic acid or ester is selected from among an alkenyl boronic acid, an alkyl boronic acid, an aryl boronic acid, a heteroaryl boronic acid, and a pinacol boronic ester. In some embodiments, the third diboronic acid or ester is bis(pinacolato)diboron.

In some embodiments, the seventh catalyst comprising a metal can be a nickel catalyst, a palladium catalyst, or a platinum catalyst. In some embodiments, the catalyst is a nickel catalyst. Examples of nickel catalysts include, but are not limited to, Raney nickel, supported nickel catalysts, Ponder nickel catalysts, nickel alloys, dichlorobis(tributylphosphine)nickel(II), bis(tricyclohexylphosphine)nickel(II) dichloride, tetrakis(triphenylphosphite) nickel(0), Ni(COD)$_2$, Ni(PPh$_3$)$_4$, Ni(PPh$_3$)$_2$Cl$_2$, Ni(acac)$_2$, Cl$_2$Ni (PMe$_3$)$_2$, Cl$_2$Ni(PEt$_3$)$_2$, Cl$_2$Ni(Me$_2$PPh)$_2$, Cl$_2$Ni(MePPh$_2$)$_2$, and Cl$_2$Ni(Me$_2$PCH$_2$CH$_2$PMe$_2$). In some embodiments, the catalyst is a platinum catalyst. Examples of platinum catalysts include, but are not limited to, platinum carbonyl cyclovinylmethylsiloxane complexes, platinum divinyltetramethyldisiloxane complexes, platinum cyclovinylmethyl siloxane complexes, platinum octanaldehyde/octanol complexes, olefin complexes of platinum, olefin complexes of chloroplatinic acid, Karstedt's catalyst (Pt$_2$[[(CH$_2$=CH)(CH$_3$)$_2$Si]$_2$O]$_3$), Ashby's catalyst (Pt$_4$[CH$_2$=CHSi(CH$_3$)O]$_4$), a Lamoreaux catalyst (a Pt-octanal/octanol complex), platinic chloride, chloroplatinic acid, finely divided platinum metal ("platinum black"), platinum oxide, platinum metal on graphitized carbon, bis(acetylacetonato) platinum, ($\eta^5$-cyclopentadienyl)trialkylplatinum, finely divided platinum oxide, PtO$_2$ ("Adam's catalyst"), and chloroplatinic acid hexahydrate (Speier catalyst). In some embodiments, the catalyst is a palladium catalyst. In some embodiments, the seventh catalyst is a palladium catalyst selected from Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf) Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$ [P(o-Tol)$_3$]$_2$, Pd$_2$(dba)$_3$/P(o-Tol)$_3$, Pd$_2$(dba)/P(furyl)$_3$, PdCl$_2$ [P(furyl)$_3$]$_2$, PdCl$_2$(PMePh$_2$)$_2$, PdCl$_2$[P(4-F-Ph)$_3$]$_2$, PdCl$_2$[P (C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the seventh catalyst comprising a metal is Pd(dppf)Cl$_2$.CH$_2$Cl$_2$.

In some embodiments, R$^8$ is a boronic acid or ester. In some embodiments, the boronic acid or ester is selected from among an alkenyl boronic acid, an alkyl boronic acid, an aryl boronic acid, a heteroaryl boronic acid, and a pinacol boronic ester. In some embodiments, the diboronic acid or ester is boronic acid pinacol ester. In some embodiments, the boronic acid or ester is represented by the formula

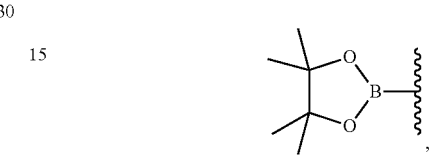

wherein the wavy line indicates the point of attachment to the pyridine ring of compound 30 or salt thereof.

In some embodiments, R$^8$ is boronic acid pinacol ester and compound 30 is compound 30a

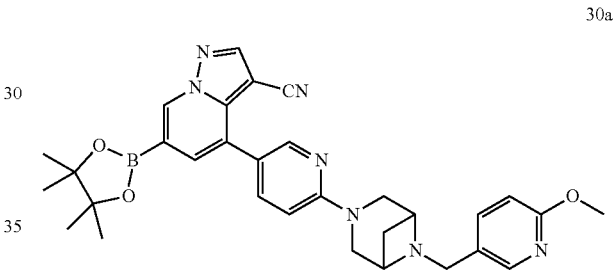

30a or salt thereof.

In some embodiments, the process of preparing the compound of Formula I or a pharmaceutically acceptable salt thereof further comprises treating the compound of formula 30 or a salt thereof with a fourth strong base and hydrogen peroxide to form a compound of formula

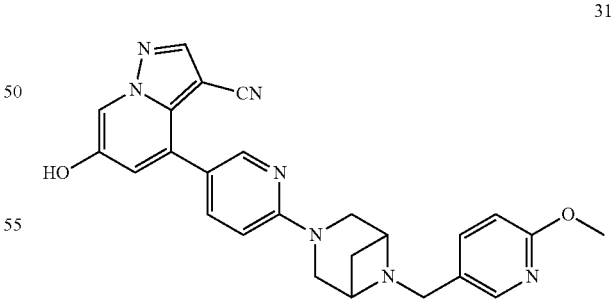

31 or a salt thereof.

In some embodiments, the fourth strong base is an alkali metal or alkaline earth metal hydroxide. For example, the fourth strong base is selected from lithium hydroxide, sodium hydroxide, potassium hydroxide, rubidium hydroxide, cesium hydroxide, calcium hydroxide, strontium hydroxide, and barium hydroxide. In some embodiments, the fourth strong base is sodium hydroxide.

In some embodiments, the process of preparing the compound of Formula I or a pharmaceutically acceptable salt thereof further comprises treating the compound of formula 31 or a salt thereof with 2,2-dimethyloxirane in the presence of a fifth strong base to form the compound of Formula I or a pharmaceutically acceptable salt thereof.

In some embodiments, the fifth strong base is an alkali metal or alkaline earth metal hydroxide. For example, the fifth strong base is selected from lithium hydroxide, sodium hydroxide, potassium hydroxide, rubidium hydroxide, cesium hydroxide, calcium hydroxide, strontium hydroxide, and barium hydroxide. In some embodiments, the fifth strong base is sodium hydroxide.

In some embodiments, the process of preparing the compound of Formula I or a pharmaceutically acceptable salt thereof further comprises treating the compound of formula 19 or a salt thereof with a compound of formula 12

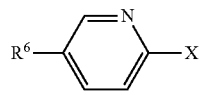

12 or a salt thereof, wherein X represents a halogen or a sulfonate and $R^6$ represents a boronic acid or ester with the boron atom as the point of attachment to the pyridine ring of compound 12, in the presence of a eighth catalyst comprising a metal to form the compound of formula 20 or a salt thereof. In some embodiments, X is a halogen or a sulfonate. For example, X is selected from the group consisting of F, Cl, Br, and I. In some embodiments, X is F. In some embodiments, X is a sulfonate. For example, X is selected from the group consisting of triflate, mesylate, and tosylate.

In some embodiments, $R^6$ is a boronic acid or ester. In some embodiments, the boronic acid or ester is boronic acid pinacol ester. In some embodiments, the boronic acid or ester is represented by the formula

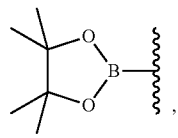

wherein the wavy line indicates the point of attachment to the pyridine ring of compound 12 or salt thereof.

In some embodiments, $R^6$ is boronic acid pinacol ester and compound 12 is compound 12a

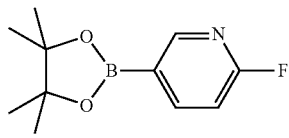

12a or salt thereof.

In some embodiments, the eighth catalyst comprising a metal can be a nickel catalyst, a palladium catalyst, or a platinum catalyst. In some embodiments, the catalyst is a nickel catalyst. Examples of nickel catalysts include, but are not limited to, Raney nickel, supported nickel catalysts, Ponder nickel catalysts, nickel alloys, dichlorobis(tributylphosphine)nickel(II), bis(tricyclohexylphosphine)nickel(II) dichloride, tetrakis(triphenylphosphite) nickel(0), Ni(COD)$_2$, Ni(PPh$_3$)$_4$, Ni(PPh$_3$)$_2$Cl$_2$, Ni(acac)$_2$, Cl$_2$Ni(PMe$_3$)$_2$, Cl$_2$Ni(PEt$_3$)$_2$, Cl$_2$Ni(Me$_2$PPh)$_2$, Cl$_2$Ni(MePPh$_2$)$_2$, and Cl$_2$Ni(Me$_2$PCH$_2$CH$_2$PMe$_2$). In some embodiments, the catalyst is a platinum catalyst. Examples of platinum catalysts include, but are not limited to, platinum carbonyl cyclovinylmethylsiloxane complexes, platinum divinyltetramethyldisiloxane complexes, platinum cyclovinylmethyl siloxane complexes, platinum octanaldehyde/octanol complexes, olefin complexes of platinum, olefin complexes of chloroplatinic acid, Karstedt's catalyst (Pt$_2$[[(CH$_2$=CH)(CH$_3$)$_2$Si]$_2$O]$_3$), Ashby's catalyst (Pt$_4$[CH$_2$=CHSi(CH$_3$)O]$_4$), a Lamoreaux catalyst (a Pt-octanal/octanol complex), platinic chloride, chloroplatinic acid, finely divided platinum metal ("platinum black"), platinum oxide, platinum metal on graphitized carbon, bis(acetylacetonato) platinum, (q-cyclopentadienyl)trialkylplatinum, finely divided platinum oxide, PtO$_2$ ("Adam's catalyst"), and chloroplatinic acid hexahydrate (Speier catalyst). In some embodiments, the catalyst is a palladium catalyst. In some embodiments, the palladium catalyst is selected from Pd(dba)$_2$, PdCl$_2$, Pd(OAc)$_2$, Pd(dppf)Cl$_2$, Pd$_2$(dba)$_3$, PdCl$_2$(CH$_3$CN)$_2$, PdCl$_2$(PPh$_3$)$_2$, Pd(t-Bu)$_3$, Pd(dppf)Cl$_2$.CH$_2$Cl$_2$, Pd(PPh$_3$)$_4$, Pd(OAc)/PPh$_3$, PdCl$_2$[(Pet$_3$)]$_2$, Pd(DIPHOS)$_2$, PdCl$_2$(Bipy), [PdCl(Ph$_2$PCH$_2$PPh$_2$)]$_2$, PdCl$_2$[P(o-Tol)$_3$]$_2$, Pd$_2$(dba)$_3$/P(o-Tol)$_3$, Pd$_2$(dba)/P(furyl)$_3$, PdCl$_2$[P(furyl)$_3$]$_2$, PdCl$_2$(PMePh$_2$)$_2$, PdCl$_2$[P(4-F-Ph)$_3$]$_2$, PdCl$_2$[P(C$_6$F$_6$)$_3$]$_2$, PdCl$_2$[P(2-COOH-Ph)(Ph)$_2$]$_2$, and PdCl$_2$[P(4-COOH-Ph)(Ph)$_2$]$_2$. In some embodiments, the eighth catalyst comprising a metal is Pd(dppf)Cl$_2$.CH$_2$Cl$_2$.

In some embodiments, provided herein is a process for preparing a compound of formula 15

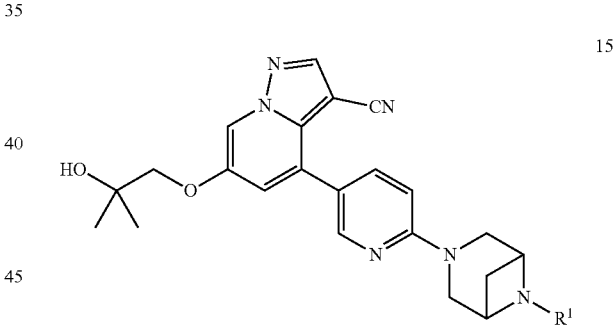

15 or a salt thereof, wherein $R^1$ is an amine protecting group.

In some embodiments, the process for preparing the compound of formula 15 or a salt thereof comprises treating a compound of formula 26

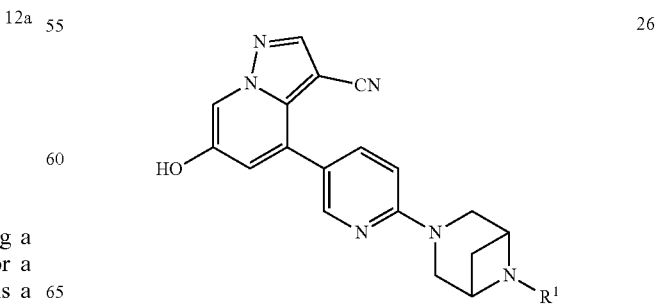

26 or a salt thereof, wherein R¹ is an amine protecting group, with 2,2-dimethyloxirane in the presence of a sixth strong base to form the compound of formula 15 or a salt thereof.

In some embodiments, R¹ is an amine protecting group that is selected from formyl, acetyl, trifluoroacetyl, benzyl, benzoyl, carbamate, benzyloxycarbonyl, p-methoxybenzyl carbonyl, tert-butyloxycarbonyl (Boc), trimethylsilyl, 2-trimethylsilyl-ethanesulfonyl, trityl and substituted trityl groups, allyloxycarbonyl, 9-fluorenylmethyloxycarbonyl, nitroveratryloxycarbonyl, p-methoxybenzyl and tosyl. In some embodiments, R¹ is tert-butyloxycarbonyl (Boc).

In some embodiments, the sixth strong base is selected from lithium hydroxide, sodium hydroxide, potassium hydroxide, rubidium hydroxide, cesium hydroxide, calcium hydroxide, strontium hydroxide, and barium hydroxide. In some embodiments, the sixth strong base is potassium hydroxide.

In some embodiments, the process of preparing the compound of Formula I or a pharmaceutically acceptable salt thereof further comprises preparing the compound of formula 26 or a salt thereof. In some embodiments, the process comprises treating a compound of formula B

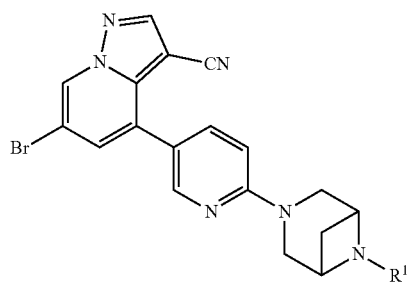

or a salt thereof with a compound of formula 24

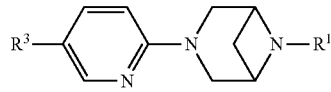

or a salt thereof, wherein R¹ is an amine protecting group and R³ represents a boronic acid or ester with the boron atom as the point of attachment to the pyridine ring of compound 24, in the presence of a ninth catalyst comprising a metal to form a compound of formula 25

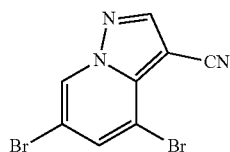

or a salt thereof.

In some embodiments, R¹ is an amine protecting group that is selected from formyl, acetyl, trifluoroacetyl, benzyl, benzoyl, carbamate, benzyloxycarbonyl, p-methoxybenzyl carbonyl, tert-butyloxycarbonyl (Boc), trimethylsilyl, 2-trimethylsilyl-ethanesulfonyl, trityl and substituted trityl groups, allyloxycarbonyl, 9-fluorenylmethyloxycarbonyl, nitroveratryloxycarbonyl, p-methoxybenzyl and tosyl. In some embodiments, R¹ is tert-butyloxycarbonyl (Boc).

In some embodiments, R³ is a boronic acid or ester. In some embodiments, the boronic acid or ester is selected from among an alkenyl boronic acid, an alkyl boronic acid, an aryl boronic acid, a heteroaryl boronic acid, and a pinacol boronic ester. In some embodiments, the diboronic acid or ester is boronic acid pinacol ester. In some embodiments, the boronic acid or ester is represented by the formula

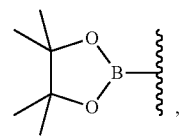

wherein the wavy line indicates the point of attachment to the pyridine ring of compound 24 or salt thereof.

In some embodiments, R¹ is Boc and R³ is boronic acid pinacol ester and compound 24 is compound 24a

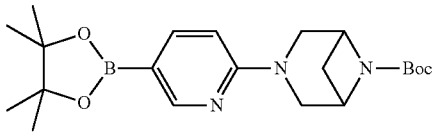

or salt thereof.

In some embodiments, R¹ is Boc and compound 25 is compound 25a

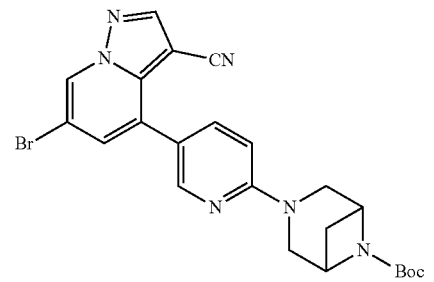

or salt thereof.

In some embodiments, the ninth catalyst comprising a metal can be a nickel catalyst, a palladium catalyst, or a platinum catalyst. In some embodiments, the catalyst is a nickel catalyst. Examples of nickel catalysts include, but are not limited to, Raney nickel, supported nickel catalysts, Ponder nickel catalysts, nickel alloys, dichlorobis(tributyl-phosphine)nickel(II), bis(tricyclohexylphosphine)nickel(II) dichloride, tetrakis(triphenylphosphite) nickel(0), Ni(COD)₂, Ni(PPh₃)₄, Ni(PPh₃)₂Cl₂, Ni(acac)₂, Cl₂Ni(PMe₃)₂, Cl₂Ni(PEt₃)₂, Cl₂Ni(Me₂PPh)₂, Cl₂Ni(MePPh₂)₂, and Cl₂Ni(Me₂PCH₂CH₂PMe₂). In some embodiments, the catalyst is a platinum catalyst. Examples of platinum catalysts include, but are not limited to, platinum carbonyl cyclovinylmethylsiloxane complexes, platinum divinyltetramethyldisiloxane complexes, platinum cyclovinylmethyl siloxane complexes, platinum octanaldehyde/octanol complexes, olefin complexes of platinum, olefin complexes of chloroplatinic acid, Karstedt's catalyst (Pt₂[[(CH₂═CH)

(CH₃)₂Si]₂O]₃), Ashby's catalyst (Pt₄[CH₂=CHSi(CH₃)O]₄), a Lamoreaux catalyst (a Pt-octanal/octanol complex), platinic chloride, chloroplatinic acid, finely divided platinum metal ("platinum black"), platinum oxide, platinum metal on graphitized carbon, bis(acetylacetonato) platinum, (η⁵-cyclopentadienyl)trialkylplatinum, finely divided platinum oxide, PtO₂ ("Adam's catalyst"), and chloroplatinic acid hexahydrate (Speier catalyst). In some embodiments, the catalyst is a palladium catalyst. In some embodiments, the palladium catalyst is selected from Pd(dba)₂, PdCl₂, Pd(OAc)₂, Pd(dppf)Cl₂, Pd₂(dba)₃, PdCl₂(CH₃CN)₂, PdCl₂(PPh₃)₂, Pd(t-Bu)₃, Pd(dppf)Cl₂·CH₂Cl₂, Pd(PPh₃)₄, Pd(OAc)/PPh₃, PdCl₂[(Pet₃)]₂, Pd(DIPHOS)₂, PdCl₂(Bipy), [PdCl(Ph₂PCH₂PPh₂)]₂, PdCl₂[P(o-Tol)₃]₂, Pd₂(dba)₃/P(o-Tol)₃, Pd₂(dba)/P(furyl)₃, PdCl₂[P(furyl)₃]₂, PdCl₂(PMePh₂)₂, PdCl₂[P(4-F-Ph)₃]₂, PdCl₂[P(C₆F₆)₃]₂, PdCl₂[P(2-COOH-Ph)(Ph)₂]₂, and PdCl₂[P(4-COOH-Ph)(Ph)₂]₂. In some embodiments, the ninth catalyst comprising a metal is Pd(dppf)Cl₂·CH₂Cl₂.

In some embodiments, the process of preparing the compound of Formula I or a pharmaceutically acceptable salt thereof further comprises treating the compound of formula 25 or a salt thereof with a fourth diboronic acid or ester in the presence of a tenth catalyst comprising a metal to form a mixture, and treating the mixture with a seventh strong base and hydrogen peroxide to form the compound of formula 26 or a salt thereof.

In some embodiments, the tenth catalyst comprising a metal can be a nickel catalyst, a palladium catalyst, or a platinum catalyst. In some embodiments, the catalyst is a nickel catalyst. Examples of nickel catalysts include, but are not limited to, Raney nickel, supported nickel catalysts, Ponder nickel catalysts, nickel alloys, dichlorobis(tributylphosphine)nickel(II), bis(tricyclohexylphosphine)nickel(II) dichloride, tetrakis(triphenylphosphite) nickel(0), Ni(COD)₂, Ni(PPh₃)₄, Ni(PPh₃)₂Cl₂, Ni(acac)₂, Cl₂Ni(PMe₃)₂, Cl₂Ni(PEt₃)₂, Cl₂Ni(Me₂PPh)₂, Cl₂Ni(MePPh₂)₂, and Cl₂Ni(Me₂PCH₂CH₂PMe₂). In some embodiments, the catalyst is a platinum catalyst. Examples of platinum catalysts include, but are not limited to, platinum carbonyl cyclovinylmethylsiloxane complexes, platinum divinyltetramethyldisiloxane complexes, platinum cyclovinylmethyl siloxane complexes, platinum octanaldehyde/octanol complexes, olefin complexes of platinum, olefin complexes of chloroplatinic acid, Karstedt's catalyst (Pt₂[[(CH₂=CH)(CH₃)₂Si]₂O]₃), Ashby's catalyst (Pt₄[CH₂=CHSi(CH₃)O]₄), a Lamoreaux catalyst (a Pt-octanal/octanol complex), platinic chloride, chloroplatinic acid, finely divided platinum metal ("platinum black"), platinum oxide, platinum metal on graphitized carbon, bis(acetylacetonato) platinum, (η⁵-cyclopentadienyl)trialkylplatinum, finely divided platinum oxide, PtO₂ ("Adam's catalyst"), and chloroplatinic acid hexahydrate (Speier catalyst). In some embodiments, the catalyst is a palladium catalyst. In some embodiments, the palladium catalyst is selected from Pd(dba)₂, PdCl₂, Pd(OAc)₂, Pd(dppf)Cl₂, Pd₂(dba)₃, PdCl₂(CH₃CN)₂, PdCl₂(PPh₃)₂, Pd(t-Bu)₃, Pd(dppf)Cl₂·CH₂Cl₂, Pd(PPh₃)₄, Pd(OAc)/PPh₃, PdCl₂[(Pet₃)]₂, Pd(DIPHOS)₂, PdCl₂(Bipy), [PdCl(Ph₂PCH₂PPh₂)]₂, PdCl₂[P(o-Tol)₃]₂, Pd₂(dba)₃/P(o-Tol)₃, Pd₂(dba)/P(furyl)₃, PdCl₂[P(furyl)₃]₂, PdCl₂(PMePh₂)₂, PdCl₂[P(4-F-Ph)₃]₂, PdCl₂[P(C₆F₆)₃]₂, PdCl₂[P(2-COOH-Ph)(Ph)₂]₂, and PdCl₂[P(4-COOH-Ph)(Ph)₂]₂. In some embodiments, the tenth catalyst comprising a metal is Pd(dbbf).

In some embodiments, the fourth diboronic acid or ester is selected from among an alkenyl boronic acid, an alkyl boronic acid, an aryl boronic acid, a heteroaryl boronic acid, and a pinacol boronic ester. In some embodiments, the fourth diboronic acid or ester is bis(pinacolato)diboron.

In some embodiments, the seventh strong base is selected from lithium hydroxide, sodium hydroxide, potassium hydroxide, rubidium hydroxide, cesium hydroxide, calcium hydroxide, strontium hydroxide, and barium hydroxide. In some embodiments, the seventh strong base is sodium hydroxide. In some embodiments, the seventh strong base is 1.0 M sodium hydroxide.

In some embodiments, $R^1$ is Boc and compound 26 is compound 26a

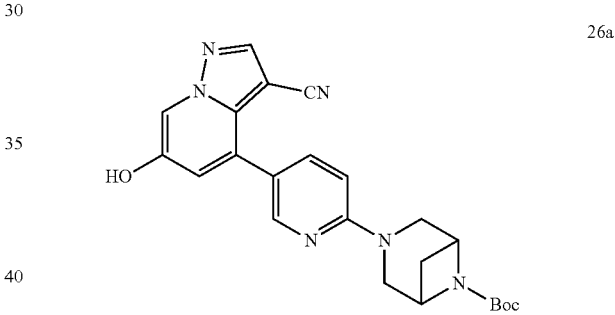

26a or salt thereof.

In some embodiments, a compound of formula 13 or salt thereof can be prepared as shown in Scheme 1, wherein X, $R^2$ and $R^5$ are defined below.

Scheme 1

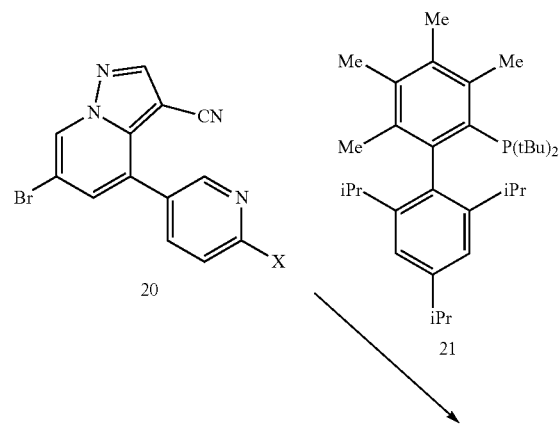

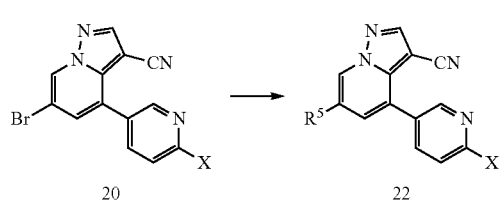
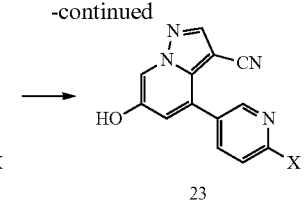
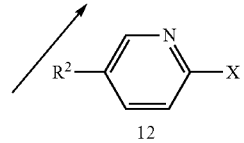
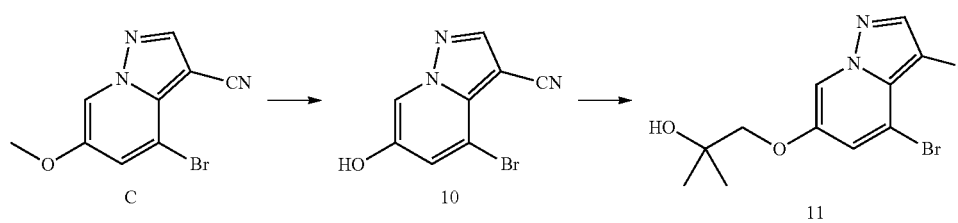

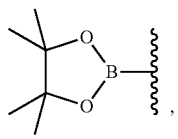
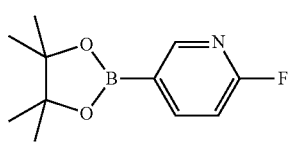

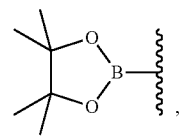 [SMILES: *B1OC(C)(C)C(C)(C)O1]

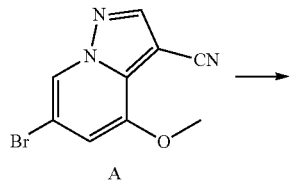

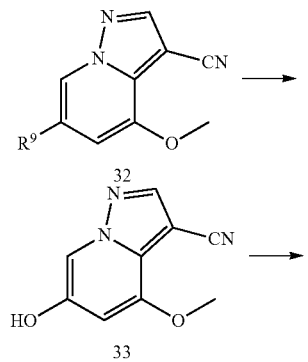

In some embodiments, X is selected from a halogen and a sulfonate. In some embodiments, X is selected from the group consisting of F, Cl, Br, and I. In some embodiments, X is F. In some embodiments, X is a sulfonate. In some embodiments, X is selected from the group consisting of triflate, mesylate, and tosylate.

In some embodiments of Scheme 1, $R^2$ is selected from the group consisting of an organoborane compound, an organostannane compound represented by the formula —Sn(alkyl)$_3$, a zinc halide represented by the formula —ZnX, wherein X is a halide, and a magnesium halide represented by the formula —MgX, wherein X is a halide. In some embodiments, $R^2$ is an organoborane compound. In some embodiments, $R^2$ is a boronic acid or ester. In some embodiments, the boronic acid or ester is boronic acid pinacol ester. In some embodiments, the boronic acid or ester is represented by the formula wherein the wavy line indicates the point of attachment to the pyridine ring of compound 12 or salt thereof.

In some embodiments, $R^2$ is boronic acid pinacol ester and the compound 12 is compound 12a 12a or salt thereof.

In some embodiments of Scheme 1, $R^5$ is a boronic acid or ester. In some embodiments, the boronic acid or ester is selected from among an alkenyl boronic acid, an alkyl boronic acid, an aryl boronic acid, a heteroaryl boronic acid, and a pinacol boronic ester. In some embodiments, the diboronic acid or ester is boronic acid pinacol ester. In some embodiments, the boronic acid or ester is represented by the formula wherein the wavy line indicates the point of attachment to the pyrazolo[1,5-a]pyridine ring of compound 22 or salt thereof.

In some embodiments, the compound of formula 13 or a salt thereof can be prepared as shown in Scheme 2, wherein X, $R^6$ and $R^9$ are defined below.

Scheme 2

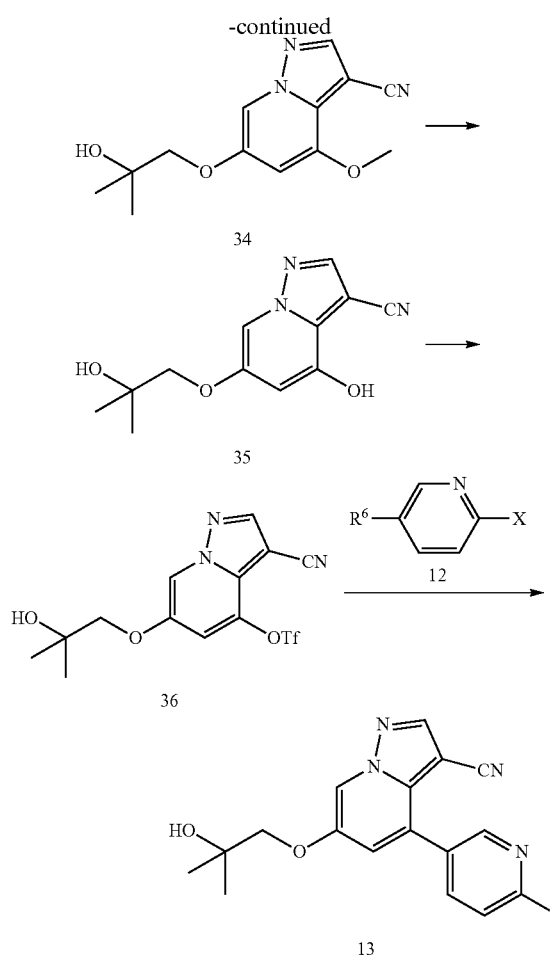

from the group consisting of F, Cl, Br, and I. In some embodiments, X is F. In some embodiments, X is a sulfonate. In some embodiments, X is selected from the group consisting of triflate, mesylate, and tosylate.

In some embodiments of Scheme 2, $R^6$ is a boronic acid or ester. In some embodiments, the boronic acid or ester is boronic acid pinacol ester. In some embodiments, the boronic acid or ester is represented by the formula

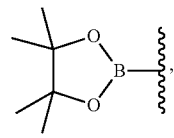

wherein the wavy line indicates the point of attachment to the pyridine ring of compound 12 or salt thereof.

In some embodiments of Scheme 2, $R^9$ is a boronic acid or ester. In some embodiments, the boronic acid or ester is selected from among an alkenyl boronic acid, an alkyl boronic acid, an aryl boronic acid, a heteroaryl boronic acid, and a pinacol boronic ester. In some embodiments, the diboronic acid or ester is boronic acid pinacol ester. In some embodiments, the boronic acid or ester is represented by the formula

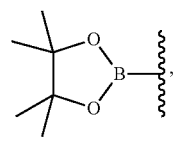 [SMILES: *B1OC(C)(C)C(C)(C)O1]

wherein the wavy line indicates the point of attachment to the pyrazolo[1,5-a]pyridine ring of compound 32 or salt thereof.

In some embodiments, the compound of Formula I or a pharmaceutically acceptable salt thereof can be prepared as shown in Scheme 3, wherein X and $R^1$ are defined below.

In some embodiments of Scheme 2, X is selected from a halogen and a sulfonate. In some embodiments, X is selected

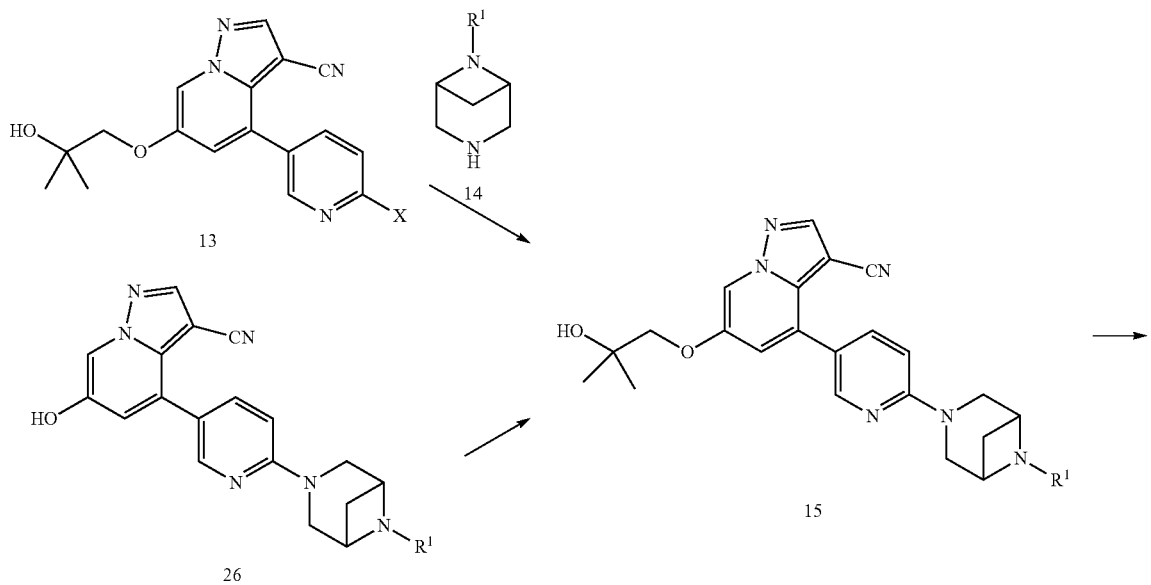

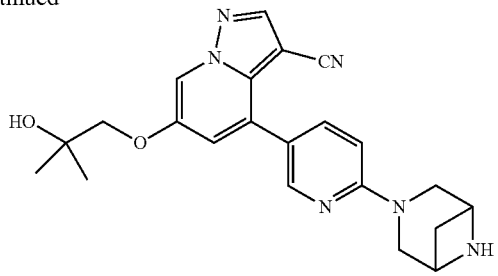

16

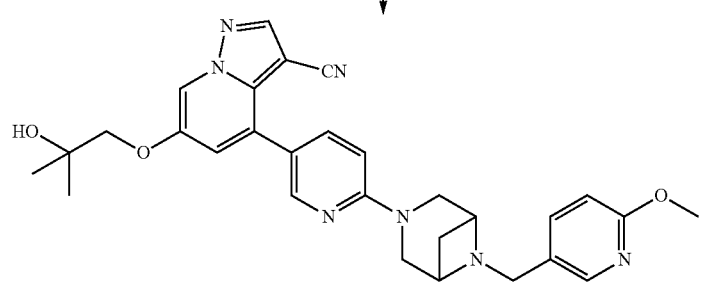

Formula I

In some embodiments of Scheme 3, X is selected from a halogen and a sulfonate. In some embodiments, X is selected from the group consisting of F, Cl, Br, and I. In some embodiments, X is F. In some embodiments, X is a sulfonate. In some embodiments, X is selected from the group consisting of triflate, mesylate, and tosylate.

In some embodiments of Scheme 3, $R^1$ is an amine protecting group that is selected from formyl, acetyl, trifluoroacetyl, benzyl, benzoyl, carbamate, benzyloxycarbonyl, p-methoxybenzyl carbonyl, tert-butyloxycarbonyl (Boc), trimethylsilyl, 2-trimethylsilyl-ethanesulfonyl, trityl and substituted trityl groups, allyloxycarbonyl, 9-fluorenylmethyloxycarbonyl, nitroveratryloxycarbonyl, p-methoxybenzyl and tosyl. In some embodiments, $R^1$ is tert-butyloxycarbonyl (Boc).

In some embodiments, $R^1$ is Boc and compound 14 is compound 14a

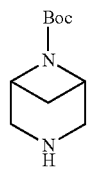

14a or salt thereof.

In some embodiments, $R^1$ is Boc and compound 15 is compound 15a

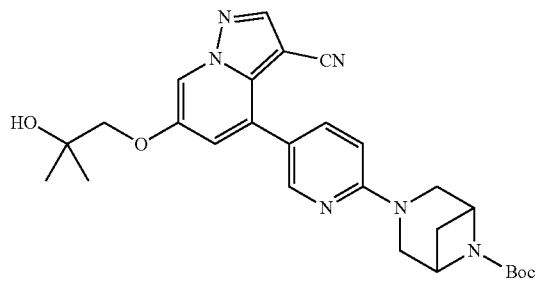

15a or salt thereof.

In some embodiments, $R^1$ is Boc and compound 26 is compound 26a

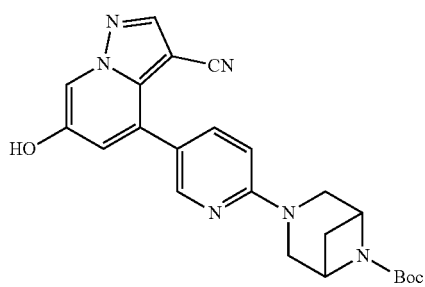

26a or salt thereof.

In some embodiments, the compound of Formula I or a pharmaceutically acceptable salt thereof can be prepared as shown in Scheme 4, wherein $R^7$ is defined below.

Scheme 4

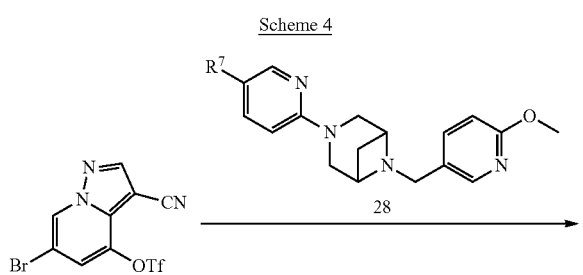

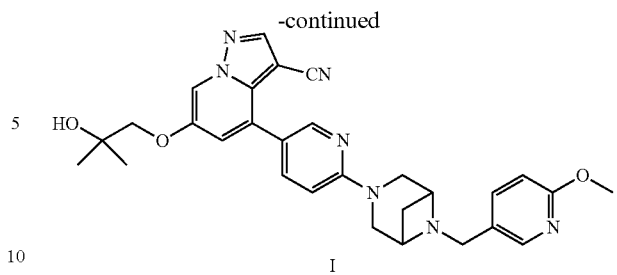

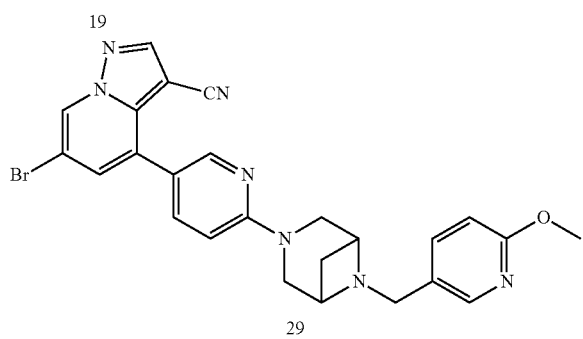

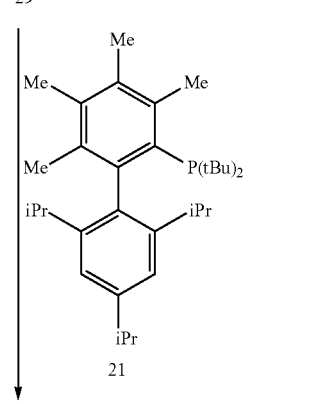

In some embodiments of Scheme 4, $R^7$ is a boronic acid or ester. In some embodiments, the boronic acid or ester is selected from among an alkenyl boronic acid, an alkyl boronic acid, an aryl boronic acid, a heteroaryl boronic acid, and a pinacol boronic ester. In some embodiments, the diboronic acid or ester is boronic acid pinacol ester. In some embodiments, the boronic acid or ester is represented by the formula

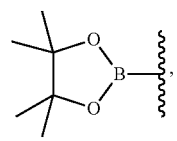 [SMILES: *B1OC(C)(C)C(C)(C)O1]

wherein the wavy line indicates the point of attachment to the pyridine ring of compound 28 or salt thereof.

In some embodiments, the compound of Formula I or a pharmaceutically acceptable salt thereof can be prepared as shown in Scheme 5, wherein $R^8$ is defined below.

Scheme 5

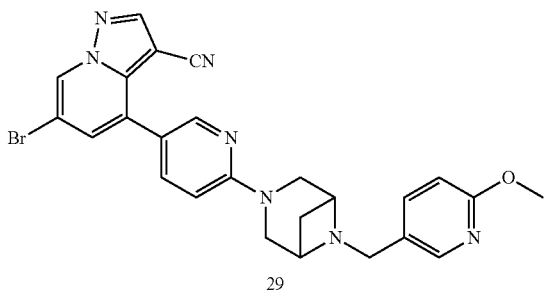

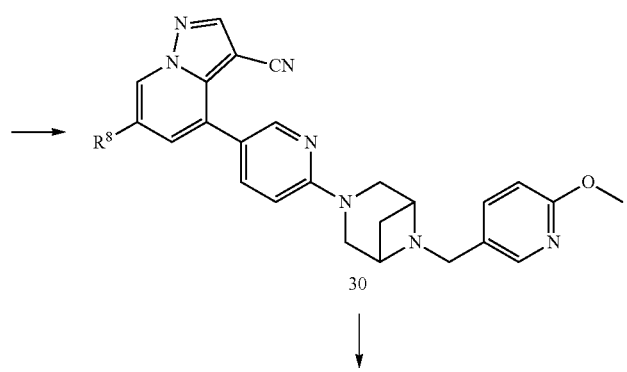

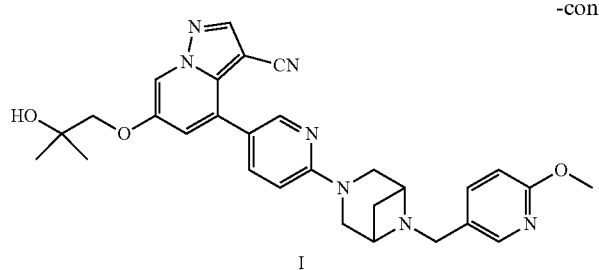

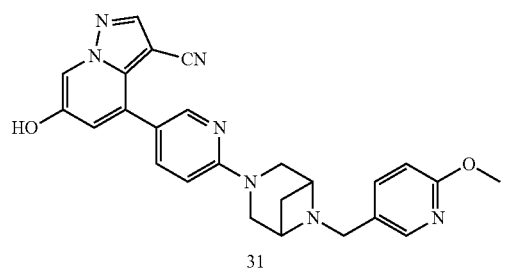

In some embodiments of Scheme 5, $R^8$ is a boronic acid or ester. In some embodiments, the boronic acid or ester is selected from among an alkenyl boronic acid, an alkyl boronic acid, an aryl boronic acid, a heteroaryl boronic acid, and a pinacol boronic ester. In some embodiments, the diboronic acid or ester is boronic acid pinacol ester. In some embodiments, the boronic acid or ester is represented by the formula

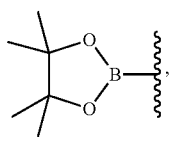

wherein the wavy line indicates the point of attachment to the pyridine ring of compound 30 or salt thereof.

In some embodiments, the compound of formula 20 or salt thereof can be prepared as shown in Scheme 6, wherein $R^6$ is defined below.

Scheme 6

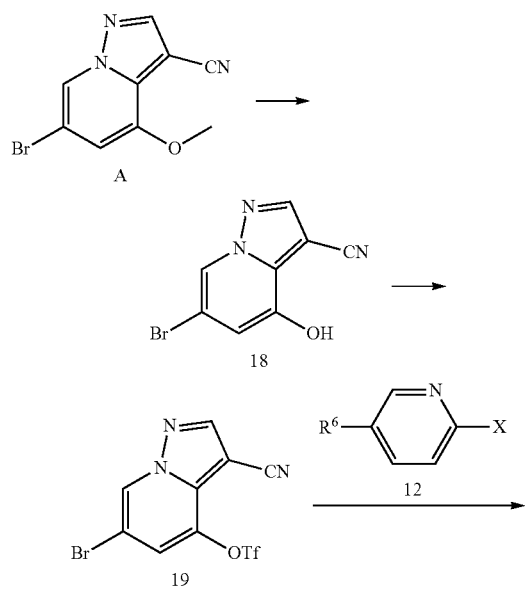

In some embodiments of Scheme 6, $R^6$ is a boronic acid or ester. In some embodiments, the boronic acid or ester is boronic acid pinacol ester. In some embodiments, the boronic acid or ester is represented by the formula

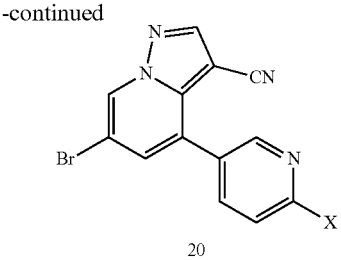

wherein the wavy line indicates the point of attachment to the pyridine ring of compound 12 or salt thereof.

In some embodiments, the process further comprises preparing the compound of formula A or a salt thereof by a process comprising:

a) treating a compound of formula 1a

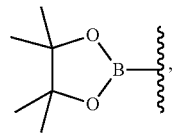

or a salt thereof with O-(mesitylsulfonyl)hydroxylamine to form a compound of formula 2a

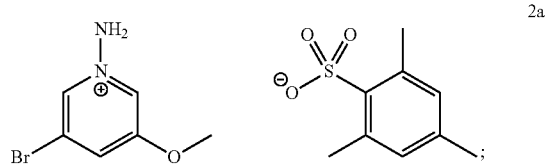

and b) treating the compound of formula 2a with acrylonitrile or an acrylonitrile derivative in the presence of a first non-nucleophilic base to form the compound of formula A.

In some embodiments, the compound of formula A or a salt thereof is prepared by a process comprising:

a) treating a compound of formula 1a

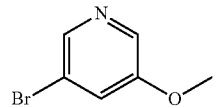

1a or a salt thereof with O-(mesitylsulfonyl)hydroxylamine to form a compound of formula 2a

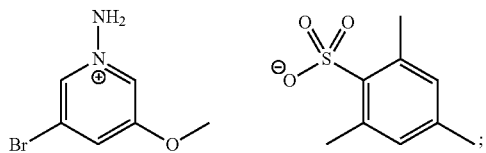

2a b) treating the compound of formula 2a with a compound of formula 27

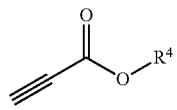

27 or a salt thereof, wherein $R^4$ is a C1-C6 alkyl, to form a mixture of compounds of formula 3 and formula 4

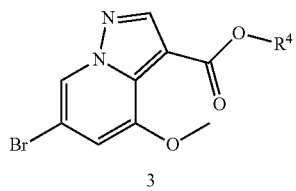

3

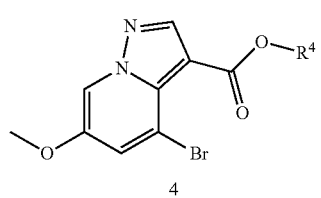

4 or salts thereof;

c) separating the compound of formula 3 from the compound of formula 4;

d) treating the compound of formula 3 with a first dilute strong acid to form a compound of formula 5A

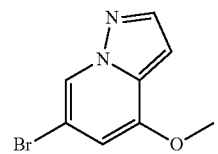

5A or a salt thereof;

e) treating the compound of formula 5A or a salt thereof with a first substituted amide and a first acid chloride to form a compound of formula 6A

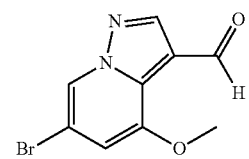

6A or a salt thereof;

f) treating the compound of formula 6A or a salt thereof with hydroxylamine to form a compound of formula 7A

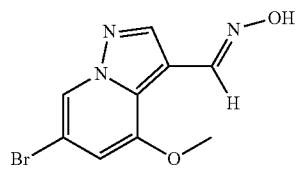

7A or a salt thereof; and g) treating the compound of formula 7A with a first acid anhydride to form the compound of formula A.

In some embodiments, a compound of formula A or salt thereof can be prepared as shown in Scheme 7, wherein $R^4$ is as defined below.

Scheme 7

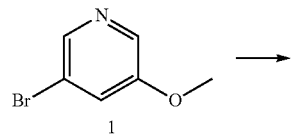

1

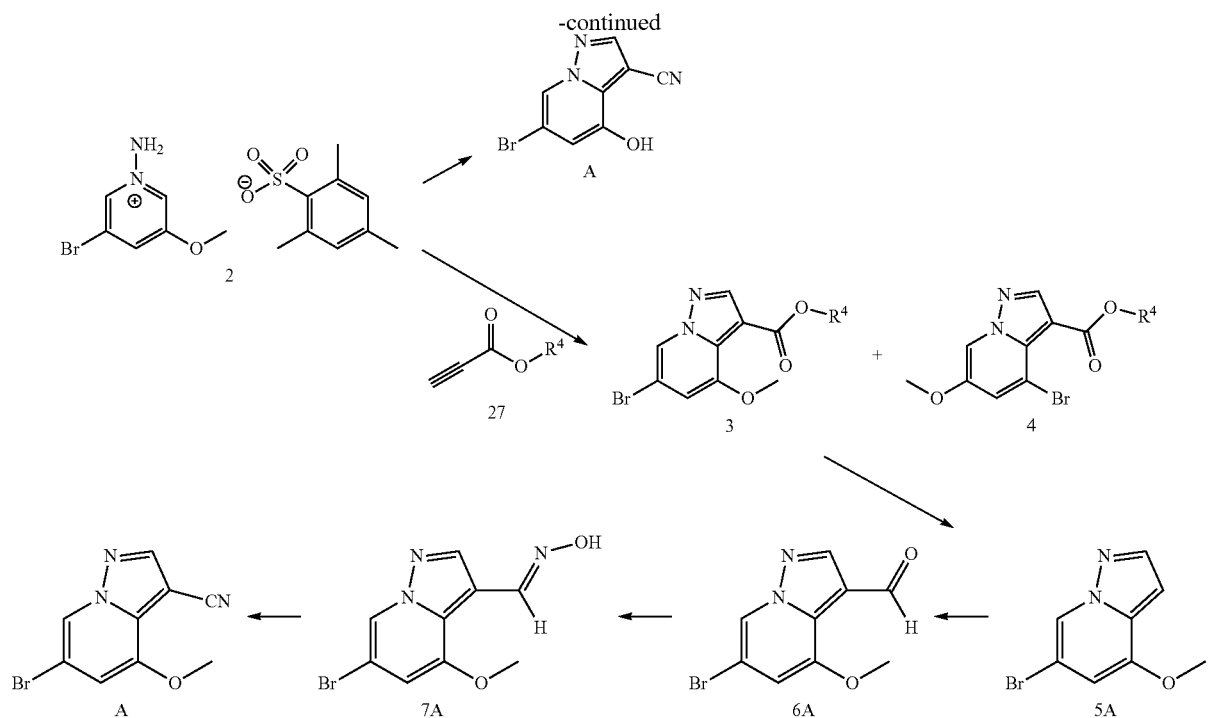

In some embodiments of Scheme 7, $R^4$ is a C1-C6 alkyl selected from methyl, ethyl, propyl, butyl, pentyl, and hexyl. In some embodiments, the C1-C6 alkyl is a straight chain alkyl. In some embodiments, the C1-C6 alkyl is branched. In some embodiments, the C1-C6 alkyl is methyl. In some embodiments, the C1-C6 alkyl is ethyl.

In some embodiments, $R^4$ is ethyl and compound 27 is compound

27a

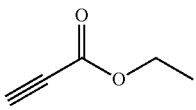

or salt thereof.

In some embodiments, $R^4$ is ethyl and compound 3 is compound 3a

3a

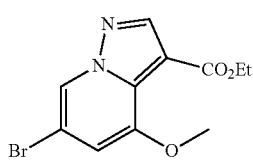

or salt thereof.

In some embodiments, $R^4$ is ethyl and compound 4 is compound 4a

4a

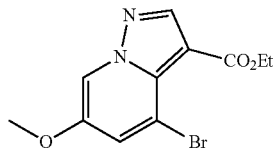

or salt thereof.

In some embodiments, the compound of formula 2a or salt thereof is treated with acrylonitrile or an acrylonitrile derivative. In some embodiments, the acrylonitrile derivative is 2-chloroacrylonitrile. In some embodiments, the compound of formula 2 or a salt thereof is treated with $CH_2$=C(Y)CN, wherein Y is hydrogen or a leaving group. In some embodiments, Y is a halogen. For example, Y is selected from the group consisting of F, Cl, Br, and I. In some embodiments, Y is Cl.

In some embodiments, the compound of formula 2a or salt thereof is treated with acrylonitrile or an acrylonitrile derivative in the presence of a first non-nucleophilic base. In some embodiments, the first non-nucleophilic base is selected from triethylamine (TEA), diisopropylethylamine (DIPEA), N-methylmorpholine (NMM), tri-tert-butylpyrimidine (TTBP), 1,4-diazabicyclo-[2.2.2]octane (DABCO), 1,8-diazabicyclo[5.4.0]undec-7-ene (DBU), N,N-diethylaniline, pyridine, 2,6-lutidine, 2,4,6-collidine, 4-dimethyl aminopyridine, quinuclidine, 2,6-di-tert-butylpyridine, tert-butylphosphazene, lithium diisopropylamide, sodium bis(trimethylsilyl)amide, potassium bis(trimethylsilyl)amide, lithium tetramethylpiperidide, sodium hydride, potassium hydride, sodium tert-butoxide, and potassium tert-butoxide. In some embodiments, the first non-nucleophilic base is DBU.

In some embodiments, the compound of formula 3 or salt thereof is treated with a first dilute strong acid. In some embodiments, the first dilute strong acid is selected from perchloric acid, hydroiodic acid, hydrobromic acid, hydrochloric acid, sulfuric acid, p-toluenesulfonic acid, and methanesulfonic acid. In some embodiments, the first dilute strong acid is dilute hydrobromic acid.

In some embodiments, the compound of formula 5A or salt thereof is treated with a first substituted amide. As used herein, the term "substituted amide" refers to an amide group that has a set of its hydrogen atoms replaced by a set of substituent groups. Examples of N-substituted amide groups include —(C═O)NRR', where R and R' are independently selected from hydride groups, alkyl groups, alkenyl groups, alkynyl groups, and aryl groups, and at least one of R and R' is not a hydride group. In some embodiments, the first substituted amide is selected from benzyl methyl formamide, N-formylmorpholine, dimethylacetamide, N-methylpyrrolidone, N-methylformanilide, N,N-dimethylformamide (DMF), N-methylformamide, N-formylpiperidine, and N-formylindoline. In some embodiments, the first substituted amide is DMF.

In some embodiments, the compound of formula 5A or salt thereof is treated with a first acid chloride. In some embodiments, the first acid chloride is selected from phosphoryl chloride (POCl$_3$), phosgene (COCl$_2$), thionyl chloride (SOCl$_2$), oxalyl chloride (C$_2$O$_2$Cl$_2$), acetyl chloride (CH$_3$COCl), an aromatic acid chloride (ArCOCl), an aromatic thionyl chloride (ArSO$_2$Cl), phosphorus pentachloride (PCl$_5$), dimethylsulfamoyl chloride (Me$_2$NSO$_2$Cl), and a dialkoxysulfamoyl chloride (RO$_2$CNHSO$_2$Cl). In some embodiments, the first acid chloride is POCl$_3$.

In some embodiments, the compound of formula 7A or salt thereof is treated with a first acid anhydride. In some embodiments, the first acid anhydride is selected from acetic anhydride, formic anhydride, propionic anhydride, butyric anhydride, succinic anhydride, glutaric anhydride, methylsuccinic anhydride, maleic anhydride, methylmaleic anhydride, phthalic anhydride, 1,2,3,6-tetrahydrophthalic anhydride, 3,4,5,6-tetrahydrophthalic anhydride, hexahydrophthalic anhydride, cis-5-norbornene-(endo, exo)-2,3-dicarboxylic anhydride, and mixtures thereof. In some embodiments, the first acid anhydride is acetic anhydride.

In some embodiments, the process further comprises preparing the compound of formula A or a salt thereof by a process comprising:

a) treating a compound of formula 8A

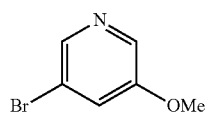

8A or a salt thereof with O-(2,4-dinitrophenyl)hydroxylamine to form the compound of formula 9A

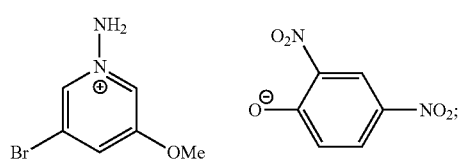

9A and b) treating the compound of formula 9A with acrylonitrile or an acrylonitrile derivative in the presence of a first non-nucleophilic base to form the compound of formula A.

In some embodiments, the compound of formula 9A is treated with acrylonitrile or an acrylonitrile derivative that is 2-chloroacrylonitrile.

In some embodiments, the first non-nucleophilic base is selected from triethylamine (TEA), diisopropylethylamine (DIPEA), N-methylmorpholine (NMM), tri-tert-butylpyrimidine (TTBP), 1,4-diazabicyclo-[2.2.2]octane (DABCO), 1,8-diazabicyclo[5.4.0]undec-7-ene (DBU), N,N-diethylaniline, pyridine, 2,6-lutidine, 2,4,6-collidine, 4-dimethylaminopyridine, quinuclidine, 2,6-di-tert-butylpyridine, tert-butyl-phosphazene, lithium diisopropylamide, sodium bis(trimethylsilyl)amide, potassium bis(trimethylsilyl)amide, lithium tetramethylpiperidide, sodium hydride, potassium hydride, sodium tert-butoxide, and potassium tert-butoxide. In some embodiments, the first non-nucleophilic base is DBU.

In some embodiments, a compound of formula A or salt thereof can be prepared as shown in Scheme 11.

Scheme 11

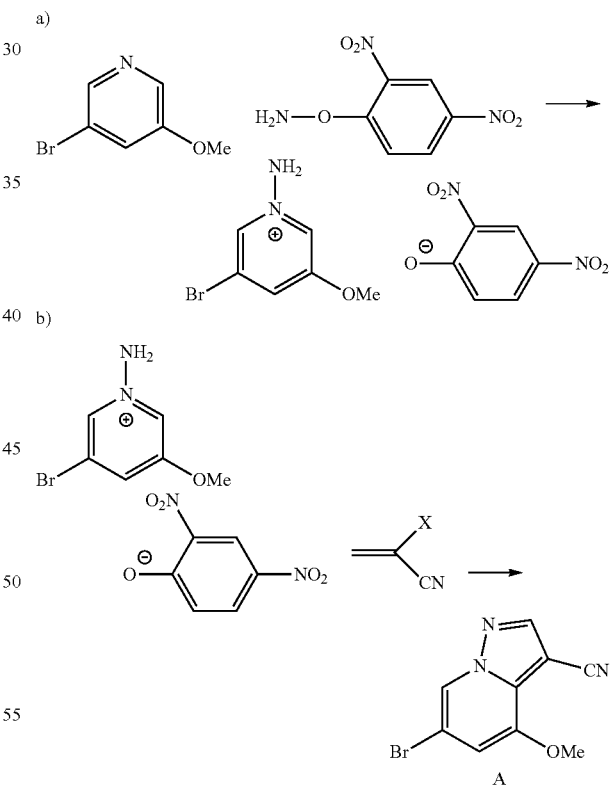

wherein X is halogen.

In some embodiments of Scheme 11, the intermediate 1-amino-3-bromo-5-methoxypyridin-1-ium 2,4-dinitrophenolate (9A) formed in (a) is isolated prior to the cyclization step (b).

In some embodiments, a compound of formula A or salt thereof can be prepared as shown in Scheme 12

Scheme 12

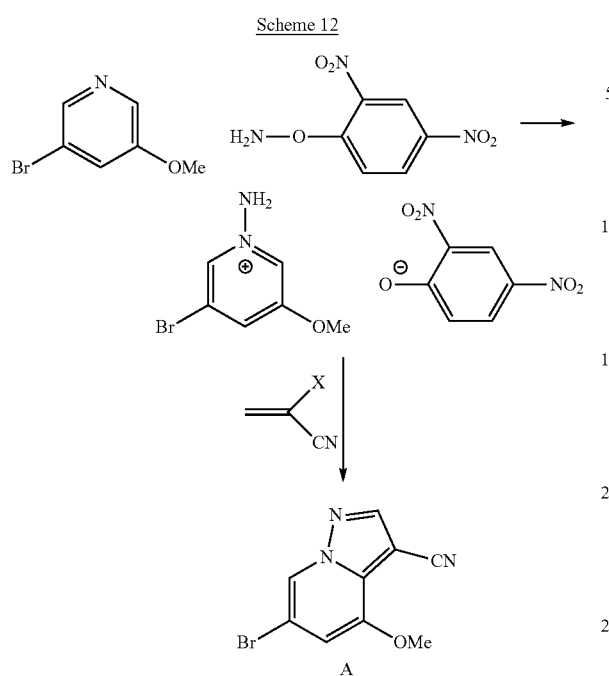

wherein X is halogen.

In Scheme 12, the intermediate 1-amino-3-bromo-5-methoxypyridin-1-ium 2,4-dinitrophenolate (9A) formed is not isolated prior to the cyclization step.

In some embodiments, a compound of formula A or salt thereof can be prepared as shown in Scheme 13.

Scheme 13 a)
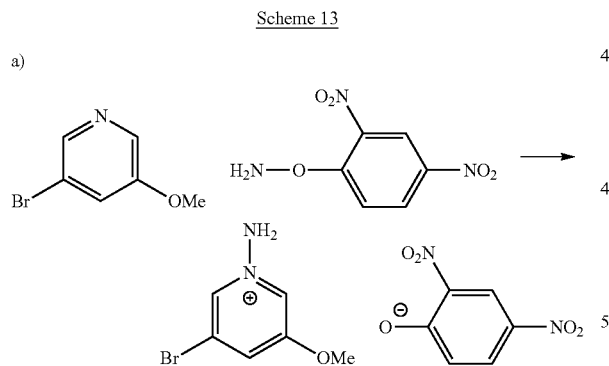

b)
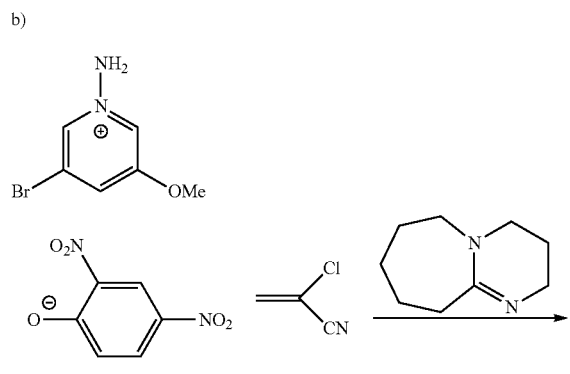

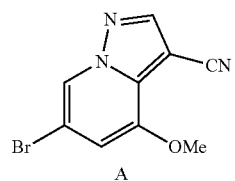

In some embodiments of Scheme 13, the intermediate 1-amino-3-bromo-5-methoxypyridin-1-ium 2,4-dinitrophenolate (9A) formed in (a) is isolated prior to the cyclization step (b).

In some embodiments, a compound of formula A or salt thereof can be prepared as shown in Scheme 14

Scheme 14

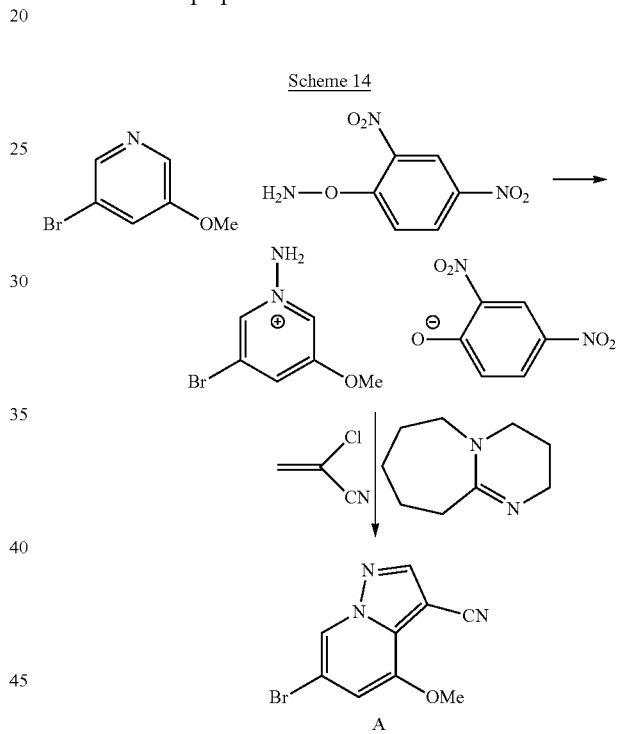

In Scheme 14, the intermediate 1-amino-3-bromo-5-methoxypyridin-1-ium 2,4-dinitrophenolate (9A) formed is not isolated prior to the cyclization step.

In some embodiments, a compound of formula 26 or salt thereof can be prepared as shown in Scheme 8, wherein $R^1$ and $R^3$ are as defined below.

Scheme 8

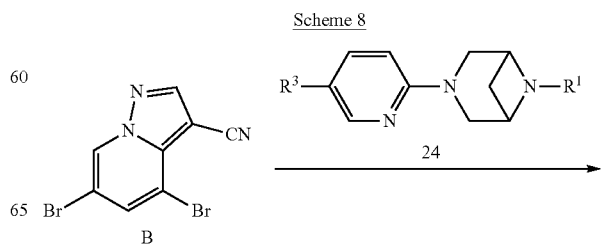

-continued

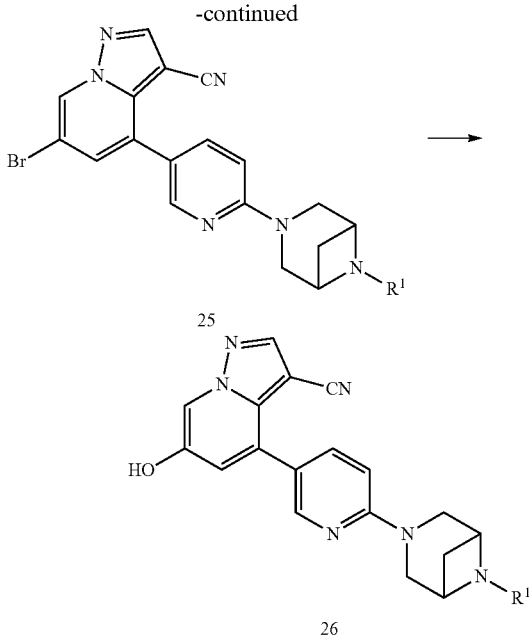

In some embodiments of Scheme 8, $R^1$ is an amine protecting group that is selected from formyl, acetyl, trifluoroacetyl, benzyl, benzoyl, carbamate, benzyloxycarbonyl, p-methoxybenzyl carbonyl, tert-butyloxycarbonyl (Boc), trimethylsilyl, 2-trimethylsilyl-ethanesulfonyl, trityl and substituted trityl groups, allyloxycarbonyl, 9-fluorenyl-methyloxycarbonyl, nitroveratryloxycarbonyl, p-methoxybenzyl and tosyl. In some embodiments, $R^1$ is tert-butyloxycarbonyl (Boc).

In some embodiments of Scheme 8, $R^3$ is a boronic acid or ester. In some embodiments, the boronic acid or ester is selected from among an alkenyl boronic acid, an alkyl boronic acid, an aryl boronic acid, a heteroaryl boronic acid, and a pinacol boronic ester. In some embodiments, the diboronic acid or ester is boronic acid pinacol ester. In some embodiments, the boronic acid or ester is represented by the formula

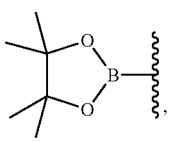 [SMILES: *B1OC(C)(C)C(C)(C)O1]

wherein the wavy line indicates the point of attachment to the pyridine ring of compound 24 or salt thereof.

In some embodiments, the process further comprises preparing the compound of formula B or a salt thereof by a process comprising:
a) treating a compound of formula 8

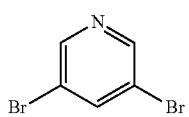

or a salt thereof with O-(mesitylsulfonyl)hydroxylamine to form the compound of formula 9

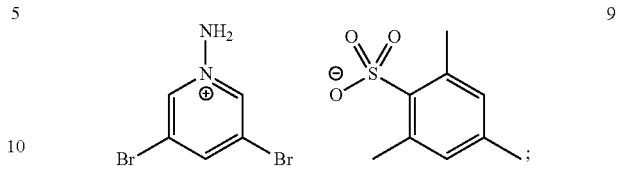

and
b) treating the compound of formula 9 with acrylonitrile or an acrylonitrile derivative in the presence of a second non-nucleophilic base to form a mixture, and treating the mixture with a second oxidant to form the compound of formula B.

In some embodiments, a compound of formula B or salt thereof can be prepared as shown in Scheme 9.

Scheme 9

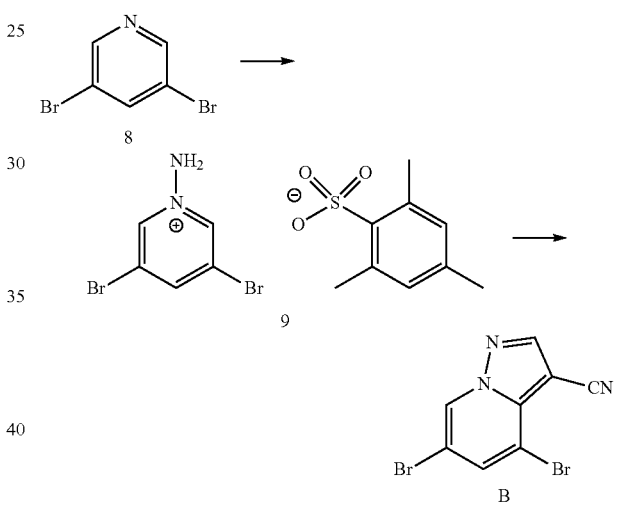

In some embodiments, the compound of formula 9 is treated with acrylonitrile or an acrylonitrile derivative that is 2-chloroacrylonitrile.

In some embodiments, the second non-nucleophilic base is selected from triethylamine (TEA), diisopropylethylamine (DIPEA), N-methylmorpholine (NMM), tri-tert-butylpyrimidine (TTBP), 1,4-diazabicyclo-[2.2.2]octane (DABCO), 1,8-diazabicyclo[5.4.0]undec-7-ene (DBU), N,N-diethylaniline, pyridine, 2,6-lutidine, 2,4,6-collidine, 4-dimethylaminopyridine, quinuclidine, 2,6-di-tert-butylpyridine, tert-butyl-phosphazene, lithium diisopropylamide, sodium bis(trimethylsilyl)amide, potassium bis(trimethylsilyl)amide, lithium tetramethylpiperidide, sodium hydride, potassium hydride, sodium tert-butoxide, and potassium tert-butoxide. In some embodiments, the second non-nucleophilic base is DIPEA.

In some embodiments, the second oxidant is selected from $O_2$, N-methylmorpholine N-oxide (NMO), chloranil (CA), 7,7,8,8-tetracyanoquinodimethane (TCNQ), benzylidene-malononitrile (BMCN), tetracyanoethylene (TCNE), 2,3-dicyano-1,4-benzoquinone (DCBQ), and 2,3-dichloro-5,6-dicyano-1,4-benzoquinone (DDQ). In some embodiments, the oxidant is DDQ.

In some embodiments, the process further comprises preparing the compound of formula C or a salt thereof by a process comprising:

a) treating the compound of formula 1a

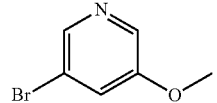

or a salt thereof with O-(mesitylsulfonyl)hydroxylamine to form the compound of formula 2a

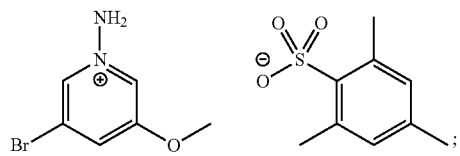

b) treating the compound of formula 2a with the compound of formula 27

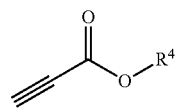

or a salt thereof, wherein $R^4$ is a C1-C6 alkyl described herein, to form a mixture of compounds of formula 3 and formula 4

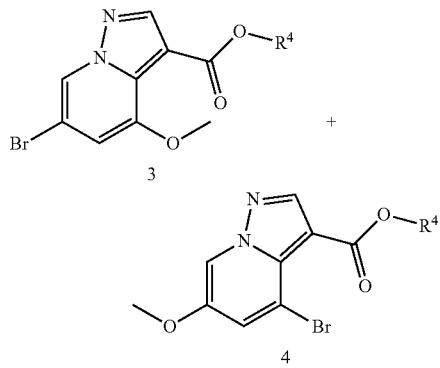

or salts thereof;

c) separating the compound of formula 4 from the compound of formula 3;

d) treating the compound of formula 4 with a second dilute strong acid to form the compound of formula 5C

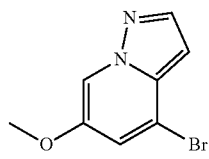

or a salt thereof;

e) treating the compound of formula 5C or a salt thereof with a second substituted amide and a second acid chloride to form a compound of formula 6C

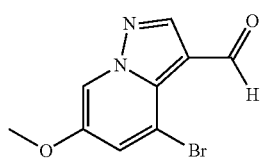

or a salt thereof;

f) treating the compound of formula 6C or a salt thereof with hydroxylamine to form a compound of formula 7C

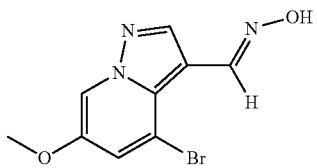

or a salt thereof; and g) treating the compound of formula 7C with a second acid anhydride to form the compound of formula C.

In some embodiments, a compound of formula C or salt thereof can be prepared as shown in Scheme 10, wherein $R^4$ is as defined below.

Scheme 10

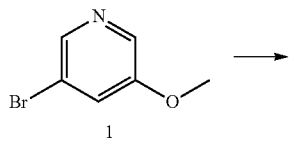

-continued

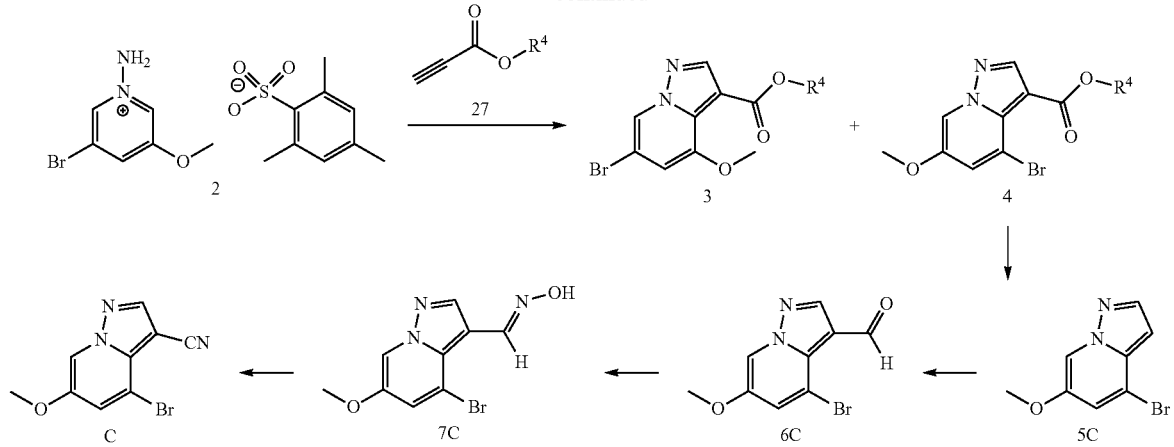

In some embodiments of Scheme 10, $R^4$ is a C1-C6 alkyl selected from methyl, ethyl, propyl, butyl, pentyl, and hexyl. In some embodiments, the C1-C6 alkyl is a straight chain alkyl. In some embodiments, the C1-C6 alkyl is branched. In some embodiments, the C1-C6 alkyl is methyl. In some embodiments, the C1-C6 alkyl is ethyl.

In some embodiments, $R^4$ is ethyl and compound 27 is compound 27a

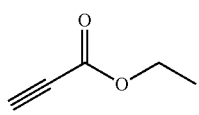

27a or salt thereof.

In some embodiments, $R^4$ is ethyl and compound 3 is compound 3a

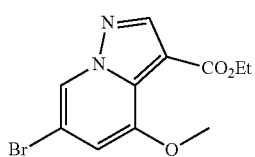

3a or salt thereof.

In some embodiments, $R^4$ is ethyl and compound 4 is compound 4a

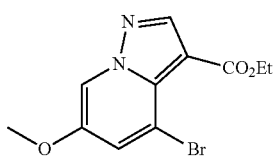

4a or salt thereof.

In some embodiments, the compound of formula 4 or salt thereof is treated with a second dilute strong acid. In some embodiments, the second dilute strong acid is selected from perchloric acid, hydroiodic acid, hydrobromic acid, hydrochloric acid, sulfuric acid, p-toluenesulfonic acid, and methanesulfonic acid. In some embodiments, the second dilute strong acid is dilute hydrobromic acid.

In some embodiments, the compound of formula 5C or salt thereof is treated with a second substituted amide. In some embodiments, the second substituted amide is selected from benzyl methyl formamide, N-formylmorpholine, dimethylacetamide, N-methylpyrrolidone, N-methylformanilide, N,N-dimethylformamide (DMF), N-methylformamide, N-formylpiperidine, and N-formylindoline. In some embodiments, the second substituted amide is DMF.

In some embodiments, the compound of formula 5C or salt thereof is treated with a second acid chloride. In some embodiments, the second acid chloride is selected from phosphoryl chloride ($POCl_3$), phosgene ($COCl_2$), thionyl chloride ($SOCl_2$), oxalyl chloride ($C_2O_2Cl_2$), acetyl chloride ($CH_3COCl$), an aromatic acid chloride (ArCOCl), an aromatic thionyl chloride ($ArSO_2Cl$), phosphorus pentachloride ($PCl_5$), dimethylsulfamoyl chloride ($Me_2NSO_2Cl$), and a dialkoxysulfamoyl chloride ($RO_2CNHSO_2Cl$). In some embodiments, the second acid chloride is $POCl_3$.

In some embodiments, the compound of formula 7C or salt thereof is treated with a second acid anhydride. In some embodiments, the second acid anhydride is selected from acetic anhydride, formic anhydride, propionic anhydride, butyric anhydride, succinic anhydride, glutaric anhydride, methylsuccinic anhydride, maleic anhydride, methylmaleic anhydride, phthalic anhydride, 1,2,3,6-tetrahydrophthalic anhydride, 3,4,5,6-tetrahydrophthalic anhydride, hexahydrophthalic anhydride, cis-5-norbornene-(endo, exo)-2,3-dicarboxylic anhydride, and mixtures thereof. In some embodiments, the second acid anhydride is acetic anhydride.

In some embodiments, provided herein is a process for preparing a pharmaceutical composition comprising mixing (i) a compound of Formula I or a pharmaceutically acceptable salt thereof prepared according to any of the processes described herein, and (ii) a pharmaceutically acceptable carrier. Pharmaceutical compositions containing the compound of Formula I or a pharmaceutically acceptable salt thereof as the active ingredient can be prepared by intimately mixing the compound of Formula I or a pharmaceutically acceptable salt thereof with a pharmaceutical carrier according to conventional pharmaceutical compounding techniques. The carrier can take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents, and the like; for solid oral preparations, such as powders, capsules and tablets, suitable carriers and additives include starches, sugars, diluents, granulating agents, lubricants, binders, disintegrating agents, and the like. Solid oral preparations can also be coated with substances such as sugars or be enteric-coated so as to modulate major site of absorption. For parenteral administration, the carrier will usually consist of sterile water, and other ingredients can be added to increase solubility or preservation. Injectable suspensions or solutions can also be prepared utilizing aqueous carriers along with appropriate additives.

The compound of Formula I or a pharmaceutically acceptable salt thereof can be administered by any convenient route, e.g., into the gastrointestinal tract (e.g., rectally or orally), the nose, lungs, musculature or vasculature, or transdermally or dermally. The compound of Formula I or a pharmaceutically acceptable salt thereof can be administered in any convenient administrative form, e.g., tablets, powders, capsules, solutions, dispersions, suspensions, syrups, sprays, suppositories, gels, emulsions, patches, etc. Such compositions can contain components that are conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Also provided herein are pharmaceutical compositions comprising a compound of Formula I or a pharmaceutically acceptable salt thereof. To prepare the pharmaceutical compositions provided herein, the compound of Formula I or a pharmaceutically acceptable salt thereof as the active ingredient is intimately admixed with a pharmaceutical carrier according to conventional pharmaceutical compounding techniques. The carrier can take a wide variety of forms depending of the form of preparation desired for administration, e.g., oral or parenteral, such as intramuscular.

To prepare the pharmaceutical compositions provided herein, the compound of Formula I or a pharmaceutically acceptable salt thereof as the active ingredient is intimately admixed with a pharmaceutical carrier according to conventional pharmaceutical compounding techniques. The carrier can take a wide variety of forms depending on the form of preparation desired for administration (e.g., oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications, such as *Pharmaceutical Dosage Forms: Tablets, Second Edition, Revised and Expanded*, Volumes 1-3, edited by Lieberman et al.; *Pharmaceutical Dosage Forms: Parenteral Medications*, Volumes 1-2, edited by Avis et al.; and *Pharmaceutical Dosage Forms: Disperse Systems*, Volumes 1-2, edited by Lieberman et al.; published by Marcel Dekker, Inc.

EXAMPLES

1. Preparation of a Compound of Formula A

A. A compound of formula A can be prepared according to the methods described in US 2017/0096425 and WO 2017/011776. Briefly:

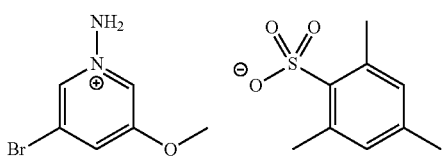

1-amino-3-bromo-5-methoxypyridin-1-ium 2,4,6-trimethylbenzenesulfonate (2a)

To a solution of O-(mesitylsulfonyl)hydroxylamine (26.6 g, 117 mmol) in DCM (570 mL) cooled to 0° C. was added 3-bromo-5-methoxypyridine (22.1 g, 117 mmol) in portions. The reaction mixture was stirred for 1 h at 0° C., then treated with additional 3-bromo-5-methoxypyridine (250 mg, 1.39 mmol) and stirred for an additional 2 h at 0° C. The reaction mixture was diluted with $Et_2O$ (600 mL), stirred at 0° C. for 10 min and then vacuum filtered, rinsed with $Et_2O$ (3×250 mL). Upon reduction in volume by about ⅓, the filtrate yielded additional precipitate which was collected by filtration. Both filter cakes were dried in vacuo to provide the title compound (39.3 g, 83% yield). $^1$H NMR ($CDCl_3$): δ 9.25 (br s, 1H), 8.99 (m, 1H), 8.74 (m, 1H), 7.46 (m, 1H), 6.83 (s, 2H), 3.92 (s, 3H), 2.65 (s, 6H), 2.22 (s, 3H).

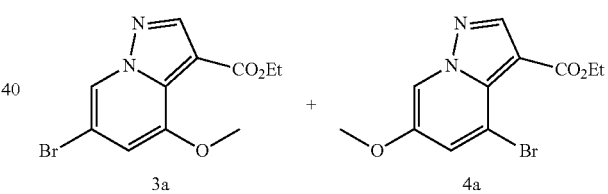

Ethyl-6-bromo-4-methoxypyrazolo[1,5-a]pyridine-3-carboxylate (3a) and ethyl-4-bromo-6-methoxypyrazolo[1,5-a]pyridine-3-carboxylate (4a)

To a magnetically stirred white suspension of 1-amino-3-bromo-5-methoxypyridin-1-ium 2,4,6-trimethylbenzenesulfonate (2a) (33.24 g, 82.42 mmol) in DMF (82 mL) at ambient temperature was added TEA (22.98 mL, 164.8 mmol), followed by drop-wise addition of ethyl propiolate (16.71 mL, 164.8 mmol). After vigorous stirring for 2 d, the reaction was slowly quenched via portion-wise addition to rapidly stirring ice water (820 mL). The mixture was stirred at ambient temperature for 10 min and then vacuum filtered. Solids collected were rinsed with water and air-dried, yielding the title compounds as an orange solid in an isomeric ratio of about 4:1 (by $^1$H NMR) with compound 3a as the major isomer (21 g). The wet solid isomeric mixture (about 75% w/w) was directly used in the next step without further purification. MS (apci) m/z=298.9, 300.9 (M+H). Regioisomeric ratio was determined by MeO chemical shift in $^1$H NMR ($CDCl_3$) δ 3.98 (3a) vs. 3.83 (4a).

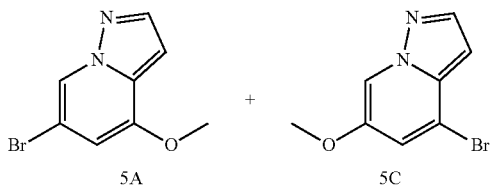

6-bromo-4-methoxypyrazolo[1,5-a]pyridine (5A) and 4-bromo-6-methoxypyrazolo[1,5-a]pyridine (5C)

The isomeric mixture of ethyl-6-bromo-4-methoxypyrazolo[1,5-a]pyridine-3-carboxylate (3a) and ethyl-4-bromo-4-methoxypyrazolo[1,5-a]pyridine-3-carboxylate (4a) described above (15 g, 50.1 mmol) was added to 48% HBr (114 mL) while stirring, then heated at 80° C. for 90 min, followed by stirring at ambient temperature overnight. The resulting suspension was vacuum filtered and rinsed with water. The aqueous filtrate and the filter cake were treated independently. The filter cake was taken up in MTBE and vacuum filtered to remove insoluble impurities. The MTBE filtrate was dried over anhydrous Na$_2$SO$_4$, filtered, and concentrated in vacuo to yield 6-bromo-4-methoxypyrazolo[1,5-a]pyridine (5A) as a beige solid (about 98:2 6-/4-Br; 5.08 g). MS (apci) m/z=226.9, 228.9 (M+H). $^1$H NMR (CDCl$_3$): δ 8.26 (m, 1H), 7.82 (d, 1H), 6.61 (m, 1H), 6.43 (m, 1H), 3.94 (s, 3H). Independently, the original aqueous reaction mixture filtrate was extracted with EtOAc (2×500 mL). The combined organic extracts were dried (Na$_2$SO$_4$), filtered, and concentrated in vacuo. The crude residue was taken up in DCM (50 mL) and then filtered to remove insoluble solids. Concentration of the DCM filtrate under vacuum followed by silica chromatography (0 to 50% EtOAc/hexanes) yielded a second batch of 6-bromo-4-methoxypyrazolo[1,5-a]pyridine (5A) as white solid (upper Rf spot, 2.06 g), as well as the minor isomer title compound 4-bromo-6-methoxypyrazolo[1,5-a]pyridine (5C), also as white solid (lower Rf spot, 1.32 g). MS (apci) m/z=226.9, 228.9 (M+H). $^1$H NMR (CDCl$_3$) δ 8.02 (m, 1H), 7.85 (d, 1H), 7.17 (d, 1H), 6.55 (m, 1H), 3.80 (s, 3H).

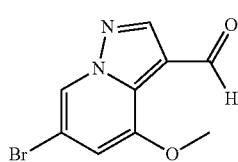

6A 6-bromo-4-methoxypyrazolo[1,5-a]pyridine-3-carbaldehyde (6A)

To a 0° C. solution of 6-bromo-4-methoxypyrazolo[1,5-a]pyridine (5A) (0.75 g, 3.303 mmol) in DMF (33 mL) was slowly added POCl$_3$ (0.92 mL, 9.909 mmol). The reaction was warmed to ambient temperature and stirred for 4 h and then diluted with H$_2$O (30 mL). The resulting suspension was basified to pH 9-10 with 1 M NaOH$_{(aq)}$, then stirred for 1 h and vacuum filtered, then rinsed sequentially with H$_2$O (25 mL) and MTBE (50 mL) to yield the title compound (0.76 g, 90% yield). MS (apci) m/z=256.9 (M+H).

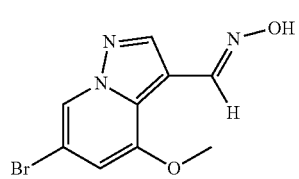

7A (E)-6-bromo-4-methoxypyrazolo[1,5-a]pyridine-3-carbaldehyde oxime (7A)

To a suspension of 6-bromo-4-methoxypyrazolo[1,5-a]pyridine-3-carbaldehyde (6A) (0.76 g, 3.0 mmol) and hydroxylamine hydrochloride (0.31 g, 4.5 mmol) in EtOH (40 mL) was added water (20 mL), and the reaction was stirred at 50° C. for 4 h. After cooling to ambient temperature the reaction mixture was concentrated in vacuo. The residue was suspended in water, then treated with saturated NaHCO$_{3(aq)}$ and vacuum filtered. The solids were rinsed sequentially with H$_2$O (25 mL) and MTBE (50 mL) to yield the title compound (0.68 g, 84% yield). MS (apci) m/z=271.9 (M+H).

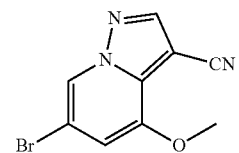

A 6-bromo-4-methoxypyrazolo[1,5-a]pyridine-3-carbonitrile (A)

A solution of (E)-6-bromo-4-methoxypyrazolo[1,5-a]pyridine-3-carbaldehyde oxime (7A) (17.15 g, 63.50 mmol) in acetic anhydride (707 mL, 7.49 mol) was heated at 120° C. overnight. Following subsequent distillation to remove the acetic anhydride, the remaining residue was dried in vacuo to yield the title compound (15.92 g, 99.4% yield). $^1$H NMR (CDCl$_3$): δ 8.32 (m, 1H), 8.12 (s, 1H), 6.74 (m, 1H), 4.03 (s, 3H).

B. A compound of formula A can also be prepared according to the method described below.

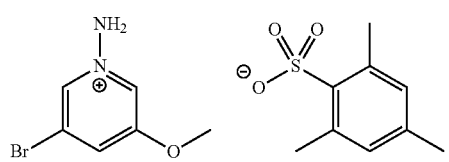

2a 1-amino-3-bromo-5-methoxypyridin-1-ium 2,4,6-trimethylbenzenesulfonate (2a)

To a solution of O-(mesitylsulfonyl)hydroxylamine (146 moles) in DCM (200 kg), was added 3-bromo-5-methoxypyridine (24.6 kg, 131 mol) dropwise at 0-5° C. The reaction was stirred for 16 h at 0-5° C. HPLC indicated that the reaction was complete. To the reaction n-heptanes (130 kg)

was added and the mixture was stirred at 0-5° C. for 1 h. The suspension was filtered and the filter cake was washed with n-heptane (20 kg×2) and dried to give compound 2 (40 kg) as a white solid. $^1$H NMR (400 MHz, DMSO-d$_6$), δ (ppm): 8.71 (s, 1H), 8.62 (s, 1H), 8.57 (s, 2H), 8.26 (s, 1H), 6.75 (s, 2H), 3.975 (s, 3H), 2.176 (s, 3H).

reaction is complete the heat is turned off and the mixture is allowed to cool to 20° C. The solids are filtered and the caked is washed with MTBE (1 mL) The wet cake is dried under vacuum with no heat for 18 h to provide 1-amino-3-bromo-5-methoxypyridin-1-ium 2,4-dinitrophenolate (862 mg, 83.7%).

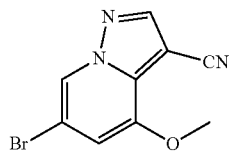

6-bromo-4-methoxypyrazolo[1,5-a]pyridine-3-carbonitrile (A)

To a solution of 1-amino-3-bromo-5-methoxypyridin-1-ium 2,4,6-trimethylbenzenesulfonate (2a) (40 kg, 100 mol) in acetonitrile (300 kg) was added 2-chloroacrylonitrile (13 kg, 150 mol) in one portion at −5° C. DBU (56 kg, 370 mol) was added dropwise at −10-0° C. to the solution. The reaction mixture was stirred at 25-30° C. for 16 h. HPLC showed the reaction was complete. The reaction mixture was quenched with H$_2$O (900 L), the suspension was filtered, and the solid was washed with H$_2$O (100 L). The resulting solid was combined with another lot of a compound of formula A. To the combined solids was added DCM (400 L), and the remaining solid was washed with DCM (4×400 L). The combined organic layers were concentrated under vacuum. The residue was suspended in n-heptane (80 kg), filtered, and dried to give compound of formula A (20.8 kg, 39.1%) as a yellow solid. $^1$H NMR (400 MHz, DMSO-d$_6$) δ (ppm): 8.92 (s, 1H), 8.58 (s, 1H), 7.23 (s, 1H). 4.036 (s, 3H).

C. A compound of formula A can also be prepared as described below:
a. Alternative stepwise preparation of a compound of formula A:

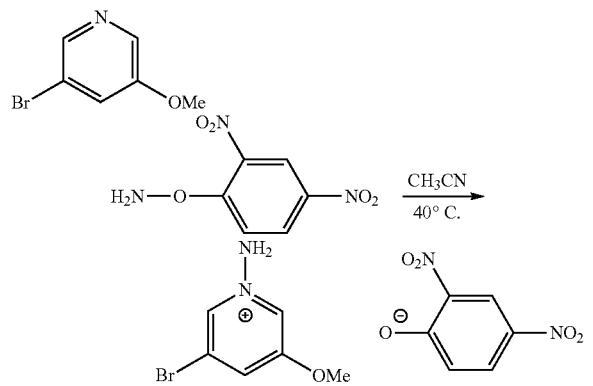

1-Amino-3-bromo-5-methoxypyridin-1-ium 2,4-dinitrophenolate

To a solution of 3-bromo-5-methoxypyridine (500 mg, 2.66 mmol) in acetonitrile (5 mL) is added O-(2,4-dinitrophenyl)hydroxylamine (635 mg, 3.19 mmol) with stirring at 20 to 25° C. The mixture is heated to 40° C. Once the

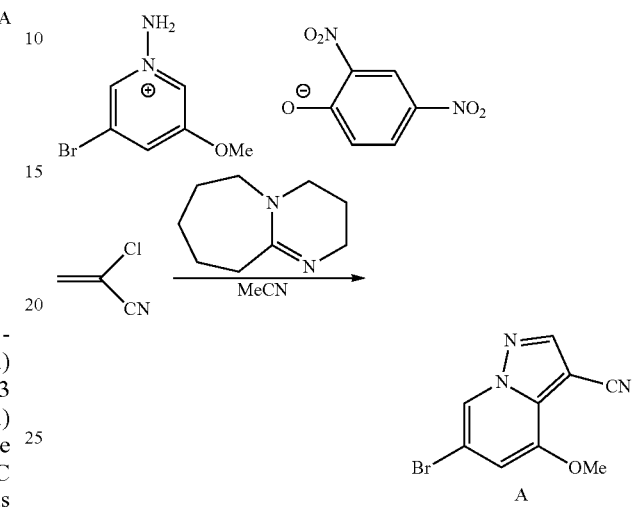

4-Bromo-6-methoxypyrazolo[1,5-a]pyridine-3-carbonitrile (A)

To a 0 to 5° C. suspension of N-amino-3-bromo-6-methoxypyridin-1-ium 2,4-dinitrophenolate (1.60 g, 4.13 mmol) in acetonitrile (6.4 mL) is added 2-chloroacrylonitrile (542 mg, 6.20 mmol). 1,8-Diazabicyclo[5.4.0]undec-7-ene (DBU, 2.3 g, 15.29 mmol) is added to the suspension at a rate such that the temperature is held below 15° C. The dark brown solution is kept at 0 to 5° C. for 1.5 h after the addition of DBU. Once the reaction is complete water (9.6 mL) is added the mixture and it is stirred for 3.5 h. The mixture is filtered, and the filtrate is used to aid the transfer for all solids from the flask to the funnel. The solids are washed with hexanes to remove acetonitrile and water from the wet cake. The wet cake is dried under vacuum to provide 4-bromo-6-methoxypyrazolo[1,5-a]pyridine-3-carbonitrile (A) (648 mg, 62.2%).

b. Alternative telescoped preparation of a compound of formula A:

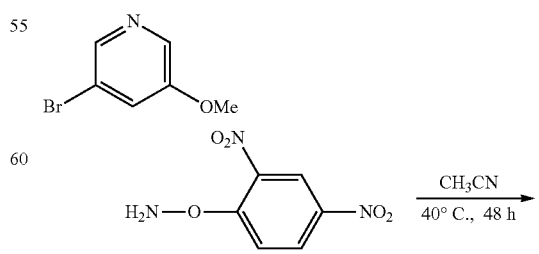

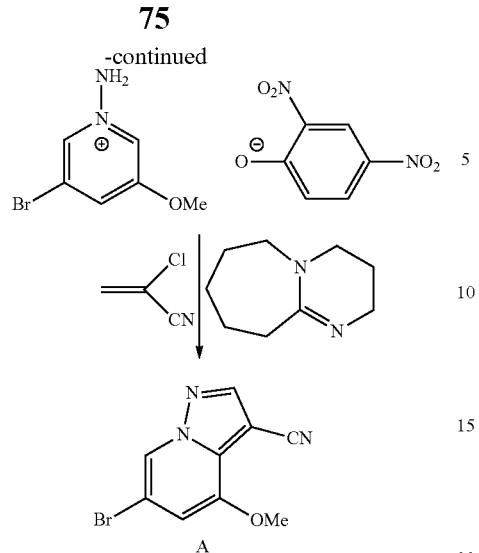

4-Bromo-6-methoxypyrazolo[1,5-a]pyridine-3-carbonitrile (A)

To a 0 to 5° C. solution of 3-bromo-5-methoxypyridine (6.0 g, 31.91 mmol) in acetonitrile (20 mL) is added O-(2,4-dinitrophenyl)hydroxylamine (7.6 g, 38.27 mmol) with stirring at 20 to 25° C. An additional charge of acetonitrile (19 mL) is made and the mixture is heated at 40° C. for 48 h. The heating is turned off and the mixture is allowed to cool to 0 to 5° C. and 2-chloroacrylonitrile (1.35 eq based on 3-bromo-5-methoxypyridine, 3.5 mL, 43.20 mmol) is added. 1,8-Diazabicyclo[5.4.0]undec-7-ene (DBU, 3.34 eq based on 3-bromo-5-methoxypyridine, 15.9 mL, 105.56 mmol) is added to the suspension at a rate such that the temperature is held below 8° C. The dark brown solution is kept at 0 to 5° C. for 1.5 h after the addition of DBU is completed. Once the reaction is judged complete, water (16 mL) is added and the mixture is stirred for 3 h. The mixture is filtered, and the filtrate is used to aid the transfer for all solid from the flask to funnel if necessary. The solids are washed with a solution of water/acetonitrile (6.6 mL, 5:1). The wet cake is dried in a vacuum oven at 45° C. for 24 h to provide 4-bromo-6-methoxypyrazolo[1,5-a]pyridine-3-carbonitrile (A) (3.9 g, 49%).

2. Preparation of a Compound of Formula B

[Structure 9: 1-amino-3,5-dibromo-pyridin-1-ium 2,4,6-trimethylbenzenesulfonate (9)]

To a solution of O-(mesitylsulfonyl)hydroxylamine in DCM (2 L) was added a solution of 3,5-dibromopyridine (320 g, 1.35 mol) in DCM (2.5 L) at 0-5° C. The reaction was stirred for 16 h at this temperature before ether (5 L) was added at 0-5° C. The suspension was then filtered and the cake was washed with Et₂O (4 L) to give compound 9 (500 g crude).

[Structure B: 4,6-dibromopyrazolo[1,5-a]pyridine-3-carbonitrile (B)]

To a mixture of compound 9 (40 g, 88.5 mmol) in p-dioxane (400 mL) was added acrylonitrile (10.72 g, 202 mmol) and DIPEA (14.8 g, 11.5 mmol). The mixture stirred at room temperature for 3 h, then DDQ (41.8 g, 184 mmol) was added and the mixture was stirred at room temperature for 3 additional hours. The reaction was monitored by TLC (eluent: ethyl acetate/petroleum ether, 1:2) and showed that compound 9 was consumed. The reaction mixture was poured into water (1.6 L) and the resulting solid was filtered. The solid was collected and then purified with column chromatography (silica-gel column eluting with ethyl acetate/petroleum ether (1:2)) to afford a compound of formula B (13.8 g, 56.5 mmol, 52.1%).

3. Preparation of a Compound of Formula C

A. A compound of formula C can be prepared according to the method described in U.S. Provisional Appl. No. 62/406,252. Briefly:

[Structure 6C: 4-bromo-6-methoxypyrazolo[1,5-a]pyridine-3-carbaldehyde (6C)]

A solution of 4-bromo-6-methoxypyrazolo[1,5-a]pyridine (5C) (5.0 g, 22 mmol) in DMF (220 mL) was cooled to 0° C. and then slowly treated with POCl₃ (6.2 mL, 66 mmol). The reaction was warmed to ambient temperature and stirred overnight. The reaction mixture was cooled to 0° C., quenched with water (220 mL), and basified with 6 M NaOH$_{(aq)}$ to pH 9-10. The reaction mixture was stirred for 1 h and then vacuum filtered. The solids were rinsed sequentially with water (3×50 mL) and MTBE (3×50 mL). The collected solid was suspended in DCM (500 mL) and stirred in a sonicating bath for 30 min and then vacuum filtered. The filtrate was retained, while the filter cake was taken up in water (300 mL) and extracted with DCM. The organic extracts, along with the retained DCM filtrate, were combined and dried over anhydrous Na₂SO₄, then filtered and concentrated in vacuo to provide the title compound (4.84 g, 86% yield). MS (apci), m/z=256.9 (M+H).

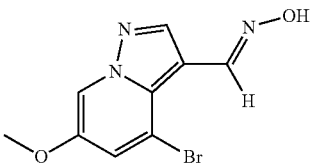

4-bromo-6-methoxypyrazolo[1,5-a]pyridine-3-carbaldehyde oxime (7C)

To a suspension of 4-bromo-6-methoxypyrazolo[1,5-a]pyridine-3-carbaldehyde (6C) (4.84 g, 19.0 mmol) in EtOH (253 mL) at ambient temperature was added water (127 mL) and hydroxylamine hydrochloride (1.98 g, 28.5 mmol). After stirring at 50° C. overnight, the reaction mixture was cooled to ambient temperature and concentrated in vacuo. The residue was suspended in water (150 mL) and then quenched slowly with saturated NaHCO$_{3(aq)}$ (30 mL). After stirring for 1 hour at ambient temperature the suspension was vacuum filtered and the filter cake rinsed sequentially with H$_2$O (500 mL) and MTBE (100 mL) to yield the title compound as a 2:1 E/Z mixture (5.13 g, quantitative yield), which was used in the next step without further purification. MS (apci) m/z=271.9 (M+H).

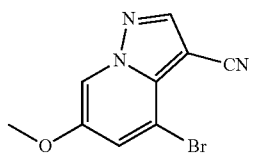

4-bromo-6-methoxypyrazolo[1,5-a]pyridine-3-carbonitrile (C)

The E/Z mixture of 4-bromo-6-methoxypyrazolo[1,5-a]pyridine-3-carbaldehyde oxime (7C) (4.95 g, 18.33 mmol) in acetic anhydride (172.9 mL, 1833 mmol) was stirred at 140° C. for 25 h, and then cooled to ambient temperature. The resulting suspension was further cooled in an ice bath for 15 min and then vacuum filtered and rinsed sequentially with water (200 mL) and MTBE (300 mL) to provide the title compound (3.74 g, 81% yield). $^1$H NMR (d$_6$-DMSO): δ 8.70 (s, 1H), 8.60 (s, 1H), 7.78 (s, 1H), 3.83 (s, 3H).

4. Preparation of the Compound of Formula I

A. From a Compound of Formula A

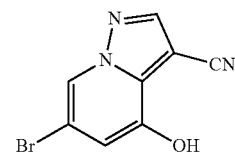

6-bromo-4-hydroxypyrazolo[1,5-a]pyridine-3-carbonitrile (18)

To a solution of 6-bromo-4-methoxypyrazolo[1,5-a]pyridine-3-carbonitrile (A) (20.8 kg, 82.5 mol) in DMF (200 kg) was added an aqueous solution of NaOH (6.6 kg in 13.5H$_2$O) in one portion at 40° C. 1-dodecanethiol (33.5 kg, 165 mol) was added to the solution at 40-45° C. and the reaction mixture was stirred at 50° C. for 16 h. HPLC showed the reaction was complete. The reaction mixture was poured into water (900 kg) at 0-5° C., followed by 10% aqueous citric acid monohydrate, which was used to adjust the pH to 5-6. The mixture was extracted with ethyl acetate (400 L×3). The combined organic layers were washed with brine and concentrated under reduced pressure. The residue was suspended in n-heptane (80 kg) and filtered, and the filter cake was washed with n-heptane (20 kg×2) and dried to give 18 (17.8 kg, 90.8%) as a yellow solid. $^1$H NMR (400 MHz, DMSO-d$_6$) δ (ppm): 8.75 (s, 1H), 8.51 (s, 1H), 6.84 (d, 1H).

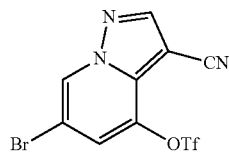

6-bromo-3-cyanopyrazolo[1,5-a]pyridin-4-yl trifluoromethanesulfonate (19)

To a solution of 6-bromo-4-hydroxypyrazolo[1,5-a]pyridine-3-carbonitrile (18) (17.8 kg, 74.8 mol) in DMF (170 kg) was added DIPEA (19.0 kg, 147 mol) in portions at −5-5° C. N,N-bis(trifluoromethylsulfonyl)aniline (26.2 kg, 73.5 mol) was added in portions to the above solution at −5-0° C. The reaction mixture was stirred at 0° C. for 1 h. TLC (pet. Ether:ethyl acetate, 2:1, R$_F$=0.5) showed the reaction was complete. The reaction was quenched by the addition of H$_2$O (500 kg) and a suspension formed. The solid was obtained by filtration and then dissolved in ethyl acetate (300 L) and brine (70 L). The organic layer was concentrated to 30 L and n-heptane (80 kg) was added. The suspension was stirred at 30° C. for 0.5 h, then filtered. The solid was washed with n-heptane (20 kg×2), dried to give 19 (22.5 kg, 81.0%) as a white solid. $^1$H NMR (400 MHz, CDCl$_3$) δ (ppm): 8.768 (s, 1H), 8.321 (s, 1H), 7.60 (s, 1H), 3.84 (s, 3H).

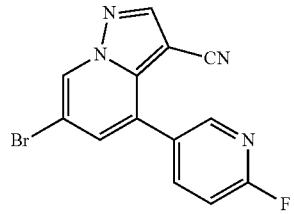

6-bromo-4-(6-fluoropyridin-3-yl)pyrazolo[1,5-a]pyridine-3-carbonitrile (20a)

To a solution of 6-bromo-3-cyanopyrazolo[1,5-a]pyridin-4-yl trifluoromethanesulfonate (19) (21.5 kg, 58 mol), 2-fluoro-5-(tetramethyl-1,3,2-dioxaborolan-2-yl)pyridine (12) (12.9 kg, 58 mol) and Pd(dppf)Cl$_2$-DCM (1.4 kg, 1.7 mol) in THF (400 kg) under an N$_2$ atmosphere was added an aqueous solution of potassium acetate (11.5 kg in 100 kg of water) at 10° C. The reaction mixture was stirred at 25-30° C. for 48 h. HPLC showed the reaction was complete. The reaction was quenched by the addition of water (150 kg) and the suspension was filtered. The solid was suspended in MeOH (200 L) and the suspension was stirred at 25-30° C. for 0.5 h and filtered. The filter cake was washed with MeOH (50 L) and dried to give the crude product (17 kg), which was purified by re-crystallization to give 20a (15.03 kg, 81.6%) as a white solid. The recrystallization process was as follows: To a solution of the crude product 20a (17 kg) in THF (600 L) at 60° C. was added DMF (36 kg). The mixture was stirred at 60° C. for 0.5 h. The mixture was cooled to 20° C. and water (300 L) was added, followed by filtration. The filter cake was washed with water (100 L) and dried to give compound 20 (15.0 kg, 82%). $^1$H NMR (DMSO-d$_6$, 40 MHz) δ (ppm): 9.48 (s, 1H), 8.73 (s, 1H), 8.51 (s, 1H), 8.25-8.29 (m, 1H), 7.86 (d, 1H), 7.38-7.41 (m, 1H). HPLC: 99.33%. MS: [M]=316.8, [M+2]=318.8.

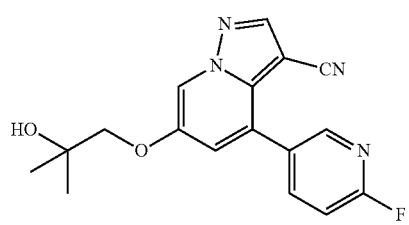

4-(6-fluoropyridin-3-yl)-6-(2-hydroxy-2-methyl-propoxy)pyrazolo[1,5-a]pyridine-3-carbonitrile (13a)

Direct Synthesis:

To a reaction vessel was charged 6-bromo-4-(6-fluoropyridin-3-yl)pyrazolo[1,5-a]pyridine-3-carbonitrile (20a) (7.8 kg, 5.68 mol), p-dioxane (28 L), water (9.5 L) and Cs$_2$CO$_3$ (5.55 kg, 17.03 mol). The mixture was agitated and purged with N$_2$ for not less than 30 min. To the flask was charged di-tert-butyl(2',4',6'-triisopropyl-3,4,5,6-tetramethyl-[1,1'-biphenyl]-2-yl)phosphane (436 g, 908 mmol), Pd$_2$(dba)$_3$ (208 g, 227 mmol) and p-dioxane (0.8 L). The mixture was agitated and purged with N$_2$ for not less than 30 min and then 2,2-dimethyloxirane (5.04 L, 56.8 mol) was charged and the reaction was heated to 72° C. overnight and the next day. The reaction was sampled to show the reaction was complete. The heating was terminated and the reaction was allowed to cool. When the internal temperature was ~40° C., Darco G60 (180 g) was added. The reaction was stirred (while continuing to cool) for not less than 1 h. When the reaction mixture was ~30° C. it was filtered over Celite (2.7 kg). The Celite cake was rinsed with ethyl acetate (7.2 L×5). The mixture was diluted with water (18 L) and the phases were separated. The organic layer was washed with 1:1 water/brine (36 L). The layers were separated. The aqueous layers were combined and extracted with ethyl acetate (18 L). The layers were separated and the organic layers were concentrated to 18 L (bath temperature 35° C.). To the organic layer was charged Silicycle (2.3 kg) and charcoal (1.8 kg). The mixture was heated to 50° C. and stirred overnight. The reaction was cooled to ambient temperature and then filtered over Celite (2.2 kg). The Celite cake was rinsed with ethyl acetate (10.8 L and then 14.4 L).

The solvent was removed under vacuum until there was a total of ~3.6 L. A charge of MTBE (3.6 L) was made and the solvent was concentrated to 3.6 L. This step was repeated two more times and the mixture stirred at ambient temperature overnight. The mixture was filtered and the filter cake was rinsed with MTBE (3.6 L×2). The solids were transferred to a vacuum oven and dried to give 13 (1085 g, 89 wt %, 56% corrected yield).

Step-Wise Synthesis:

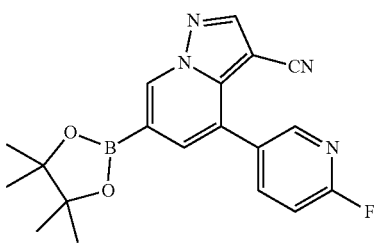

4-(6-fluoropyridin-3-yl)-6-(4,4,5,5-tetramethyl-1,3,2-dioxaborolan-2-yl)pyrazolo[1,5-a]pyridine-3-carbonitrile (22a)

A reaction flask charged with 6-bromo-4-(6-fluoropyridin-3-yl)pyrazolo[1,5-a]pyridine-3-carbonitrile (20a) (50.2 g, 153 mmol), bis(pinacolato)diboron (40.9 g, 161 mmol), and potassium acetate (45.2 g, 460 mmol) were slurried in DMSO (395 mL, 0.4 M) and then sparged with argon for 10 minutes. The reaction mixture was then treated with Pd(dppf)Cl$_2$-DCM (1.25 g, 1.54 mmol) and sparged with argon for an additional 10 minutes. The reaction mixture was heated to 70° C. for 16 h under a backflow of N$_2$ and then cooled to room temperature. The mixture was then diluted with ethyl acetate (2 L) and water (2 L). The biphasic mixture was stirred for 1 h and then the solids were removed by filtration and the cake was washed with ethyl acetate (250 mL). The layers were separated and the aqueous layer was extracted with ethyl acetate (1 L). The combined organic layers were washed with water (1 L×2) and then brine (1×250 mL). The organic layer was dried with Na$_2$SO$_4$ and filtered. The filtrate was treated with 15 g of Si-Thiol resin and stirred for 16 h. The solids were removed by filtration and the cake was washed with ethyl acetate. The organic layers were concentrated under vacuum to give 22a (54.1 g, 85.8 wt %). Compound 22a was used directly in the next step.

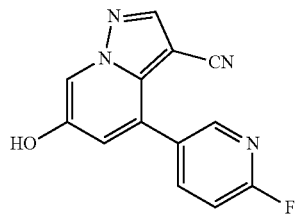

4-(6-fluoropyridin-3-yl)-6-hydroxypyrazolo[1,5-a]pyridine-3-carbonitrile (23a)

4-(6-fluoropyridin-3-yl)-6-(4,4,5,5-tetramethyl-1,3,2-dioxaborolan-2-yl)pyrazolo[1,5-a]pyridine-3-carbonitrile (22a) (54.1 g, 127.5 mmol) was dissolved in THF (750 mL, 0.2 M) and cooled to ~3° C. under a backflow of N₂. The reaction mixture was then treated with sodium hydroxide (319 mL, 637 mmol) and allowed to cool back to ~3° C. The mixture was treated dropwise with chilled (~2° C.) 35% hydrogen peroxide (89 mL, 1.02 mol) at a rate of ~1 drop every 2 seconds. The mixture was stirred for 4 h after complete addition of peroxide. To drive the reaction to completion an additional 1.0 equiv. of H₂O₂ was added and the mixture stirred at ~3° C. for an additional 1 h. The reaction mixture was then treated dropwise at a rate of ~2 drops per second with sodium thiosulfate (382 mL, 1.1 mol) at 3° C. and then allowed to slowly warm to room temp and stir for 16 h. The mixture was diluted with MTBE (1.5 L) and water (500 mL) and stirred at room temperature for 30 minutes. The layers were separated and the organic layer was washed with 0.1 M NaOH (200 mL). The combined aqueous layers were extracted with MTBE (500 mL). The aqueous layer was then acidified to pH~5 using solid citric acid and then diluted with water (1 L) and allowed to stir for 1 h. The solids were filtered, rinsed with additional water (~200 mL), and dried under vacuum for ~60 h to give 23a (25.6 g, 81%).

Tert-butyl-3-(5-(3-cyano-6-(2-hydroxy-2-methyl-propoxy)pyrazolo[1,5-a]pyridin-4-yl)pyridin-2-yl)-3,6-diazabicyclo[3.1.1]heptane-6-carboxylate (15a)

A reactor was charged with 4-(6-fluoropyridin-3-yl)-6-(2-hydroxy-2-methylpropoxy)pyrazolo[1,5-a]pyridine-3-carbonitrile (13a) (50 g, 153 mmol), tert-butyl 3,6-diazabicyclo[3.1.1]heptane-6-carboxylate (14a) (42.5 g, 215 mmol), DMSO (200 mL), and KOAc (30.1 g, 306 mmol). The reaction was heated to 75° C. with agitation for 24 h. The batch was cooled to ~15° C., and water (50 mL) was added at a rate to keep the internal temperature <35° C. and the mixture was stirred for 30 min. The suspension was filtered and the cake was washed with 30% DMSO/water (200 mL) and then water (200 mL). Acetone (200 mL) was charged to the cake and after 2 h the solid was transferred to a vacuum oven and dried at 45° C. to give 15a (66.2 g, 87%).

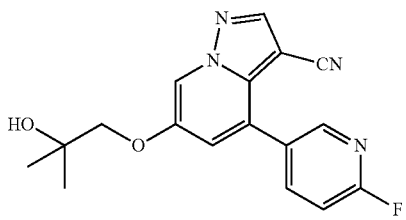

13a 4-(6-fluoropyridin-3-yl)-6-(2-hydroxy-2-methyl-propoxy)pyrazolo[1,5-a]pyridine-3-carbonitrile (13a)

4-(6-fluoropyridin-3-yl)-6-hydroxypyrazolo[1,5-a]pyridine-3-carbonitrile (23a) (2.46 g, 9.68 mmol) was dissolved in DMF (48 mL, 0.2 M) and cooled to 0° C. The mixture was then treated with sodium hydroxide (4.98 ml, 9.97 mmol) and stirred at 0° C. for 15 minutes and then treated with isobutylene oxide (8.50 ml, 96.8 mmol), sealed, and heated to 80° C. for 48 h. The mixture was cooled to room temperature, diluted with water (500 mL) and acidified to pH~5 using solid citric acid and stirred for 30 minutes. The mixture was extracted with ethyl acetate (500 mL×2). The combined organic layers were washed with water (250 mL×2), brine (100 mL) and dried over Na₂SO₄, filtered, and concentrated. The concentrate was purified by silica gel chromatography (1 to 50% DCM/acetone) to give 13a (1.94 g, 61%).

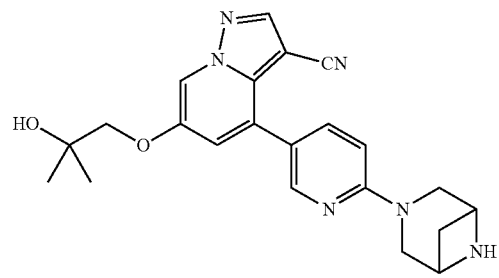

16

4-(6-(3,6-diazabicyclo 13.1.11 heptan-3-yl)pyridin-3-yl)-6-(2-hydroxy-2-methylpropoxy)pyrazolo[1,5-a]pyridine-3-carbonitrile (16)

To a reactor was charged tert-butyl-3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (15a) (80 g, 159 mmol) and 5% IPA/water (320 mL). The reaction was heated to 45° C. To the reaction was charged H₂SO₄ (35 mL, 634 mol) at a rate to keep the internal temperature below 60° C. The reaction mixture was aged at 45° C. for 2 h and then cooled to <30° C. Isopropyl alcohol (IPA, 720 mL) was slowly added over 5 minutes and the reaction stirred for not less than 1 h. The suspension was filtered and the cake was rinsed with IPA (160 mL), then 1:1 IPA/MTBE (160 mL) and then MTBE (160 mL×2). The cake was dried in a vacuum oven at 45° C. to give 16 as an off-white solid (70.4 g, 92 wt %, 74% adjusted yield).

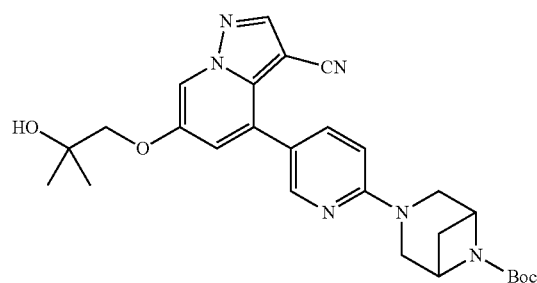

15a

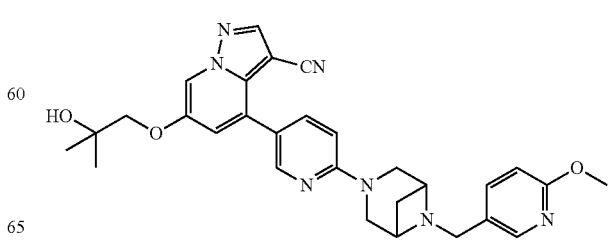

I

6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (I)

To a reactor was charged 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile (16) (15 g, 25 mmol), 6-methoxynicotinaldehyde (5.14 g, 25.0 mmol), DCM (150 mL), and TEA (12.2 mL, 87.4 mmol). To the reaction mixture was charged (in two portions) sodium triacetoxy borohydride (STAB) (10.6 g, 50.0 mmol). The reaction was stirred at room temperature overnight. To the reaction was charged an additional portion of STAB (2.65 g, 12.5 mmol). The reaction was stirred for an additional 2 h at ambient temperature and was judged complete by HPLC analysis. The reaction mixture was diluted with water (150 mL) and DCM (225 mL) and the layers were separated. The organic layer was washed with 1:1 water/sat. NaHCO$_3$ (2×150 mL) and 1:1 water/brine (150 mL). The organic layer was concentrated under vacuum to ~300 mL and then heated to ~32° C. to produce a homogenous solution. Heptane (105 mL) was slowly added and the suspension was allowed to cool to 25° C. An additional charge of heptane (195 mL) was made and the suspension was stirred at room temperature for 3 h. The solids were collected by filtration and the cake was rinsed with heptane (30 mL×2) and MTBE (30 mL×2). The cake was dried in a vacuum oven at 45° C. to give the compound of Formula I as an off-white solid (10.5 g). The compound of Formula I was recrystallized as follows. To a reaction flask was charged I (10.1 g) and DMSO (110 mL). The mixture was heated to 50° C. until all of the solid was in solution. The mixture was cooled to 25° C. and polish filtered. DMSO (10 mL) was charged through the filter as a wash. The resulting solution was heated to 45° C. and water (5 mL) was slowly added. The mixture was stirred for 30 minutes and a seed bed formed. Water (25 mL) was added over 1 h and the slurry was aged at 45° C. for an additional 1 h. The slurry was then allowed to cool to 25° C. and stir for 2 h. The slurry was filtered and the cake was washed with water (20 mL×3), MeOH (20 mL×2) and MTBE (20 mL×2). The cake was dried at room temperature in a vacuum oven to give 9.35 g (74%) of the compound of Formula I. MS (apci) m/z=526.2 (M+H). $^1$H NMR (400 MHz, DMSO-d$_6$) δ: 8.64 (d, 1H, J=2.3 Hz), 8.55 (s, 1H), 8.38 (d, 1H, J=2.3 Hz), 8.04 (d, 1H, J=2.3 Hz), 7.80 (dd, 1H, J=8.6, 2.3 Hz), 7.64 (dd, 1H, J=8.6, 2.3 Hz), 7.27 (d, 1H, J=2.0 Hz), 6.76 (d, 1H, J=8.6 Hz), 6.73 (d, 1H, J=8.2 Hz), 4.67 (s, 1H), 3.85 (s, 2H), 3.79 (s, 3H), 3.72 (d, 2H, J=12.5 Hz), 3.64 (d, 2H, J=5.9 Hz), 3.51 (br d, 2H), 3.47 (s, 2H), 2.47 (m, 1H), 1.55 (d, 1H), 1.20 (s, 6H).

B. From a Compound of Formula A

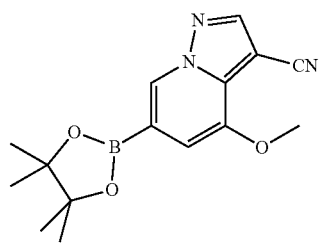

32a

4-methoxy-6-(4,4,5,5-tetramethyl-1,3,2-dioxaborolan-2-yl)pyrazolo[1,5-a]pyridine-3-carbonitrile (32a)

To a reaction vessel was charged 6-bromo-4-methoxypyrazolo[1,5-a]pyridine-3-carbonitrile (A) (200 g, 793.4 mmol), KOAc (233.6 g, 2.38 mol), 4,4,4',4',5,5,5',5'-octamethyl-2,2'-bi(1,3,2-dioxaborolane) (261.9 g, 1.03 mol), and p-dioxane (3000 mL). The reaction was degassed for 20 minutes at ambient temperature. To the reaction was charged Pd(dppf)DCM (12.96 g, 15.87 mmol). The reaction was degassed for 20 minutes at ambient temperature and then heated to 75° C. overnight. The reaction was cooled to ambient temperature, charcoal (20 g) was charged and the suspension stirred at ambient temperature for >2 hours. The mixture was filtered over celite (200 g) and the cake was rinsed with EtOAc (7×400 mL). The mixture was added to a reactor and then washed with water (2000 mL). The aqueous layer was removed and the organic layer was washed with 3:1 water/brine (2000 mL) and then 1:1 water/brine (2000 mL). The first aqueous layer was back extracted with EtOAc (1000 mL). The combined organic layers were added to a flask and silicycle-thiol (240 g) and charcoal (100 g) were added. The suspension was heated to 50° C. and stirred overnight. The reaction was cooled to below 30° C. and was filtered over celite (250 g). The cake was rinsed with EtOAc (6×400 mL). The filtrate was distilled under vacuum with heating to a set volume and a thick slurry formed. Heptane was slowly added over ~10 minutes (400 mL) to the slurry and the mixture was distilled back down to a set volume. An additional charge of heptane (400 mL) was made and the distillation continued until a set volume was reached. The vacuum was removed and the heating discontinued. Heptane (200 mL) and MTBE (50 mL) were added and the suspension was stirred overnight. After stirring overnight, it appeared that solvent was lost and heptane (1250 mL) was slowly added. The suspension was aged at ambient temperature for ~10 minutes and was then filtered. The cake was rinsed with heptane (2×200 mL) and dried at ambient temperature by pulling air through it to give 32a (168.2 g, 87 wt %, 62% corrected yield).

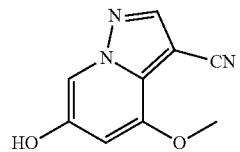

33

6-Hydroxy-4-methoxypyrazolo[1,5-a]pyridine-3-carbonitrile (33)

To a flask was charged 4-methoxy-6-(4,4,5,5-tetramethyl-1,3,2-dioxaborolan-2-yl)pyrazolo[1,5-a]pyridine-3-carbonitrile (32a) (100.0 g, 334.3 mmol), NMO (78.3 g, 668.6 mmol, 2 eq), and THF (1000 mL, 10 vol). The reaction was heated to 50° C. for 1 hour and then additional NMO (19.5 g, 167 mmol, 0.5 eq) was charged. After 1 hour, an additional charge of NMO (19.5 g, 167 mmol, 0.5 eq) was made and the reaction was heated to 45° C. overnight. After stirring overnight, the reaction was heated back to 50° C. and NMO (40 g, 334 mmol, 1 eq) was charged. After heating for 5 hours, the reaction was distilled to a total volume of 600 mL (internal temperature was held between 42° C. and 50° C. during distillation). The mixture was cooled to 40° C. and water (1800 mL total, 18 vol) was added. A suspension was produced and additional water (500 mL) was added. The thick slurry was aged at ambient temperature overnight and then the suspension was filtered. The cake was washed with water (250 mL) and heptane (250 mL) and the solid dried under vacuum at 50° C. overnight to give 33 (49.6 g, 95.3 wt %, 85.9% corrected yield based on 87 wt % 32a).

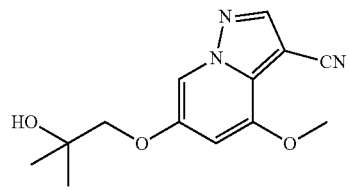

34

6-(2-Hydroxy-2-methylpropoxy)-4-methoxypyrazolo[1,5-a]pyridine-3-carbonitrile (34)

To a flask was charged 6-hydroxy-4-methoxypyrazolo[1,5-a]pyridine-3-carbonitrile (33) (10.00 g, 52.86 mmol) and THF (50.0 mL, 5 vol). NaOH (28 mL, 2M) was added in one portion and after stirring for ~5 minutes, 2,2-dimethyloxirane (23.5 mL, 264.3 mmol) was added, the reaction was heated to 60° C., and then stirred overnight. The reaction was cooled to room temperature, THF (10.0 mL) was added, and then water (200 mL) was slowly added. A suspension was produced and additional water (25 mL) was added. The solid was filtered, the cake was washed with water (3×20 mL), heptane (20 mL), and dried under vacuum at 50° C. to give 34 (10.273 g, 96.2 wt %, 75.1% corrected yield based on 95 wt % 33).

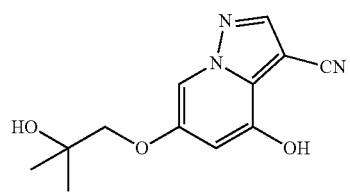

35

4-Hydroxy-6-(2-hydroxy-2-methylpropoxy)pyrazolo[1,5-a]pyridine-3-carbonitrile (35)

To flask was charged 6-(2-hydroxy-2-methylpropoxy)-4-methoxypyrazolo[1,5-a]pyridine-3-carbonitrile (34) (8.00 g, 30.62 mmol) and DMA (40 mL, 5 vol). NaOH (2.40 mL, 50 wt %) was added and the mixture heated to 30° C. Dodecane-1-thiol (11.1 mL, 45.93 mmol) was added and the mixture was heated to 60° C. The reaction was called complete and the heating was discontinued. Water (24 mL, 3 vol) was added to the reaction (~60° C.) and the mixture was allowed to cool to room temperature. The reaction mixture was slowly added (temperature <20° C. during addition) to 15 wt % citric acid (160 mL), precooled to 10° C. The solids were filtered, the cake was washed with water (2×16 mL), heptane (3×16 mL) and dried under vacuum at 50° C. overnight to give 35 (6.333 g, 93 wt %, 81% corrected yield based on 96 wt % 34).

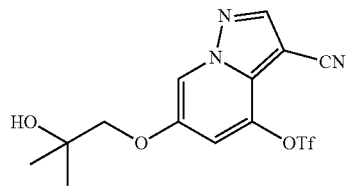

36

3-Cyano-6-(2-hydroxy-2-methylpropoxy)pyrazolo[1,5-a]pyridin-4-yl trifluoromethanesulfonate (36)

To a flask was charged 4-hydroxy-6-(2-hydroxy-2-methylpropoxy)pyrazolo[1,5-a]pyridine-3-carbonitrile (35) (3.31 g), 1,1,1-trifluoro-N-phenyl-N-((trifluoromethyl)sulfonyl)methanesulfonamide (4.79 g), and DMA (33 mL, 10 vol). DIEA (4.67 mL) was added and after 10 minutes the reaction judged complete. The reaction mixture was slowly (maintaining the temperature <20° C.) added to HOAc (0.92 mL, 1.2 eq) in water (33 mL) that was precooled to 15° C. (ice/water bath). The slurry was stirred for 15 minutes and the solids were filtered, the cake was washed with water (3×7 mL), heptane (2×7 mL), and then dried under vacuum at 50° C. to give 36 (3.517 g, 99.4 wt %, 68.9% yield (uncorrected)).

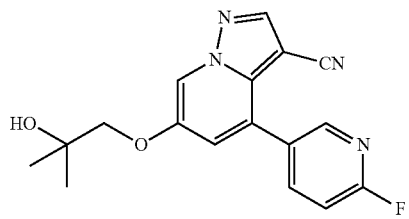

13

4-(6-fluoropyridin-3-yl)-6-(2-hydroxy-2-methylpropoxy)pyrazolo[1,5-a]pyridine-3-carbonitrile (13)

To a flask was charged 3-cyano-6-(2-hydroxy-2-methylpropoxy)pyrazolo[1,5-a]pyridin-4-yl trifluoromethanesulfonate (36) (3.00 g, 7.91 mmol), 2-fluoro-5-(4,4,5,5-tetramethyl-1,3,2-dioxaborolan-2-yl)pyridine (1.85 g, 8.30 mmol), and THF (60 mL, 20 vol). The solution was purged with nitrogen for 15 minutes and PdCl$_2$(dppf)DCM (452 mg, 0.553 mmol) was charged and the mixture was purged with nitrogen for an additional 5 minutes. To a separate flask was added KOAc (1.55 g, 15.82 mmol) and water (15 mL). This mixture was purged with nitrogen for 2 minutes and then added to the reaction mixture, which was purged with nitrogen for an additional 5 minutes. The reaction stirred overnight at ambient temperature. The reaction mixture was poured onto MTBE (60 mL) and water (45 mL). The layers were separated and the organic layer was washed with water (30 mL) followed by 3:1 water/brine (30 mL). The first and second aqueous layers were combined and back extracted with MTBE (30 mL). The organic layers were combined and concentrated to a solid. The solid was taken up in MTBE (30 mL) and after stirring for 2 hours at ambient temperature the suspension was filtered, the cake washed with heptane (3×6 mL) and the solids dried under vacuum to give 13 (1.69 g, 65% yield). Compound 13 was converted to the compound of Formula I as described above.

C. From a Compound of Formula B

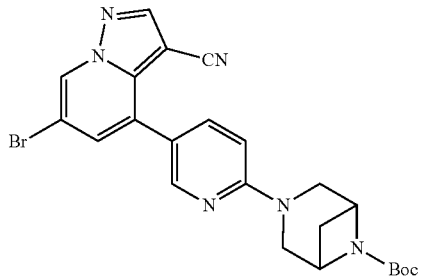

25a

Tert-butyl 3-(5-(6-bromo-3-cyanopyrazolo[1,5-a]
pyridin-4-yl)pyridin-2-yl)-3,6-diazabicyclo[3.1.1]
heptane-6-carboxylate (25a)

A solution of 4,6-dibromopyrazolo[1,5-a]pyridine-3-carbonitrile (B) (0.295 g, 0.980 mmol) and tert-butyl 3-(5-(4,4,5,5-tetramethyl-1,3,2-dioxaborolan-2-yl)pyridin-2-yl)-3,6-diazabicyclo[3.1.1]heptane-6-carboxylate (24a) (0.413 g, 1.03 mmol) in DMF (9.8 mL, 0.980 mmol) was heated to 50° C. to solubilize all of the solids. The mixture was then cooled to room temperature. Aqueous $K_2CO_3$ (0.980 mL, 1.96 mmol) was slowly added and the mixture was purged with Ar gas for 5 min. Pd(dppf)Cl$_2$.CH$_2$Cl$_2$ (60 mg, 0.0735 mmol) was then added and the reaction stirred at room temperature over 48 h. LCMS indicated that the reaction was complete. Ethyl acetate and water were added to the mixture. The layers were separated and the organic layer was washed with water and brine and dried with Na$_2$SO$_4$. The organic layer was concentrated under vacuum and then purified using column chromatography (hexanes/ethyl acetate, 10-90%) to give 25a (0.332 g, 0.670 mmol, 68.4% yield).

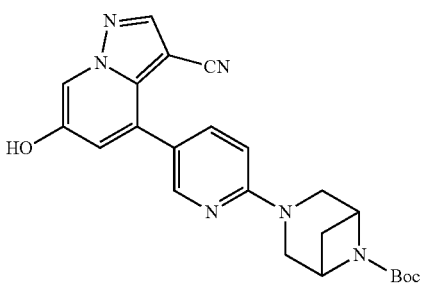

26a

Tert-butyl 3-(5-(3-cyano-6-hydroxypyrazolo[1,5-a]
pyridin-4-yl)pyridin-2-yl)-3,6-diazabicyclo[3.1.1]
heptane-6-carboxylate (26a)

Tert-butyl 3-(5-(6-bromo-3-cyanopyrazolo[1,5-a]pyridin-4-yl)pyridin-2-yl)-3,6-diazabicyclo[3.1.1]heptane-6-carboxylate (25a) (475 mg, 0.959 mmol) was dissolved in THF (10 mL, 0.1 M) and treated with bis(pinacolato)diboron (255 mg, 1.00 mmol), dichloro[1,1'-bis(diphenylphosphino) ferrocene]palladium (II)-dichloromethane (39 mg, 0.0479 mmol), and potassium acetate (282 mg, 2.88 mmol). The reaction mixture was sparged with argon, sealed, and heated to 70° C. for 16 h. The reaction was judged complete and the mixture was then cooled to 0° C. and treated with sodium hydroxide (4.8 mL, 4.79 mmol) then portion-wise treatment with hydrogen peroxide (0.49 mL×15, 7.35 mL) every 15 minutes. After complete addition of hydrogen peroxide the reaction mixture was allowed to slowly warm to room temperature and stir for 16 h. The reaction mixture was diluted with water and extracted with 4:1 DCM:IPA (2×). The aqueous layer was then acidified to pH~5 using AcOH and extracted with 4:1 DCM:IPA (2×). The combined organic layers were washed with water, dried over Na$_2$SO$_4$, filtered, and concentrated. The concentrate was purified by silica gel chromatography (5 to 75% DCM/acetone) to give 26a (314 mg, 75.7%).

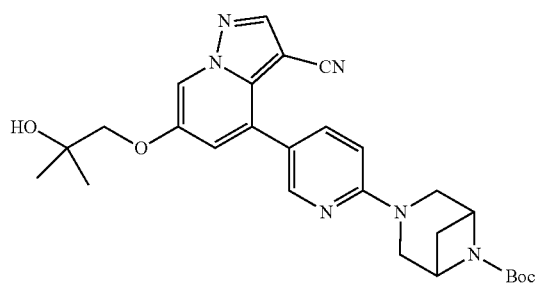

15a

Tert-butyl 3-(5-(3-cyano-6-(2-hydroxy-2-methyl-
propoxy)pyrazolo[1,5-a]pyridin-4-yl)pyridin-2-yl)-3,
6-diazabicyclo[3.1.1]heptane-6-carboxylate (15a)

Tert-butyl 3-(5-(3-cyano-6-hydroxypyrazolo[1,5-a]pyridin-4-yl)pyridin-2-yl)-3,6-diazabicyclo[3.1.1]heptane-6-carboxylate (26a) (312 mg, 0.721 mmol) was dissolved in DMF (4.8 mL, 0.15 M) and treated with sodium hydroxide (794 µL, 0.794 mmol). The reaction mixture was stirred for 10 minutes then treated with isobutylene oxide (634 µL, 7.21 mmol), sealed, and heated to 80° C. for 16 h. The reaction mixture was cooled to room temperature, diluted with water (100 mL) and stirred for 30 minutes. The solid was filtered and rinsed with water to give 15a (304 mg, 84%) as a light tan solid. Compound 15a was converted to the compound of Formula I as described above (from a compound of formula A).

D. From a Compound of Formula C

The compound of Formula I can also be prepared according to the method described in U.S. Provisional Appln. No. 62/406,252. Briefly:

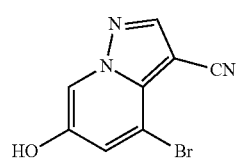

10

4-Bromo-6-hydroxypyrazolo[1,5-a]pyridine-3-car-
bonitrile (10)

A slurry of 4-bromo-6-methoxypyrazolo[1,5-a]pyridine-3-carbonitrile (C) (50.0 g, 198.4 mmol) in DCE (500 mL)

was treated with AlCl₃ (79.34 g, 595.1 mmol). Under an N₂(g) atmosphere, the resulting mixture was stirred for 19 h at 76° C. before cooling to room temperature. Using THF (1750 mL) as a rinse solvent, the reaction mixture was poured into a mechanically stirred suspension of sodium sulfate decahydrate (10 eq, 639 g) in THF (1000 mL). After stirring overnight at ambient temperature, the resulting suspension was filtered, and the solids were rinsed with additional THF (2×250 mL). The filtrate was concentrated in vacuo, and the resulting solid was dried under high vacuum for 3 days to afford the title compound (46.18 g, 98% yield) in sufficient purity for subsequent use. ¹H NMR (d⁶-DMSO): δ 10.48 (s, 1H), 8.58 (s, 1H), 8.38 (d, 1H), 7.64 (3, 1H).

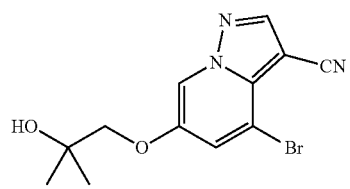

11

4-Bromo-6-(2-hydroxy-2-methylpropoxy)pyrazolo[1,5-a]pyridine-3-carbonitrile (11)

In a pressure vessel, a mixture of 4-bromo-6-hydroxy-pyrazolo[1,5-a]pyridine-3-carbonitrile (10) (10.0 g, 42.0 mmol) and K₂CO₃(s) (17.4 g, 126 mmol) in DMF (50 mL) was treated with 2,2-dimethyloxirane (36.9 mL, 420 mmol). After sealing the vessel, the reaction mixture was stirred for 12 h at 60° C., then for 12 h at 85° C. The mixture was allowed to cool to ambient temperature. The room temperature mixture was poured into water (400 mL), then stirred for 1 hour at ambient temperature. The resultant suspension was vacuum filtered and the filter cake was rinsed with water. The solids were collected and dried in vacuo to cleanly provide the title compound (11 g, 84% yield).

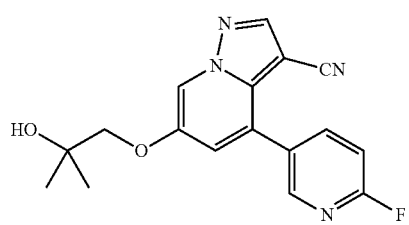

13a 4-(6-fluoropyridin-3-yl)-6-(2-hydroxy-2-methyl-propoxy)pyrazolo[1,5-a]pyridine-3-carbonitrile (13a)

A mixture of 4-bromo-6-(2-hydroxy-2-methylpropoxy)pyrazolo[1,5-a]pyridine-3-carbonitrile (11) (10.0 g, 32.2 mmol), 2-fluoro-5-(4,4,5,5-tetramethyl-1,3,2-dioxaborolan-2-yl)pyridine (10.8 g, 48.4 mmol) and Pd(PPh₃)₄ (1.12 g, 0.967 mmol) in dioxane (200 mL) was treated with 2 M Na₂CO₃(aq) (64.5 mL, 129 mmol). The resulting mixture was sparged with Ar(g), then stirred for 12 h at 85° C. under an atmosphere of N₂(g). After cooling to ambient temperature, the resultant mixture was poured into cold water (1.5

L). The pH of the mixture was adjusted to about pH 6 with the addition of 10% citric acid. After stirring for 1 hour at ambient temperature, the resultant suspension was vacuum filtered. The solids were collected and dried in vacuo to cleanly provide the title compound (10 g, 95% yield).

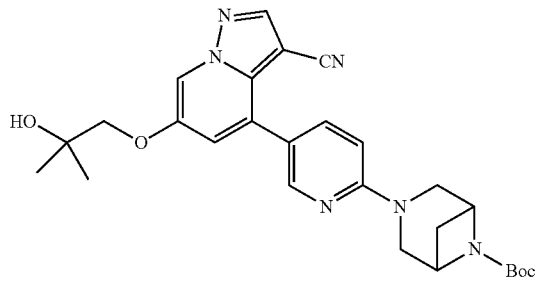

15a

Tert-butyl 3-(5-(3-cyano-6-(2-hydroxy-2-methyl-propoxy)pyrazolo[1,5-a]pyridin-4-yl)pyridin-2-yl)-3,6-diazabicyclo[3.1.1]heptane-6-carboxylate (15a)

A mixture of 4-(6-fluoropyridin-3-yl)-6-(2-hydroxy-2-methylpropoxy)pyrazolo[1,5-a]pyridine-3-carbonitrile (13a) (1.70 g, 8.55 mmol), 3,6-diaza-bicyclo[3.1.1]heptane-6-carboxylic acid tert-butyl ester (1.70 g, 8.55 mmol) and K₂CO₃(s) (7.88 g, 57.0 mmol) in DMSO (7 mL) was stirred for 12 h at 90° C. The resultant thick slurry was diluted with additional DMSO (2 mL) and stirred for 12 h at 90° C. The mixture was cooled to ambient temperature and diluted with water (100 mL). The aqueous mixture was washed with DCM. The combined organic extracts were dried over anhydrous MgSO₄(s), filtered and concentrated in vacuo. The crude residue was purified by silica chromatography (30-80% EtOAc/hexanes as the gradient eluent system) to cleanly provide the title compound (2.87 g, 100% yield). MS (apci) m/z=505.2 (M+H).

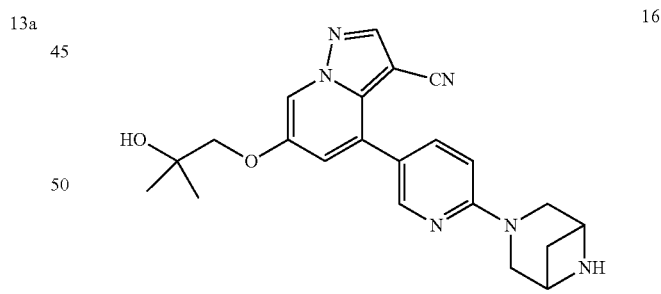

16

4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (16)

A solution of tert-butyl 3-(5-(3-cyano-6-(2-hydroxy-2-methylpropoxy)pyrazolo[1,5-a]pyridin-4-yl)pyridin-2-yl)-3,6-diazabicyclo[3.1.1]heptane-6-carboxylate (15a) (3.05 g, 6.04 mmol) in DCM (20 mL) was treated with 4 N HCl in dioxanes (15.1 mL, 60.4 mmol). The resulting mixture was stirred for 12 h at ambient temperature, and then concentrated in vacuo. The crude residue was diluted with DCM and toluene, and then sonicated before concentrating in vacuo to afford the title compound as the dihydrochloride salt (2.44 g, quantitative yield). MS (apci) m/z=405.2 (M+H).

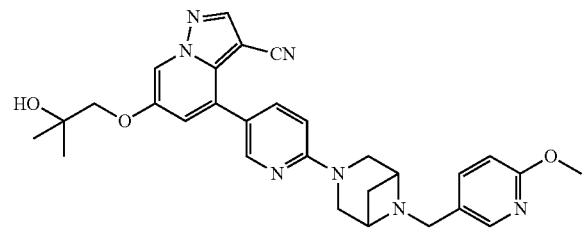

6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile (I)

A solution of 4-(6-(3,6-diazabicyclo[3.1.1]heptan-3-yl)pyridin-3-yl)-6-(2-hydroxy-2-methylpropoxy)pyrazolo[1,5-a]pyridine-3-carbonitrile dihydrochloride (16) (12.2 mg, 0.0277 mmol) in DCE (513 μL) was treated sequentially with 6-methoxynicotinaldehyde (7.59 mg, 0.0553 mmol) and NaBH(AcO)$_3$ (17.6 mg, 0.0830 mmol), then stirred overnight at ambient temperature. The mixture was concentrated in vacuo, and the residue was purified by silica chromatography (0-20% MeOH in DCM as the gradient eluent) to cleanly provide the title compound (13.59 mg, 93% yield). MS (apci) m/z=526.2 (M+H). $^1$H NMR (400 MHz, DMSO-d$_6$) δ: 8.64 (d, 1H, J=2.3 Hz), 8.55 (s, 1H), 8.38 (d, 1H, J=2.3 Hz), 8.04 (d, 1H, J=2.3 Hz), 7.80 (dd, 1H, J=8.6, 2.3 Hz), 7.64 (dd, 1H, J=8.6, 2.3 Hz), 7.27 (d, 1H, J=2.0 Hz), 6.76 (d, 1H, J=8.6 Hz), 6.73 (d, 1H, J=8.2 Hz), 4.67 (s, 1H), 3.85 (s, 2H), 3.79 (s, 3H), 3.72 (d, 2H, J=12.5 Hz), 3.64 (d, 2H, J=5.9 Hz), 3.51 (br d, 2H), 3.47 (s, 2H), 2.47 (m, 1H), 1.55 (d, 1H), 1.20 (s, 6H).

We claim:

1. A process for preparing a compound of Formula I

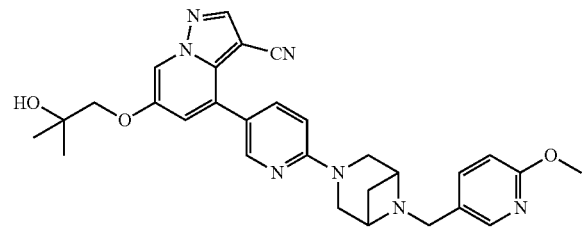

or a pharmaceutically acceptable salt thereof, wherein the process comprises treating a compound of formula 16

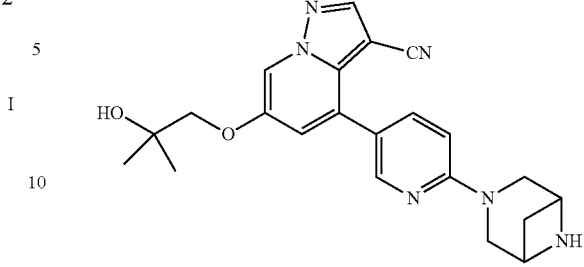

or a salt thereof with 6-methoxynicotinaldehyde and a reducing agent to form the compound of Formula I or a pharmaceutically acceptable salt thereof.

2. The process of claim 1, further comprising preparing the compound of formula 16, or a salt thereof, the process comprising treating a compound of formula 15

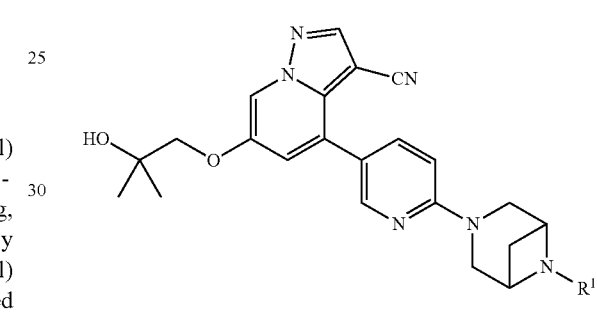

or a salt thereof, wherein R$^1$ is an amine protecting group, with a deprotecting agent to form the compound of formula 16 or a salt thereof.

3. The process of claim 2, further comprising preparing the compound of formula 15 or a salt thereof, wherein R$^1$ is an amine protecting group, comprising:
treating a compound of formula 13

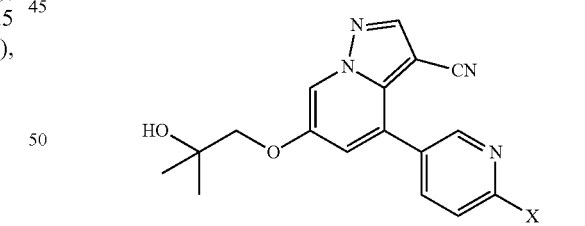

or a salt thereof, wherein X represents a halogen or a sulfonate, with a compound of formula 14

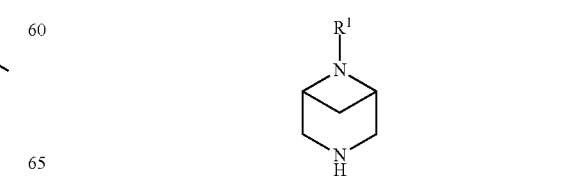

or a salt thereof, wherein R¹ is an amine protecting group, to form the compound of formula 15 or a salt thereof.

4. The process of claim 3, further comprising preparing the compound of formula 13 or a salt thereof, the process comprising treating a compound of formula 20

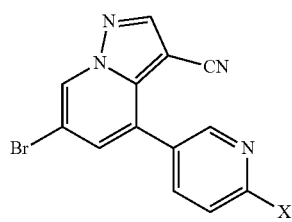

or a salt thereof, wherein X represents a halogen or a sulfonate, with a compound of formula 21

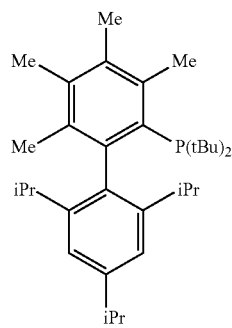

in the presence of 2,2-dimethyloxirane, a first catalyst comprising a metal, and a first weak base to form the compound of formula 13 or a salt thereof; and wherein preparing the compound of formula 20 or a salt thereof comprises treating a compound of formula 19

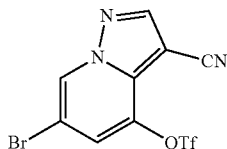

or a salt thereof with a compound of formula 12

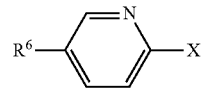

or a salt thereof, wherein X represents a halogen or a sulfonate and R⁶ represents a boronic acid or ester with the boron atom as the point of attachment to the pyridine ring of compound 12, in the presence of a eighth catalyst comprising a metal to form the compound of formula 20 or a salt thereof.

5. The process of claim 3, further comprising preparing the compound of formula 13 or a salt thereof, the process comprising:

treating a compound of formula 20 or a salt thereof with a first diboronic acid or ester in the presence of a second catalyst comprising a metal to form a compound of formula 22

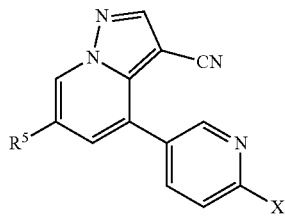

or a salt thereof, wherein X represents a halogen or a sulfonate and R⁵ represents a boronic acid or ester with the boron atom as the point of attachment to the pyrazolopyridine ring of compound 22 or a salt thereof;

treating the compound of formula 22 or a salt thereof with a first strong base and hydrogen peroxide to form a compound of formula 23

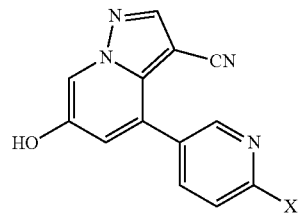

or a salt thereof, wherein X represents a halogen or a sulfonate; and treating the compound of formula 23 or a salt thereof with 2,2-dimethyloxirane in the presence of a second strong base to form the compound of formula 13 or a salt thereof; and wherein preparing the compound of formula 20 or a salt thereof comprises treating a compound of formula 19

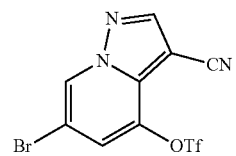

or a salt thereof with a compound of formula 12

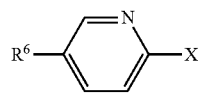

or a salt thereof, wherein X represents a halogen or a sulfonate and R⁶ represents a boronic acid or ester with the boron atom as the point of attachment to the pyridine ring of compound 12, in the presence of a eighth catalyst comprising a metal to form the compound of formula 20 or a salt thereof.

6. A process for preparing a compound of Formula I

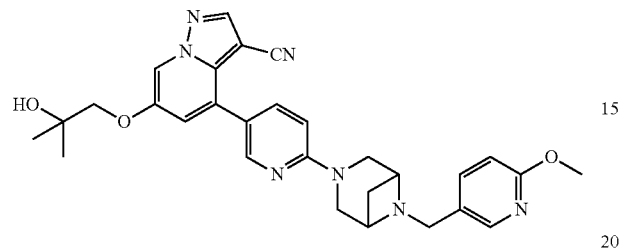

I or a pharmaceutically acceptable salt thereof, wherein the process comprises treating a compound of formula 29

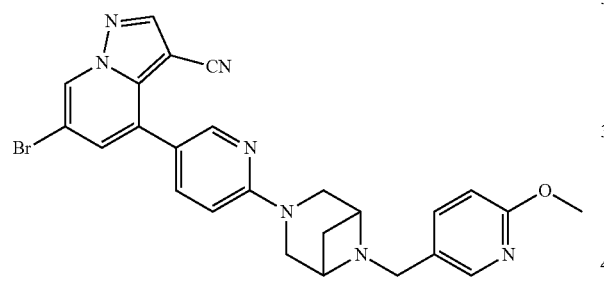

29 or a salt thereof with a compound of formula 21

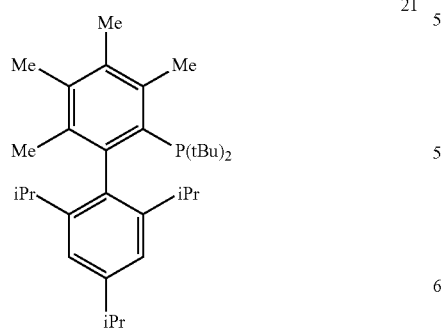

21 in the presence of 2,2-dimethyl dioxirane, a sixth catalyst comprising a metal, and a second weak base to form the compound of Formula I or a pharmaceutically acceptable salt thereof.

7. A process for preparing a compound of Formula I

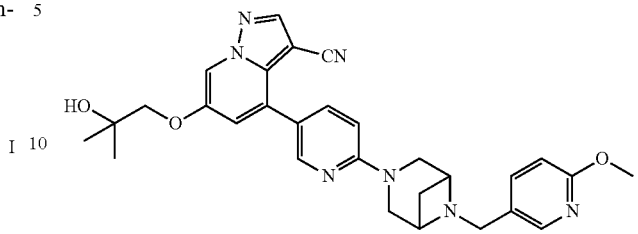

I or a pharmaceutically acceptable salt thereof, wherein the process comprises:

a) treating a compound of formula 29

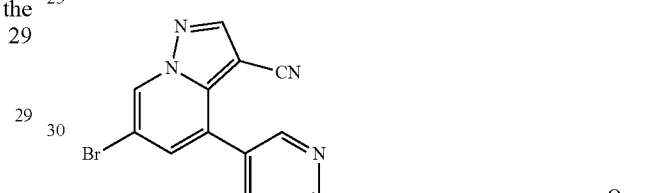

29 or a salt thereof with a third diboronic acid or ester in the presence of a seventh catalyst comprising a metal to form a compound of formula 30

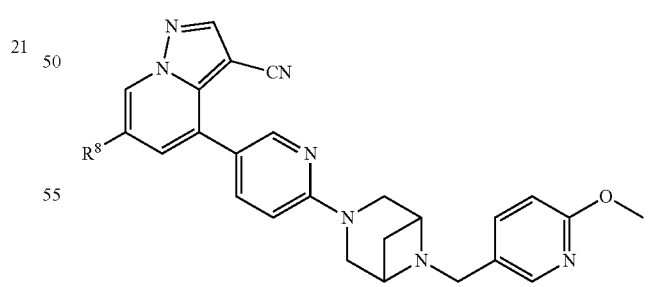

30 or a salt thereof, wherein R⁸ represents a boronic acid or ester with the boron atom as the point of attachment to the pyrazolopyridine ring of compound 30 or a salt thereof;

b) treating the compound of formula 30 or a salt thereof with a fourth strong base and hydrogen peroxide to form a compound of formula 31

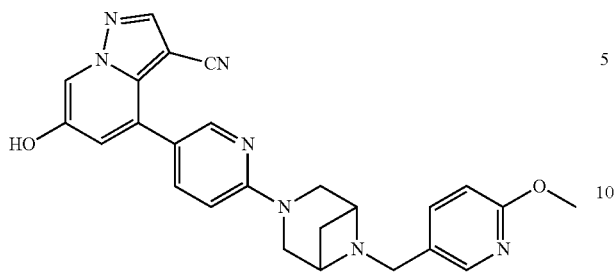

or a salt thereof; and c) treating the compound of formula 31 or a salt thereof with 2,2-dimethyloxirane in the presence of a fifth strong base to form the compound of Formula I or a pharmaceutically acceptable salt thereof.

8. The process of claim 6, further comprising preparing the compound of formula 29, the process comprising:

treating a compound of formula 19

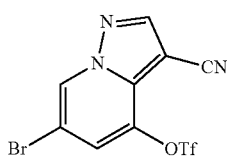

or a salt thereof with a compound of formula 28

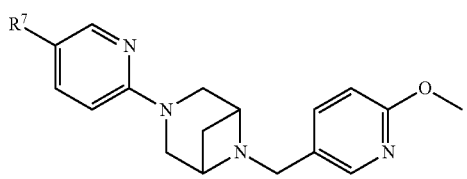

or a salt thereof, wherein $R^7$ represents a boronic acid or ester with the boron atom as the point of attachment to the pyridine ring of compound 28, in the presence of a fifth catalyst comprising a metal to form the compound of formula 29 or a salt thereof.

9. The process of claim 8, further comprising preparing the compound of formula 19 or a salt thereof, the process comprising:

treating a compound of formula A

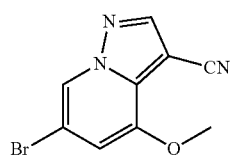

or a salt thereof with a second dealkylating agent to form a compound of formula 18

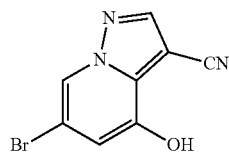

or a salt thereof; and treating the compound of formula 18 or a salt thereof with a second triflating reagent to form the compound of formula 19 or a salt thereof.

10. The process of claim 9, further comprising preparing the compound of formula A or a salt thereof by a process comprising:

a) treating a compound of formula 1a

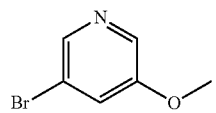

or a salt thereof with O-(mesitylsulfonyl)hydroxylamine to form a compound of formula 2a

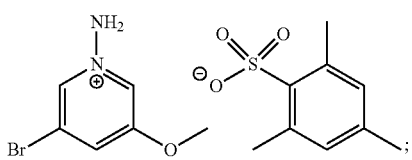

and b) treating the compound of formula 2a with acrylonitrile or an acrylonitrile derivative in the presence of a first non-nucleophilic base to form the compound of formula A; or, alternatively, treating a compound of formula 8A

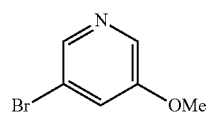

or a salt thereof with O-(2,4-dinitrophenyl)hydroxylamine to form a compound of formula 9A

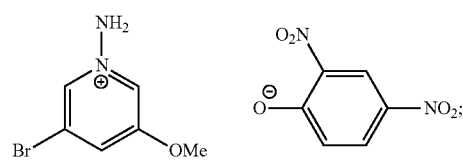

and b) treating the compound of formula 9A with acrylonitrile or an acrylonitrile derivative in the presence of a first non-nucleophilic base to form the compound of formula A.

11. The process of claim 2, further comprising preparing a compound of formula 15 or a salt thereof, wherein $R^1$ is an amine protecting group, comprising:
treating a compound of formula 26

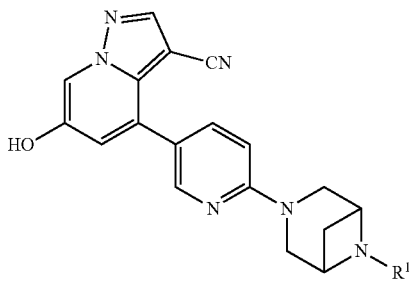

or a salt thereof, wherein $R^1$ is an amine protecting group, with 2,2-dimethyloxirane in the presence of a sixth strong base to form the compound of formula 15 or a salt thereof.

12. The process of claim 1, wherein the reducing agent is selected from the group consisting of an alkali metal borohydride, a hydrazine compound, citric acid, a citric acid salt, succinic acid, a succinic acid salt, ascorbic acid, and an ascorbic acid salt.

13. The process of claim 2, wherein the deprotecting agent is selected from the group consisting of trifluoroacetic acid, hydrochloric acid, hydrobromic acid, hydriodic acid, phosphoric acid, sulfuric acid, methanesulfonic acid, p-toluene sulfonic acid, acetyl chloride, aluminum trichloride, and boron trifluoride.

14. The process of claim 2, wherein $R^1$ is an amine protecting group selected from the group consisting of formyl, acetyl, trifluoroacetyl, benzyl, benzoyl, carbamate, benzyloxycarbonyl, p-methoxybenzyl carbonyl, tert-butyloxycarbonyl (Boc), trimethylsilyl, 2-trimethylsilyl-ethanesulfonyl, trityl and substituted trityl groups, allyloxycarbonyl, 9-fluorenylmethyloxycarbonyl, nitroveratryloxycarbonyl, p-methoxybenzyl, and tosyl.

15. The process of claim 5, wherein the first diboronic acid or ester is selected from the group consisting of an alkenyl boronic acid, an alkyl boronic acid, an aryl boronic acid, a heteroaryl boronic acid, and a pinacol boronic ester.

16. The process of claim 9, wherein the second dealkylating agent is selected from the group consisting of boron trihalides, organoboranes, triiodides, trialkylsilyl halides, hexafluorosilicate, aluminum trihalides, lithium halides, hydrogen halides, iron trihalides, tin tetrahalides, titanium tetrahalides, thiolates and amides.

17. The process of claim 10, wherein the first non-nucleophilic base is selected from the group consisting of triethylamine (TEA), diisopropylethylamine (DIPEA), N-methylmorpholine (NMM), tri-tert-butylpyrimidine (TTBP), 1,4-diazabicyclo-[2.2.2]octane (DABCO), 1,8-diazabicyclo[5.4.0]undec-7-ene (DBU), N,N-diethylaniline, pyridine, 2,6-lutidine, 2,4,6-collidine, 4-dimethylaminopyridine, quinuclidine, 2,6-di-tert-butylpyridine, tert-butylphosphazene, lithium diisopropylamide, sodium bis(trimethylsilyl)amide, potassium bis(trimethylsilyl)amide, lithium tetramethylpiperidide, sodium hydride, potassium hydride, sodium tert-butoxide, and potassium tert-butoxide.

18. The process of claim 11, wherein the sixth strong base is selected from the group consisting of lithium hydroxide, sodium hydroxide, potassium hydroxide, rubidium hydroxide, cesium hydroxide, calcium hydroxide, strontium hydroxide, and barium hydroxide.

19. A compound selected from the group consisting of formula 20a and formula 26a:

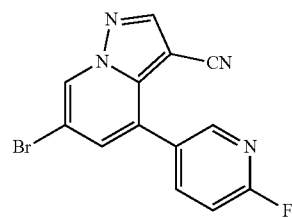

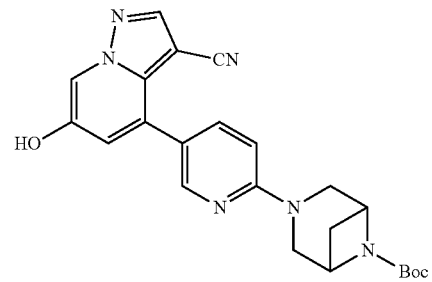

or a pharmaceutically acceptable salt thereof.

* * * * *